United States Patent
Robinson et al.

(10) Patent No.: US 9,827,059 B2
(45) Date of Patent: Nov. 28, 2017

(54) ADAPTABLE INTEGRATED ENERGY CONTROL SYSTEM FOR ELECTROSURGICAL TOOLS IN ROBOTIC SURGICAL SYSTEMS

(71) Applicant: INTUITIVE SURGICAL OPERATIONS, INC., Sunnyvale, CA (US)

(72) Inventors: David W. Robinson, Los Altos, CA (US); Thomas R. Nixon, San Jose, CA (US); Michael Hanuschik, Mountain View, CA (US); Randal P. Goldberg, San Mateo, CA (US); Jason Hemphill, Los Gatos, CA (US); David Q. Larkin, Menlo Park, CA (US); Paul Millman, San Jose, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

(21) Appl. No.: 15/161,158

(22) Filed: May 20, 2016

(65) Prior Publication Data

US 2016/0338786 A1 Nov. 24, 2016

Related U.S. Application Data

(60) Continuation of application No. 14/642,163, filed on Mar. 9, 2015, now Pat. No. 9,375,288, which is a
(Continued)

(51) Int. Cl.
*G06F 19/00* (2011.01)
*A61B 34/35* (2016.01)
(Continued)

(52) U.S. Cl.
CPC .......... *A61B 34/35* (2016.02); *A61B 18/1206* (2013.01); *A61B 34/25* (2016.02);
(Continued)

(58) Field of Classification Search
CPC .......... A61B 34/35; A61B 34/25; A61B 34/76
See application file for complete search history.

(56) References Cited

U.S. PATENT DOCUMENTS

| | | |
|---|---|---|
| 2,175,768 A | 10/1939 | Anthony |
| 2,249,618 A | 7/1941 | Perkins |

(Continued)

FOREIGN PATENT DOCUMENTS

| | | |
|---|---|---|
| CN | 1243690 A | 2/2000 |
| CN | 101297760 A | 11/2008 |

(Continued)

OTHER PUBLICATIONS 802.3af-2003—IEEE Standard for Information Technology—Telecommunications and Information Exchange Between Systems—Local and Metropolitan Area Networks—Specific Requirements [online], 2003, Current Version Jul. 22, 2003, DOI 10.1109/IEEESTD 2003.94284, Persistent Link: http://ieeexplore.ieee.org/servlet/opac?punumber=8612.

(Continued)

*Primary Examiner* — Ian Jen
(74) *Attorney, Agent, or Firm* — Jones Robb, PLLC

(57) ABSTRACT

A teleoperated surgical system may comprise a plurality of teleoperated surgical instruments; a user input device; and a controller operably coupled to the user input device and to the plurality of surgical instruments. The user input device may be configured to transmit an activation command to cause activation of a function of a first one of the plurality of surgical instruments in response to input at the user input device, the function being supported by remote-control (Continued)

supply equipment. The controller may be configured to output a feedback command to cause feedback to a user, the feedback indicating the first one of the plurality of surgical instruments is configured for activation in response to the activation command.

25 Claims, 31 Drawing Sheets

Related U.S. Application Data continuation of application No. 14/497,712, filed on Sep. 26, 2014, now abandoned, which is a continuation of application No. 13/800,856, filed on Mar. 13, 2013, now Pat. No. 8,862,268, which is a division of application No. 12/400,653, filed on Mar. 9, 2009, now Pat. No. 8,423,182.

(51) Int. Cl.
  *A61B 18/12* (2006.01)
  *A61B 34/00* (2016.01)
  *A61B 34/30* (2016.01)
  *A61B 18/14* (2006.01)
  *A61B 17/00* (2006.01)
  *A61B 18/00* (2006.01)

(52) U.S. Cl.
  CPC .............. *A61B 34/30* (2016.02); *A61B 34/76* (2016.02); *A61B 18/14* (2013.01); *A61B 2017/00477* (2013.01); *A61B 2017/00482* (2013.01); *A61B 2017/00973* (2013.01); *A61B 2018/00988* (2013.01)

(56) References Cited

U.S. PATENT DOCUMENTS

| | | |
|---|---|---|
| D141,099 S | 5/1945 | Baumgardner |
| D141,100 S | 5/1945 | Baumgardner |
| D141,101 S | 5/1945 | Baumgardner |
| D188,419 S | 7/1960 | Danesi |
| 3,184,703 A | 5/1965 | Piscitello et al. |
| 4,211,461 A | 7/1980 | Wescott |
| 4,284,312 A | 8/1981 | Patchett et al. |
| D290,458 S | 6/1987 | O'Leary |
| D319,625 S | 9/1991 | Nagasaka et al. |
| 5,180,316 A | 1/1993 | Miller et al. |
| D342,937 S | 1/1994 | Angel, Jr. et al. |
| 5,350,314 A | 9/1994 | Saba |
| D358,131 S | 5/1995 | Lorentzen |
| 5,364,332 S | 11/1995 | Sachs |
| D412,312 S | 7/1999 | Myers |
| D415,469 S | 10/1999 | Lee |
| 5,991,355 A | 11/1999 | Dahlke |
| D420,980 S | 2/2000 | Tennessen |
| 6,040,537 A * | 3/2000 | McClintock ............ H01H 21/26 200/86.5 |
| 6,074,388 A * | 6/2000 | Tockweiler ............ A61B 18/12 606/1 |
| D428,853 S | 8/2000 | Burwell et al. |
| 6,113,596 A * | 9/2000 | Hooven ................. A61B 18/14 606/42 |
| 6,237,604 B1 | 5/2001 | Burnside et al. |
| D460,046 S | 7/2002 | Wood |
| D460,049 S | 7/2002 | McCoy |
| 6,493,608 B1 * | 12/2002 | Niemeyer ............... B25J 9/1689 606/130 |
| 6,522,906 B1 * | 2/2003 | Salisbury, Jr. ......... A61B 8/12 600/102 |
| D472,523 S | 4/2003 | Hansen |
| D487,724 S | 3/2004 | Hsiao |
| 6,702,617 B1 | 3/2004 | Clement et al. |
| D488,130 S | 4/2004 | Hsiao |
| D491,526 S | 6/2004 | D'Addario et al. |
| 6,840,938 B1 | 1/2005 | Morley et al. |
| 6,849,071 B2 | 2/2005 | Whitman et al. |
| D512,378 S | 12/2005 | Dobler |
| 6,994,708 B2 | 2/2006 | Manzo |
| 6,997,723 B2 | 2/2006 | Lee |
| D517,501 S | 3/2006 | Kotyk |
| 7,122,032 B2 | 10/2006 | Shinmura et al. |
| D533,501 S | 12/2006 | Wakefield et al. |
| D543,148 S | 5/2007 | Suckle et al. |
| 7,217,269 B2 * | 5/2007 | El-Galley ........... A61B 18/1402 606/34 |
| D560,610 S | 1/2008 | McCoy |
| 7,320,700 B2 | 1/2008 | Cooper et al. |
| D563,883 S | 3/2008 | Dever |
| D563,884 S | 3/2008 | Dever |
| D565,981 S | 4/2008 | Radecke et al. |
| D566,046 S | 4/2008 | Gabel et al. |
| 7,353,068 B2 * | 4/2008 | Tanaka ........... A61B 17/320068 606/42 |
| 7,367,973 B2 | 5/2008 | Manzo et al. |
| 7,379,563 B2 | 5/2008 | Shamaie |
| 7,428,439 B1 * | 9/2008 | Reynolds ............... G06F 3/0383 318/400.18 |
| D585,380 S | 1/2009 | So |
| D587,205 S | 2/2009 | Wu et al. |
| 7,594,912 B2 | 9/2009 | Cooper et al. |
| D603,345 S | 11/2009 | Melzner et al. |
| D617,272 S | 6/2010 | The |
| D639,743 S | 6/2011 | Smith et al. |
| D639,744 S | 6/2011 | Smith et al. |
| 8,052,470 B1 | 11/2011 | Lin |
| 8,083,548 B1 | 12/2011 | Lin |
| 8,120,301 B2 | 2/2012 | Goldberg et al. |
| D658,586 S | 5/2012 | Lin |
| D668,225 S | 10/2012 | Lyford et al. |
| D668,226 S | 10/2012 | Lyford et al. |
| D672,718 S | 12/2012 | Lyford et al. |
| D672,719 S | 12/2012 | Lyford et al. |
| D672,720 S | 12/2012 | Lyford et al. |
| D672,722 S | 12/2012 | Kreitzer et al. |
| D672,723 S | 12/2012 | Kreitzer et al. |
| D673,119 S | 12/2012 | Lyford et al. |
| D673,120 S | 12/2012 | Lyford et al. |
| D673,121 S | 12/2012 | Lyford et al. |
| 8,398,541 B2 | 3/2013 | Dimaio et al. |
| 8,398,634 B2 | 3/2013 | Manzo et al. |
| 8,418,073 B2 | 4/2013 | Mohr et al. |
| 8,423,182 B2 | 4/2013 | Robinson et al. |
| D682,787 S | 5/2013 | Lyford et al. |
| D684,928 S | 6/2013 | Kreitzer et al. |
| D686,579 S | 7/2013 | Fujioka |
| 8,508,173 B2 | 8/2013 | Goldberg et al. |
| D690,266 S | 9/2013 | Dachs, II |
| D691,090 S | 10/2013 | Dachs |
| D691,091 S | 10/2013 | Dachs, II |
| D691,092 S | 10/2013 | Dachs |
| 8,657,808 B2 | 2/2014 | McPherson et al. |
| D702,642 S | 4/2014 | Dachs, II |
| D703,140 S | 4/2014 | Dachs, II |
| D703,612 S | 4/2014 | Dachs, II |
| 8,862,268 B2 | 10/2014 | Robinson et al. |
| 9,301,811 B2 | 4/2016 | Goldberg et al. |
| 9,375,288 B2 | 6/2016 | Robinson et al. |
| 2002/0049004 A1 | 4/2002 | Davis et al. |
| 2002/0152015 A1 * | 10/2002 | Seto .................... B60K 31/0008 701/96 |
| 2002/0173799 A1 | 11/2002 | Besharim et al. |
| 2003/0040204 A1 | 2/2003 | Chen et al. |
| 2003/0050654 A1 * | 3/2003 | Whitman ........... A61B 10/0233 606/167 |
| 2003/0135204 A1 | 7/2003 | Lee et al. |
| 2004/0152354 A1 | 8/2004 | Luther et al. |
| 2004/0167515 A1 | 8/2004 | Petersen et al. |
| 2005/0008043 A1 | 1/2005 | Kousek et al. |
| 2005/0021021 A1 * | 1/2005 | Foltz ..................... A61B 18/14 606/35 |

(56) References Cited

U.S. PATENT DOCUMENTS

| | | | |
|---|---|---|---|
| 2005/0080403 A1* | 4/2005 | Takahashi | A61B 17/00 606/1 |
| 2005/0251156 A1* | 11/2005 | Toth | G06F 19/3412 606/153 |
| 2005/0251228 A1* | 11/2005 | Hamel | A61B 17/32002 607/60 |
| 2006/0079889 A1 | 4/2006 | Scott et al. | |
| 2006/0087746 A1 | 4/2006 | Lipow | |
| 2006/0142657 A1 | 6/2006 | Quaid et al. | |
| 2006/0271260 A1* | 11/2006 | Matsuzaki | B60W 10/06 701/48 |
| 2007/0005045 A1* | 1/2007 | Mintz | B25J 9/0084 606/1 |
| 2007/0013336 A1 | 1/2007 | Nowlin et al. | |
| 2007/0016174 A1* | 1/2007 | Millman | A61M 1/0058 606/1 |
| 2007/0078539 A1* | 4/2007 | Kuhner | H01H 3/14 700/90 |
| 2007/0167968 A1 | 7/2007 | Pandey | |
| 2007/0239172 A1 | 10/2007 | Lee et al. | |
| 2008/0020714 A1 | 1/2008 | Mezhinsky et al. | |
| 2008/0046122 A1* | 2/2008 | Manzo | A61B 1/00149 700/245 |
| 2008/0125794 A1 | 5/2008 | Brock et al. | |
| 2008/0140158 A1* | 6/2008 | Hamel | A61B 17/32002 607/60 |
| 2008/0147089 A1 | 6/2008 | Loh et al. | |
| 2008/0183189 A1 | 7/2008 | Teichman et al. | |
| 2008/0217564 A1* | 9/2008 | Beyar | A61B 6/00 250/515.1 |
| 2008/0221473 A1 | 9/2008 | Calancie et al. | |
| 2008/0249547 A1 | 10/2008 | Dunn | |
| 2008/0262538 A1 | 10/2008 | Danitz et al. | |
| 2008/0319313 A1 | 12/2008 | Boivin et al. | |
| 2009/0009492 A1 | 1/2009 | Gregorio et al. | |
| 2009/0012533 A1* | 1/2009 | Barbagli | G06F 19/3406 606/130 |
| 2009/0024142 A1 | 1/2009 | Ruiz Morales | |
| 2009/0088634 A1* | 4/2009 | Zhao | B25J 9/1689 600/427 |
| 2009/0088774 A1* | 4/2009 | Swarup | A61B 34/37 606/130 |
| 2009/0248041 A1 | 10/2009 | Williams et al. | |
| 2009/0275940 A1 | 11/2009 | Malackowski et al. | |
| 2010/0082039 A1 | 4/2010 | Mohr et al. | |
| 2010/0191088 A1 | 7/2010 | Anderson et al. | |
| 2010/0228249 A1* | 9/2010 | Mohr | A61B 1/00009 606/41 |
| 2010/0228264 A1* | 9/2010 | Robinson | A61B 18/1206 606/130 |
| 2010/0234857 A1 | 9/2010 | Itkowitz et al. | |
| 2010/0305427 A1 | 12/2010 | Huber et al. | |
| 2011/0045680 A1 | 2/2011 | Beller et al. | |
| 2011/0079626 A1* | 4/2011 | Viola | A61B 17/07207 227/175.2 |
| 2011/0118752 A1 | 5/2011 | Itkowitz et al. | |
| 2011/0118753 A1 | 5/2011 | Itkowitz et al. | |
| 2011/0238079 A1* | 9/2011 | Hannaford | G06F 3/011 606/130 |
| 2011/0276058 A1 | 11/2011 | Choi et al. | |
| 2011/0282140 A1 | 11/2011 | Itkowitz et al. | |
| 2011/0282141 A1 | 11/2011 | Itkowitz et al. | |
| 2012/0046659 A1 | 2/2012 | Mueller | |
| 2012/0071891 A1 | 3/2012 | Itkowitz et al. | |
| 2012/0071892 A1 | 3/2012 | Itkowitz et al. | |
| 2012/0202388 A1 | 8/2012 | Selig et al. | |
| 2012/0310241 A1 | 12/2012 | Orszulak | |
| 2013/0053840 A1 | 2/2013 | Krapohl et al. | |
| 2013/0274734 A1 | 10/2013 | Maass et al. | |
| 2014/0128885 A1 | 5/2014 | Dachs, II et al. | |
| 2014/0128886 A1* | 5/2014 | Holop et al. | |
| 2014/0142591 A1* | 5/2014 | Alvarez | A61F 9/00736 606/130 |
| 2014/0180272 A1 | 6/2014 | Dachs, II et al. | |
| 2015/0012134 A1 | 1/2015 | Robinson et al. | |
| 2016/0192998 A1 | 7/2016 | Goldberg et al. | |

FOREIGN PATENT DOCUMENTS

| | | |
|---|---|---|
| CN | 102421387 B | 5/2015 |
| JP | H07308321 A | 11/1995 |
| WO | WO-9749340 A1 | 12/1997 |
| WO | WO-2008098085 A2 | 8/2008 |
| WO | WO-2010008126 A1 | 1/2010 |
| WO | WO-2010104753 A1 | 9/2010 |
| WO | WO-2011060139 A2 | 5/2011 |
| WO | WO-2011125007 A1 | 10/2011 |

OTHER PUBLICATIONS

Applied Surgical, Data Sheet for Gemini Operating Room, 1 Page, 2006; Internet: http://appliedsurgicalsolutions.com/.

Dugan, Kelli M., "Stepping Out," Birmingham Business Journal, Mar. 24, 2006, 2 pages; Internet: http://www.oadi.org/client%20news/Applied%20Surgical%20032406.pdf.

Erickson, J.R. et al., "Connectors Take on a new Life," Published Online on Sep. 1, 2012,< URL: http://www.designworlddonline.com/connectors-take-on-a-new-life/.

Extended European Search Report for Application No. 13851407.0, dated Sep. 9, 2016, 13 pages.

Extended European Search Report for Application No. 13836661.2, dated Apr. 28, 2016, 11 pages.

Harris, William, "How Haptic Technology Works," downloaded Oct. 24, 2008, 6 pages; Internet: http://electronics.howstuffworks.com/gadgets/other-gadgets/haptic-technology4.htm.

International Search Report and Written Opinion for Application No. PCT/US2013/059938, dated Dec. 10, 2013, 11 pages.

International Search Report and Written Opinion for Application No. PCT/US2013/068059, dated Feb. 11, 2014, 18 pages.

Linemaster Switch Corp., Brochure titled "Precision Begins with a Linemaster Switch," 8 pages, 2000.

Linemaster Switch Corp., Data Sheet for Linemaster Wireless Linear Foot Switch, Lit-002 Rev D, 2 pages, downloaded Jan. 2, 2009; Internet: http://www.linemaster.com/media/DataSheets/LIT-002%20Rev%20Dsm.pdf.

Linemaster Switch Corp., Information sheet for Linemaster Infrared Wireless Linear Foot Switch, 2 pages, downloaded Jan. 2, 2009; Internet: http://www.linemaster.com/wirelesslinear.shtml.

Medical Design Magazine, "Wireless Footswitch Controls Several Surgical Devices," Nov. 1, 2006, 1 page; Internet: http://medicaldesign.com/engineering-prototyping/wireless_footswitch_controls/index.html.

Partial Supplementary European Search Report for Application No. 13851407.0, dated May 23, 2016, 9 pages.

PCT/US10/26307 International Search Report and Written Opinion of the International Searching Authority, dated Jul. 22, 2010, 9 pages.

PCT/US10/56345 International Search Report and Written Opinion of the International Searching Authority, dated Feb. 8, 2011, 15 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wikipedia, entry on "Ergonomics," printed Feb. 24, 2009 at 11:24 p.m., 10 pages; Internet: http://en.wikipedia.org/wiki/Ergonomics.

Office Action dated Oct. 8, 2016 for Chinese Application No. 201380048070.8 filed Sep. 16, 2013, 15 pages.

* cited by examiner

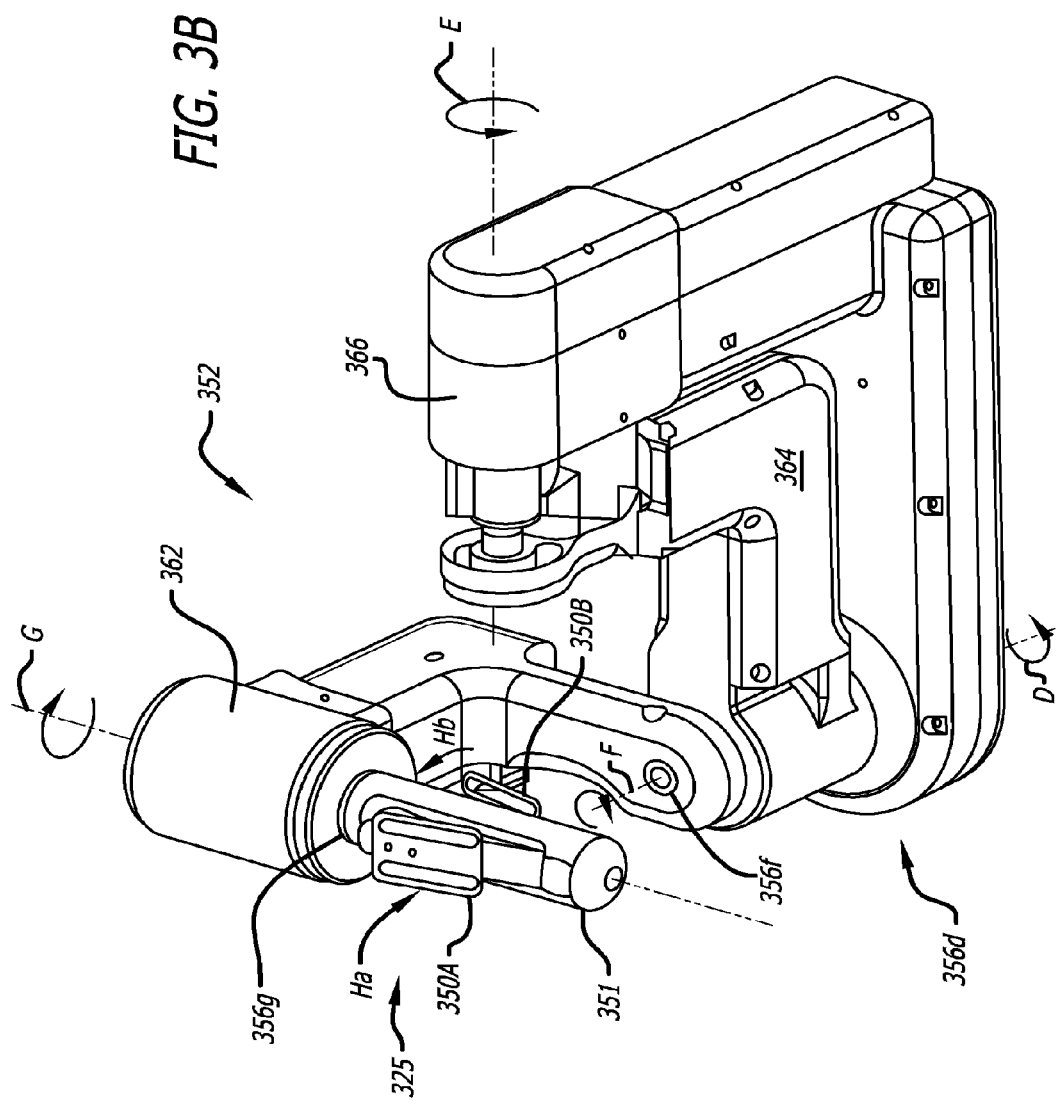

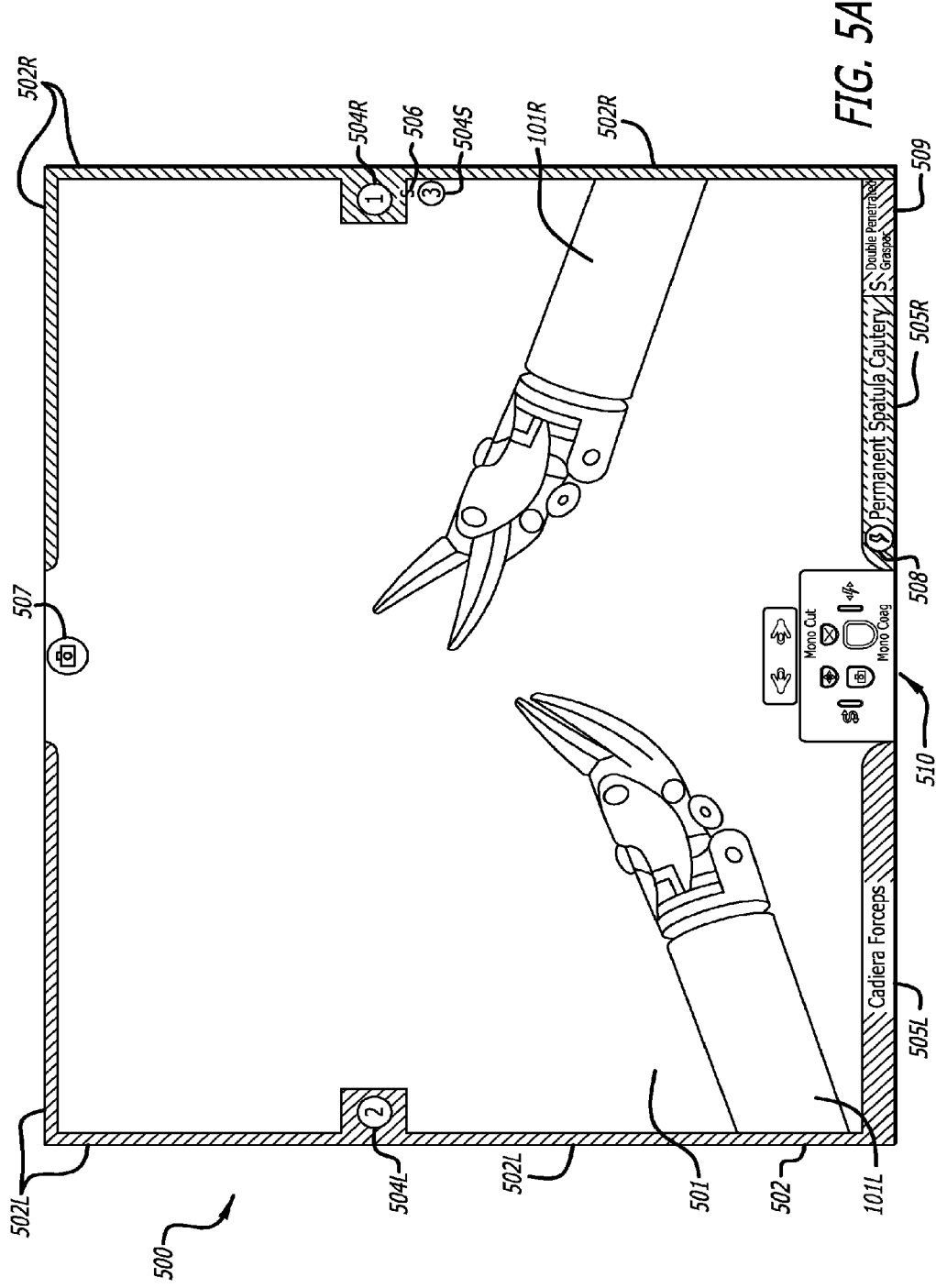

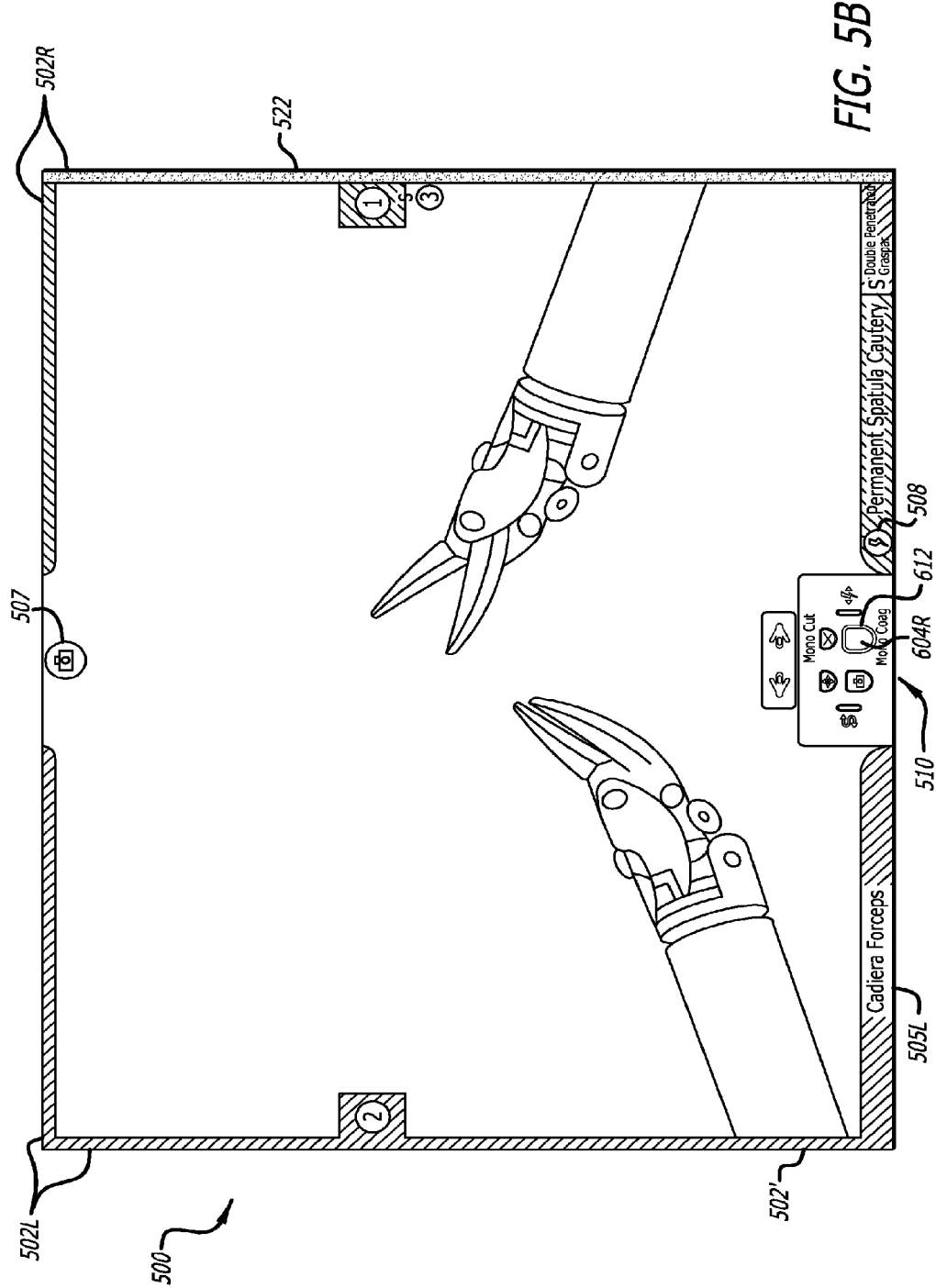

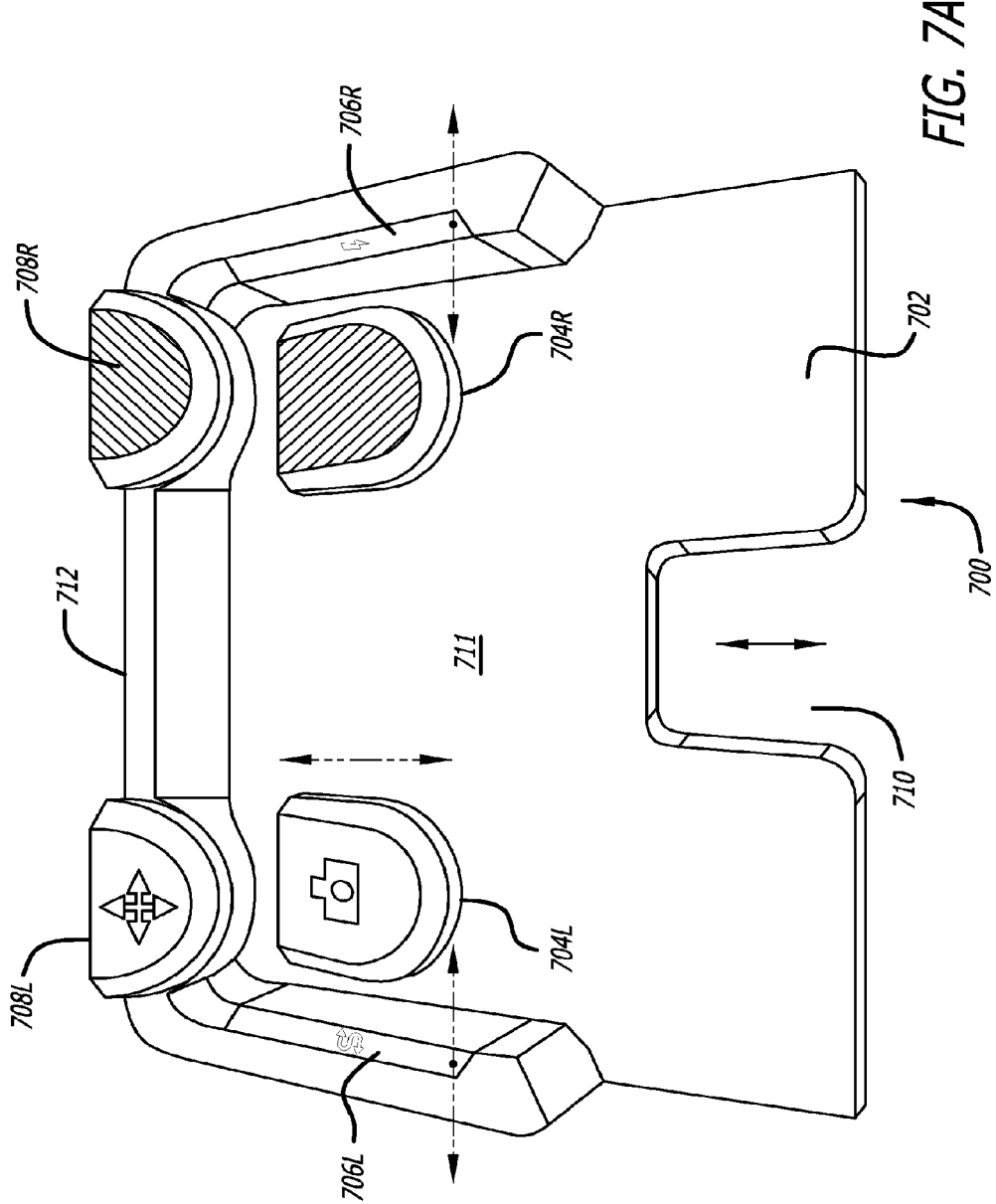

ADAPTABLE INTEGRATED ENERGY CONTROL SYSTEM FOR ELECTROSURGICAL TOOLS IN ROBOTIC SURGICAL SYSTEMS

This application is a continuation application of U.S. application Ser. No. 14/642,163 (filed Mar. 9, 2015), which is a continuation of U.S. application Ser. No. 14/497,712 (filed Sep. 26, 2014, now abandoned), which is a continuation of U.S. application Ser. No. 13/800,856 (filed Mar. 13, 2013, now U.S. Pat. No. 8,862,268), which is a divisional of U.S. application Ser. No. 12/400,653 (filed Mar. 9, 2009, now U.S. Pat. No. 8,423,182), each of which is incorporated herein by reference in its entirety.

FIELD

The embodiments of the invention are generally related to integrated control of equipment that supports tools and the equipment to tool interface in robotic surgical systems.

BACKGROUND

Robotic surgical systems may have multiple robotic arms to which a plurality of robotic surgical tools (also referred to as robotic surgical instruments) may be coupled. One such category of robotic surgical tools is electrosurgical tools which includes a monopolar electrosurgical tool or a bipolar electrosurgical tool as well as harmonic, laser, ultrasound tools. Another category of robotic surgical tools is tissue manipulation tools which may have articulated end effectors (such as jaws, scissors, graspers, needle holders, micro dissectors, staple appliers, tackers, suction/irrigation tools, clip appliers, or the like) or non-articulated end effectors (such as cutting blades, irrigators, catheters, suction orifices, or the like) without electrosurgical elements. While electrosurgical tools are mechanically coupled to a robotic arm to control its movement, they are also coupled to electrosurgical energy generating units (ESUs) so that energy may be applied to tissue at or near its end effectors.

Electrosurgical tools in a robotic surgical system may be mechanically controlled by one or both of a surgeon's left and/or right hands and electrically controlled to deliver energy to tissue by a surgeon's foot. When viewing an image of an electrosurgical tool and tissue on a display device captured through a camera, it may be difficult to see the effect of an inadvertent application of energy to the tissue. While a single mis-application of energy to tissue may cause some damage, increasing damage is likely to be caused to tissue with repetitive mis-application of energy.

The inadvertent application of energy to tissue may be caused by a mis-positioned foot over an incorrect pedal. To avoid a mis-positioned foot, a surgeon may have to look away from the display device to see his foot and properly position it over the proper one of a plurality of foot pedal switches. The inadvertent application of energy to tissue may also be caused surgeon confusion as to which of a plurality of electrosurgical tools in the surgical site is being energized. Moreover, if a surgeon's concentration is narrowly focused on the wrong surgical tool, he may not see the tissue damage being done by its mis-application. Energizing the proper electrosurgical tool in a surgical site can increase surgical efficiency and avoid excessive tissue damage to a patient.

Furthermore with additional types of robotic surgical tools being used with controllable equipment, it has become more difficult for a surgeon to simultaneously control all of the desired instruments.

BRIEF SUMMARY

The embodiments of the invention are summarized by the claims that follow below.

BRIEF DESCRIPTIONS OF THE DRAWINGS

FIG. 3B is a perspective view of an exemplary gimbaled control input wrist pivotally supporting a master grip control handle (also referred to as a master grip control input) for the robotic surgical master control console of FIG. 3A to control robotic surgical tools including a robotic electrosurgical tool.

FIGS. 5A-5C illustrate images displayed by a display device including a graphical user interface overlaid onto video images of a work site in accordance with one embodiment of the invention.

FIGS. 7A-7F are various views of an integrated pedal system of the surgeon's control console.

Figure 1A:
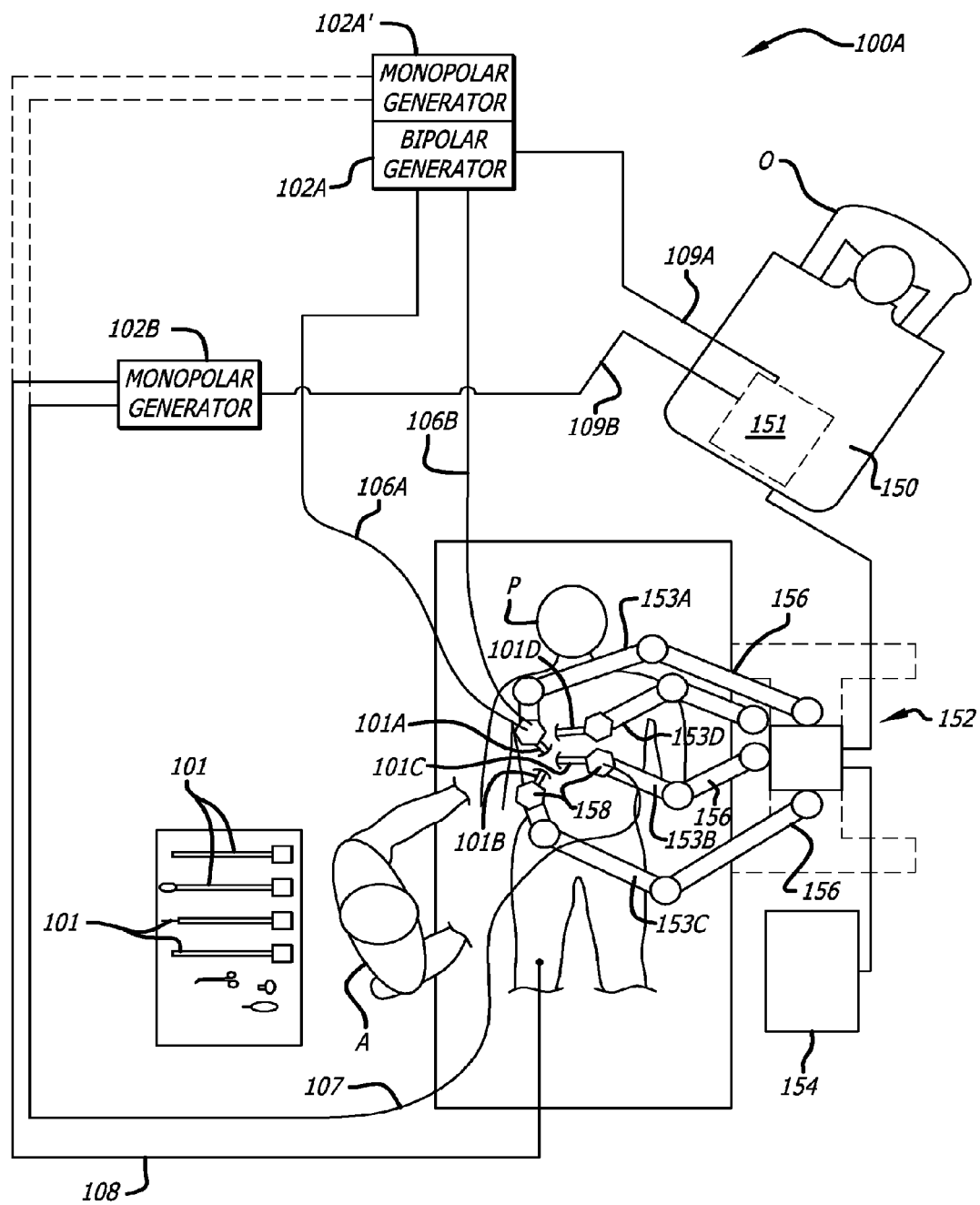
FIG. 1A is a block diagram of a first robotic surgery system to perform minimally invasive robotic surgical procedures using a robotic electrosurgical tool.

Note that these figures are for illustration purposes and do not necessarily reflect the actual shape, size, or dimensions of objects being illustrated.

DETAILED DESCRIPTION

In the following detailed description of the embodiments of the invention, numerous specific details are set forth in order to provide a thorough understanding of the embodiments of the invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

Introduction

Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like. During these robotic surgical procedures, surgeons may use high voltage, low current electrical energy of various wave forms to perform such tasks as cautery, cutting tissue, or sealing a vessel. Electrical energy supply devices (referred to as electrosurgical generating units ESU) are coupled to surgical instruments and typically activated by a foot pedal switch of a foot pedal. One or more foot pedals in a surgeon's console and their corresponding switches may be used to activate these electrical energy supply devices. The foot pedal switches in the surgeon's console replace the original equipment manufactures (OEM) foot pedal switches that are packaged with the ESUs as standard equipment. An OEM pedal directly connects to a specific ESU and may not be used to control other equipment.

In one embodiment of the invention, a method for a minimally invasive surgical system is disclosed including reading first tool information from a storage device in a first robotic surgical tool mounted to a first robotic arm to at least determine a first tool type; reading equipment information about one or more remote controlled equipment for control thereof; comparing the first tool information with the equipment information to appropriately match a first remote controlled equipment of the one or more remote controlled equipment to the first robotic surgical tool; and mapping one or more user interface input devices of a first control console to control the first remote controlled equipment to support a function of the first robotic surgical tool.

In another embodiment of the invention, an adaptable integrated user interface controller for a control console is disclosed. The adaptable integrated user interface controller includes mapping logic to couple to one or more user interface input devices to receive control signals in response to selection of the one or more user interface input devices; and an adaptable input/output (I/O) interface coupled to the mapping logic. The adaptable I/O interface couples to one or more pieces of remote controlled equipment. The adaptable I/O interface reads equipment information of the one or more pieces of remote controlled equipment and adapt signal levels of the one or more user interface input devices to signal levels of the one or more pieces of remote controlled equipment. The mapping logic selectively maps the one or more user interface input devices to the one or more pieces of remote controlled equipment in response to the equipment information regarding the one or more remote controlled equipment, tool information of one or more robotic surgical tools controllable by the control console, and an active tool control signal selected by a user. The active tool control signal swaps control of at least one user interface device to the remote controlled equipment between the one or more robotic surgical tools.

In yet another embodiment of the invention, another adaptable integrated user interface controller for a control console is disclosed. The adaptable integrated user interface controller in this case includes mapping logic to couple to one or more user interface input devices to receive control signals in response to selection of the one or more user interface input devices; and a tool interface coupled to one or more robotic surgical tools. The tool interface reads tool information from one or more robotic surgical tools that are controllable by the control console and reads equipment information of one or more pieces of remote controlled equipment from the one or more intelligent robotic surgical tools. The mapping logic selectively maps the one or more user interface input devices to the one or more intelligent robotic surgical tools to remotely control the one or more remote controlled equipment through the intelligent one or more robotic surgical tools. The selective mapping performed by the mapping logic is in response to the equipment information of the one or more pieces of remote controlled equipment, tool information of the one or more intelligent robotic surgical tools, and an active tool control signal selected by a user. The active tool control signal swaps control of at least one user interface device to the remote controlled equipment between the one or more intelligent robotic surgical tools.

In still another embodiment of the invention, a minimally invasive surgical system is disclosed. The minimally invasive surgical system includes one or more robotic surgical tools, an integrated user interface controller, and a processor coupled to the integrated user interface controller and the one or more robotic surgical tools. The integrated user interface controller has a first interface coupled to one or more pieces of remote controlled equipment and a second interface coupled to one or more user interface input devices of a first control console. The integrated user interface controller further has mapping logic to map the one or more user interface input devices to control one or more of the one or more pieces of first remote controlled equipment. In response to stored program instructions in a storage device coupled to the processor, the processor becomes configured to read first tool information from a storage device in a first robotic surgical tool mounted to a first robotic arm to at least determine a first tool type; read equipment information about one or more pieces of remote controlled equipment for control thereof; compare the first tool information with the equipment information to appropriately match the one or more remote controlled equipment to the first robotic surgical tool; and control the mapping logic to map the one or more user interface input devices of the first control console to control the first remote controlled equipment to support a function of the first robotic surgical tool.

Robotic Surgical Systems

Robotic surgery generally involves the use of a robot manipulator that has multiple robotic manipulator arms. One or more of the robotic manipulator arms often support a robotic surgical tool or instrument which may be an electrosurgical tool or a non-electrosurgical tool. One or more of the robotic manipulator arms are often used to support a surgical image capture device such as an endoscope (which may be any of a variety of structures such as a laparoscope, an arthroscope, a hysteroscope, or the like), or, optionally, some other imaging modality (such as ultrasound, fluoroscopy, magnetic resonance imaging, or the like). Typically, the robotic manipulator arms will support at least two robotic surgical tools corresponding to the two hands of a surgeon and one image capture device.

Referring now to FIG. 1A, a block diagram of a robotic surgery system 100A is illustrated to perform minimally invasive robotic surgical procedures using robotic electrosurgical tools 101A and 101B. Each of the robotic electrosurgical tools 101A and 101B are robotic endoscopic surgical instrument that are manipulated by a slaved robotic manipulator and remotely controlled by control signals received from a master control console. In contrast, manual endoscopic surgical instruments are directly controlled by hand. Robotic electrosurgical tool 101A is a bipolar electrosurgical tool. Robotic electrosurgical tool 101B is a monopolar electrosurgical tool.

A user or operator O (generally a surgeon) performs a minimally invasive surgical procedure on patient P by manipulating input devices at a master control console 150. The master control console 150 may also be referred to herein as a control console, a surgeon console, or a master console. A computer 151 of the console 150 directs movement of robotically controlled endoscopic surgical instruments (generally numbered 101), effecting movement of the instruments using a robotic surgical manipulator 152. The robotic surgical manipulator 152 may also be referred to as robotic patient-side cart system or simply as a cart. The robotic surgical manipulator 152 has one or more robotic arms 153. Typically, the robotic surgical manipulator 152 includes at least three robotic manipulator arms 153 supported by linkages, with a central arm supporting an endoscopic camera 101C and the robotic surgical arms 153 to left and right of center supporting tissue manipulation tools and the robotic surgical tool 101A.

An assistant A may assist in pre-positioning of the robotic surgical manipulator 152 relative to patient P as well as swapping tools or instruments 101 for alternative tool structures, and the like, while viewing the internal surgical site via an assistant's display 154. The image of the internal surgical site shown to A by the assistant's display 154 and operator O by surgeon's console 150 is provided by one of the surgical instruments 101 supported by the robotic surgical manipulator 152.

Generally, the robotic arms 153 of robotic surgical manipulator 152 include a positioning portion and a driven portion. The positioning portion of the robotic surgical manipulator 152 remains in a fixed configuration during surgery while manipulating tissue. The driven portion of the robotic surgical manipulator 152 is actively articulated under the direction of the operator O generating control signals at the surgeon's console 150 during surgery. The actively driven portion of the arms 153 is herein referred to as an actuating portion 158. The positioning portion of the robotic arms 153 that are in a fixed configuration during surgery may be referred to as positioning linkage and/or "set-up joint" 156,156'.

To support the functionality of the electrosurgical robotic tools 101A-101B, the robotic surgical system 100 may further include one or more electrosurgical generators 102A-102B. The one or more electrosurgical generators 102A-102B are remotely controlled by the master console 150 over the control cables 109A-109B by a surgeon operating the master console.

The electrosurgical generator 102A is a bipolar generator. A pair of wires 106A-106B couple between the bipolar electrosurgical generator 102A and a bipolar electrosurgical robotic tool 101A. The pair of wires pair of wires 106A-106B may transfer the energy of the bipolar electrosurgical generator 102A to a respective pair of end effectors of the bipolar electrosurgical robotic tool 101A to cauterize or seal tissue.

The electrosurgical generator 102B is a monopolar generator. A wire 107 couples between the monopolar electrosurgical generator 102B and a monopolar electrosurgical robotic tool 101B. A ground wire 108 couples between the monopolar electrosurgical generator 102B and patient P. The wire 107 may transfer the energy of the monopolar electrosurgical generator 102B to an end effector of the monopolar electrosurgical robotic tool 101B to cauterize or seal tissue. A monopolar electrosurgical generator and a bipolar electrosurgical generator may be combined together into one electrosurgical generator 102A' that can be remotely controlled by two sets of controls from the control console 150. That is, a first set of controls of the equipment 102A' can be used to control one function of the remote controlled equipment to supply (e.g., monopolar electrosurgical energy) a first robotic surgical tool while a second set of controls of the equipment can be used to control another function of the remote controlled equipment to supply (e.g., bipolar electrosurgical energy) a second robotic surgical tool. The remote controlled equipment may also be referred to as remote controllable equipment or remote controlled supply equipment. The robotic surgical tools that couple to the remote controlled equipment to receive a supply may also be referred to as supply controllable tools.

Much of the description herein is directed to remote controlled electrosurgical generators and control of the supply of electrosurgical energy to robotic electrosurgical tools. However, the description herein is more general in that it is equally applicable to other types of remote controlled supply equipment (e.g., laser generator) and supply controllable tools (e.g., laser surgical tool). The remote controlled supply equipment may be used to supply vacuum, gasses, liquids, energy (e.g., electrical, laser, ultrasound), mechanical torques, mechanical push/pull forces, data signals, control signals, etc. to support functions of other types of robotic surgical tools (e.g., ultrasound, lasers, staplers). For example, a robotic surgical tool may combine the function of laser cutting and ultrasound together that is supported by a remote controlled laser generator and a remote controlled ultrasound generator, both of which can be remotely controlled from the surgeon console. For further detail, see U.S. application Ser. No. 12/060,112, entitled ROBOTIC SURGICAL TOOLS FOR LASER MARKING AND LASER CUTTING, filed by Matthew Williams et al. on Mar. 31, 2008, which is incorporated herein by reference.

Figure 1B:
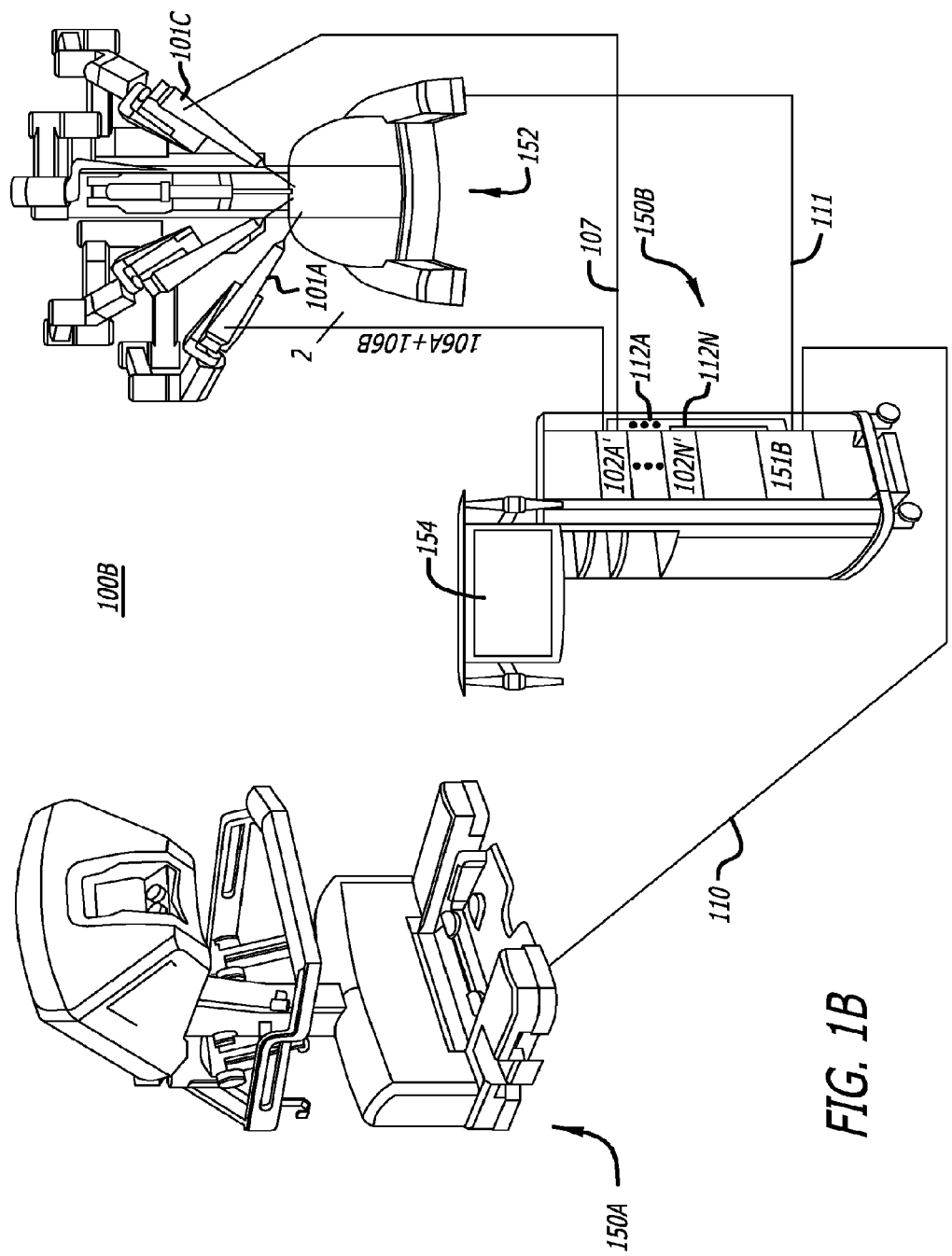
FIG. 1B is a block diagram of a second robotic surgery system to perform minimally invasive robotic surgical procedures using a robotic electrosurgical tool.

Referring now to FIG. 1B, a block diagram of a robotic surgery system 100B is illustrated. The robotic surgery system 100B is similar to the robotic surgery system 100A but with a control cart 150B being introduced between the surgeon's console 150A and the patient side cart 152. The control cart 150B includes a computer 151B, and optionally, an external monitor 154. To further control or support the robotic surgical tools, the control cart 150B includes one or more pieces of remote controllable equipment 102A'-102N'.

One piece of remote controllable equipment 102A' mounted in the control cart may be an electrosurgical generator that combines a monopolar electrosurgical generator and a bipolar electrosurgical generator together to supply electrosurgical energy to two electrosurgical tools 101A-101B. A pair of wires 106A-106B couple between the electrosurgical generator 102A' for a bipolar electrosurgical robotic tool 101A. The pair of wires pair of wires 106A-106B may transfer the energy of the bipolar electrosurgical generator 102A' to a respective pair of end effectors of the bipolar electrosurgical robotic tool 101A to cauterize or seal tissue. A wire 107 couples between the electrosurgical generator 102A' and a monopolar electrosurgical robotic tool 101B. A ground wire 108 (not shown in FIG. 1A, see FIG. 1B) is used to couple between the electrosurgical generator 102A' and a patient P.

A control cable 110 couples between the computer 151B of the control cart 150B and the surgeon's console to control the surgical system, including the remote controllable equipment and the robotic arms and robotic surgical tools. A control cable 111 is coupled the computer 151B and the patient side cart 152 for the surgeon's console to control the robotic arms and robotic surgical tools through the control cart.

Smart cables 112A-112N may be respectively coupled between the one or more pieces of remote controllable equipment 102A'-102N' and the computer 151B in the control cart 150B. With these connections, the surgeon's console can control the remote controllable equipment with its foot pedals and master controllers. In this manner, the control of the remote controllable equipment 102A'-102N' may be integrated into the surgeon's console. Its foot pedals and master controllers become integrated control mechanisms that a surgeon may use to control every aspect of the surgical system to make robotic surgery more efficient. Advanced user interfaces may be used to provide improved control and feedback of operating the remote controllable equipment with the robotic surgical tools.

Patient Side Cart (Robotic Surgical Manipulator)

Figure 2A:
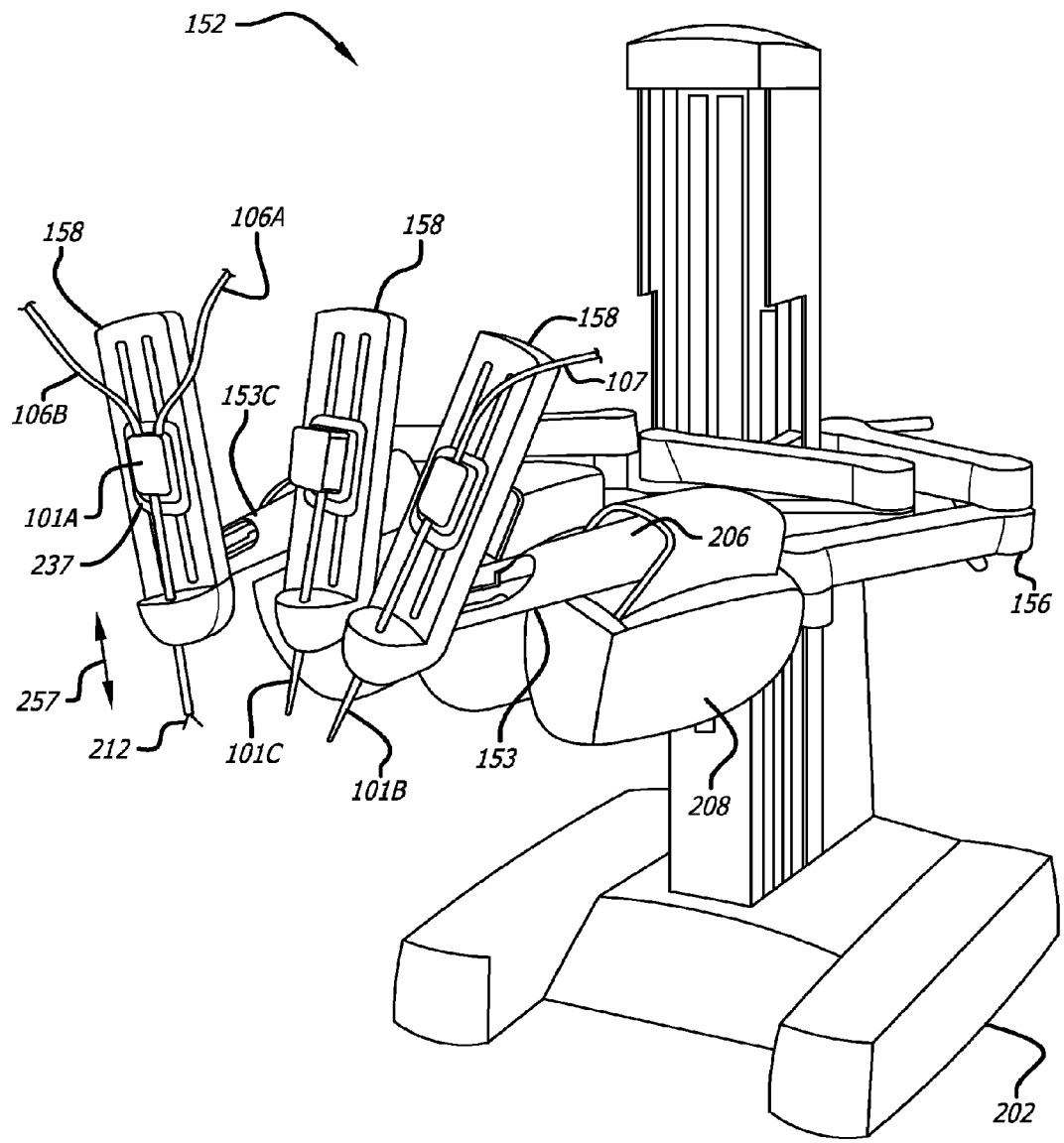
FIG. 2A is a perspective view of a robotic surgical manipulator with a plurality of robotic surgical arms at least one of which includes a robotic electrosurgical tool.

Referring now to FIG. 2A, a perspective view of the robotic surgical manipulator 152 is illustrated. The robotic surgical manipulator 152 may also be referred to as a patient side cart (PSC).

The robotic surgical manipulator 152 has one or more robotic surgical arms 153. The robotic arm 153C includes an electrosurgical robotic tool 101A coupled thereto. The robotic surgical manipulator 152 further includes a base 202 from which the robotic surgical instruments 101 may be supported. More specifically, the robotic surgical instruments 101 are each supported by the positioning linkage 156 and the actuating portion 158 of the arms 153. It should be noted that these linkage structures are here illustrated with protective covers 206,208 extending over much of the robotic arms. It should be understood that these protective covers 206,208 are optional, and may be limited in size or entirely eliminated in some embodiments to minimize the inertia that is manipulated by the servomechanism, and to limit the overall weight of robotic surgical manipulator 152.

Each of the robotic surgical tools 101A-101C, releasably couple to a moveable carriage 237 near an end of each robotic surgical arm. Each moveable carriage 237, with the robotic surgical tool mounted thereto, can be driven to translate along a linear guide formation 260 in the actuating portion 158 of the robotic surgical arms 153 in the direction of arrow 257.

The robotic surgical manipulator 152 generally has dimensions suitable for transporting between operating rooms. It typically can fit through standard operating room doors and onto standard hospital elevators. The robotic surgical manipulator 152 may have a weight and a wheel (or other transportation) system that allows the cart to be positioned adjacent an operating table by a single attendant. The robotic surgical manipulator 152 may be sufficiently stable during transport to avoid tipping, and to easily withstand overturning moments that may be imposed at the ends of the robotic arms during use.

Each of the robotic manipulating arms 153 preferably includes a linkage that constrains the movement of the surgical tool 101 mounted thereto. More specifically, linkage includes rigid links coupled together by rotational joints in a parallelogram arrangement so that the robotic surgical tools rotate around a point in space. At the point in space, the robotic arm can pivot the robotic surgical tool about a pitch axis and a yaw axis. The pitch and yaw axes intersect at the point, which is aligned along a shaft of robotic surgical tool. The shaft is a rotatable hollow tube that may have a number of cables of a cable drive system to control the movement of the end effectors 212.

The robotic arm provides further degrees of freedom of movement to the robotic surgical tool. Along an insertion axis, parallel to the central axis of the shaft of the robotic surgical tool, the robotic surgical tool may slide into and out from a surgical site as indicated by arrow 257. The robotic surgical tool can also rotate about the insertion axis. As the robotic surgical tool slides along or rotates about the insertion axis, the center point is relatively fixed with respect to the base patient side cart 152. That is, the entire robotic arm is generally moved in order to maintain or re-position back to the center point.

The linkage of the robotic arm may be driven by a series of motors therein in response to commands from a processor or computer. The motors in the robotic arm are also used to rotate and/or pivot the robotic surgical tool at the center point around the axes. If a robotic surgical tool 101 further has end effectors to be articulated or actuated, still other motors in the robotic arm may be used to control the end effectors. Additionally, the motion provided by the motors may be mechanically transferred to a different location such as by using pulleys, cables, gears, links, cams, cam followers, and the like or other known means of transfer, such as pneumatics, hydraulics, or electronics.

The robotic surgical tools 101 are generally sterile structures, often being sterilizable and/or being provided in hermetically sealed packages for use. As the robotic surgical tools 101 will be removed and replaced repeatedly during many procedures, a tool holder could potentially be exposed to contamination if the interface directly engages the tool holder. To avoid contamination to a tool holder and possible cross contamination between patients, an adaptor for coupling to robotic surgical tools 101 is provided in a robotic arm of the robotic surgical manipulator.

Figure 2D:
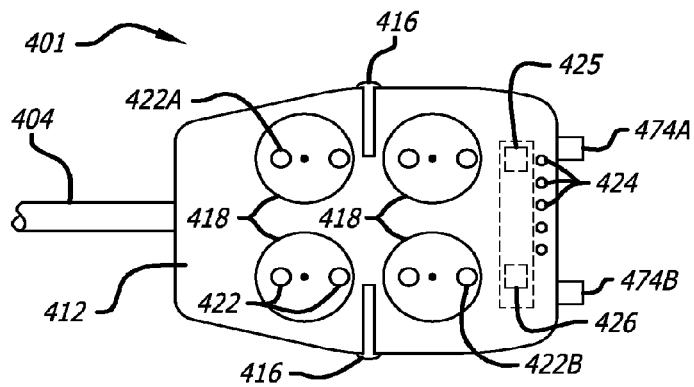
FIG. 2D illustrates a back side of an exemplary robotic electrosurgical instrument or tool that interfaces to a robotic surgical arm.
Figure 2C:
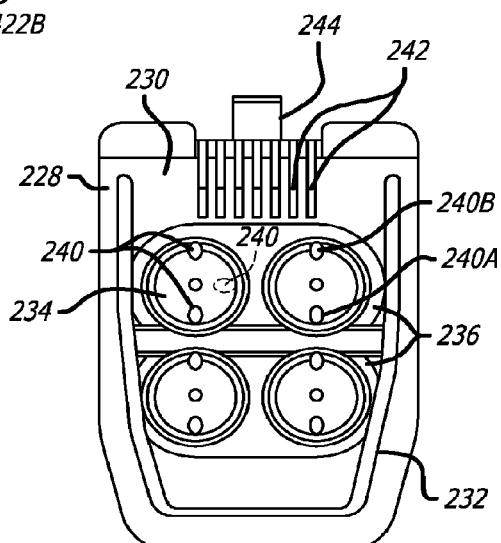
FIG. 2C illustrates a top view of the adapter of the robotic surgical arm of FIG. 2C to which the robotic electrosurgical tool may be mounted.
Figure 2B:
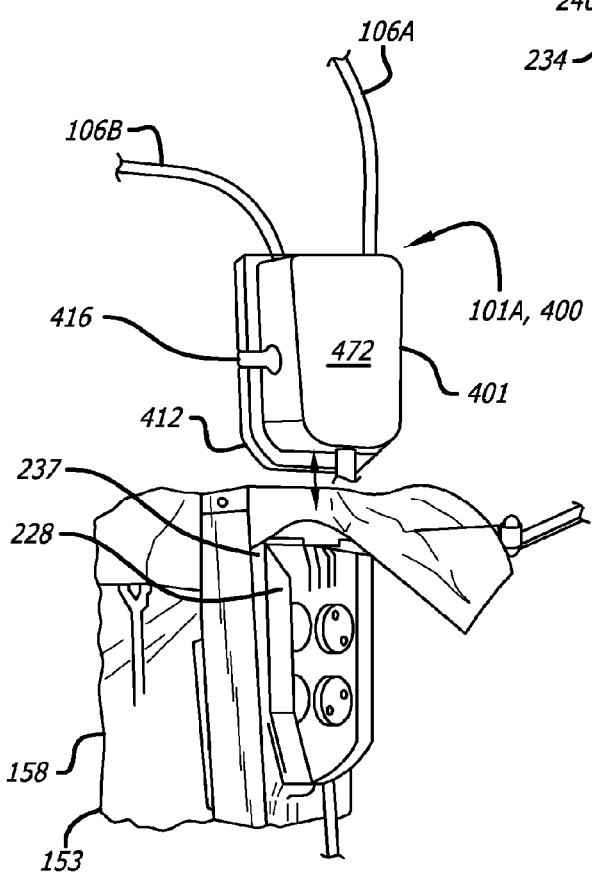
FIG. 2B illustrates mounting of the robotic electrosurgical tool to an adapter of the robotic surgical arm.

Referring now to FIGS. 2B-2D, the mounting of the robotic surgical tool 101A to an adapter 228 of the robotic surgical arm is now briefly described.

The robotic surgical arm 153 may include an adapter 228 to which the electrosurgical robotic tool 101A or other surgical tool 101 may be mounted. FIG. 2D illustrates a front side of an exemplary adapter 228. The front side of the adaptor 128 is generally referred to as a tool side 230 and the opposite side is generally referred to as a holder side (not shown).

FIG. 2B illustrates a back side of an exemplary electrosurgical robotic tool 400 as the surgical robotic tool 101A. The robotic surgical tool 400 includes an exemplary mountable housing 401 including an interface base 412 that can be coupled to the adapter 228 to mount the tool 400 to a robotic arm of a surgical robotic manipulator. The interface base 412 and the adapter 228 may be electrically and mechanically coupled together to actuate the robotic surgical tool 400. Rotatably coupled to the interface base 412 are one or more rotatable receiving members 418, also referred to as input disks. Each of the one or more rotatable receiving members 418 includes a pair of pins 422A and 422B generally referred to as pins 422. Pin 422A is located closer to the center of each rotatable receive member 418 than pin 422B. The one or more rotatable receiving members 418 can mechanically couple respectively to one or more rotatable drivers 234 of the adapter 228. The robotic surgical tool 101A may further include release levers 416 to release it from the adapter 228 and the robotic arm.

The interface base 412 may further include one or more electrical contacts or pins 424 to electrically couple to terminals of an electrical connector 242 of the adapter 228. One or more terminals of the electrical connector 242 that can couple to the electrical contacts or pins 424 of the tool may be used to make electrocautery connections, such as between an integrated controller and the tool and/or between the tool and electrosurgical generating units. The interface base 412 may further include a printed circuit board 425 and one or more integrated circuits 426 coupled thereto and to the one or more pins 424. The one or more integrated circuits 426 store tool information that may be used to identify the type of robotic surgical tool coupled to the robotic arm, so that it may be properly controlled by the master control console 150.

Referring to FIGS. 2B and 2D, a robotic electrosurgical tool or instrument 400 is illustrated. The robotic electrosurgical tool or instrument 400 includes a mountable housing 401, an elongated shaft 404 having a proximal end and a distal end; and end effectors (not shown) coupled near the distal end of the shaft 404. The mountable housing 401 includes an interface or tool base 412 coupled to the proximal end of the shaft 404. The mountable housing 401 may further include one or more electrical connectors 474A-474B, a cover 472, and one or more release levers 416. At the distal end of the shaft 404, a mechanical wrist (not shown) may be used to move the end effectors.

The interface or tool base 412 of the tool 400 can couple to an adapter 228 so that it is removeably connectable to the robotic surgical system. Other surgical tools with the same type of tool base may also couple to the adapter and then the robotic arm. During surgery, the adapter 228 is coupled to the moveable carriage 237. Thus, with the electrosurgical tool 400 mounted to the adapter 228, it can translate with the carriage 237 along an insertion axis of the robotic surgical arm 153 as indicated by arrow 257 in FIG. 2A. The tool base 412 includes receiving elements or input disks 418 that releaseably couple through an adapter to a rotatable driving element 234 that is mounted on the carriage 237 of the robotic arm assembly 153. The rotatable driving elements 234 of the carriage 237 are generally coupled to actuators (not shown), such as electric motors or the like, to cause selective angular displacement of each in the carriage 237.

When mounted to a robotic surgical arm 153, end effectors may have a plurality of degrees of freedom of movement relative to arm 153, in addition to actuation movement of the end effectors. The end effectors of the robotic surgical tool are used in performing a surgical operation such as cutting, shearing, grasping, gripping, clamping, engaging, or contacting tissue adjacent a surgical site. With an electrosurgical tool, a conductor electrically communicates with at least one of the end effectors to deliver electrical energy to tissue clamped by the gripping jaws.

As shown in FIG. 2D, the tool base 412 may be enclosed by a cover 472 to which one or more electrical connectors 474A-474B may be mounted. The one or more electrical connectors 474A-474B can receive one or more cables 106A-106B,107 to couple to an electrosurgical generator unit, such as the bipolar generator 102A, the monopolar generator 102B, or a combined monopolar/bipolar generator 102A' illustrated in FIG. 1A. One or more wires within the tools electrically couple between the electrical connectors 474A-474B and the electrodes at the one or more end effectors of the tool. Alternatively, one or more terminals of the electrical connector 242 that can couple to the electrical contacts or pins 424 of the tool may be used to make the electrocautery connections between the tool and the electrosurgical generating units.

The adapter 228 includes one or more rotatable drivers 234 rotatably coupled to a floating plate 236. The rotatable drivers 234 are resiliently mounted to the floating plate 236 by resilient radial members which extend into a circumferential indentation about the rotatable drivers. The rotatable drivers 234 can move axially relative to floating plate 236 by deflection of these resilient structures.

The floating plate 236 has a limited range of movement relative to the surrounding adaptor structure normal to the major surfaces of the adaptor. Axial movement of the floating plate helps decouple the rotatable drivers 234 from a robotic surgical tool 101 when its release levers 416 are actuated.

The one or more rotatable drivers 234 of the adapter 228 may mechanically couple to a part of the surgical tools 101. Each of the rotatable drivers 234 may include one or more openings 240 to receive protrusions or pins 422 of rotatable receiving members 418 of the robotic surgical tools 101. The openings 240 in the rotatable drivers 234 are configured to accurately align with the rotatable receiving elements 418 of the surgical tools 101.

The inner pins 422A and the outer pins 422B of the rotatable receiving elements 418 respectively align with the opening 240A and the opening 240B in each rotatable driver. The pins 422A and openings 240A are at differing distances from the axis of rotation than the pins 422B and openings 240B so as to ensure that rotatable drivers 234 and the rotatable receiving elements 418 are not aligned 180 degrees out of phase from their intended position. Additionally, each of the openings 240 in the rotatable drivers may be slightly radially elongated so as to fittingly receive the pins in the circumferential orientation. This allows the pins 422 to slide radially within the openings 240 and accommodate some axial misalignment between the tool and the adapter 228, while minimizing any angular misalignment and backlash between the rotatable drivers 234 and the rotatable receiving elements 418. Additionally, the interaction between pins 422 and openings 240 helps restrain the robotic surgical tool 101 in the engaged position with the adapter 228 until the release levers 416 along the sides of the housing 401 push on the floating plate 236 axially from the interface so as to release the tool 101.

When disposed in a first axial position (away from the tool side 230) the rotatable drivers are free to rotate without angular limitation. The one or more rotatable drivers 234 may rotate clockwise or counter-clockwise to further actuate the systems and tools of the robotic surgical instruments 101. However, as the rotatable drivers move axially toward the tool side 230, tabs (extending radially from the rotatable drivers) may laterally engage detents on the floating plates so as to limit the angular rotation of the rotatable drivers about their axes. This limited rotation can be used to help engage the rotatable drivers the rotating members of the tool as the pins 422 may push the rotatable bodies into the limited rotation position until the pins are aligned with (and slide into) the openings 240 in the rotatable drivers.

While rotatable drivers 234 are described here, other types of drivers or actuators may be provided in the adapter 228 to actuate systems or tools of the robotic surgical instruments 101. The adapter 228 further includes terminals of an electrical connector 242 to couple to electrical contacts or pins 424 of surgical instruments 101 to make an electrical connection as well.

The mounting of robotic surgical tool 101A to the adapter 228 generally includes inserting the tip or distal end of the shaft or hollow tube of the robotic surgical tool through a cannula (not shown) and sliding the interface base 412 into engagement with the adapter 228, as illustrated in FIG. 2C. A lip 232 on the tool side 230 of the adaptor 228 slideably receives the laterally extending portions of the interface base 412 of the robotic surgical tool. A catch 244 of adapter 228 may latch onto the back end of the interface base 412 to hold the tool 101A in position. The protrusions or pins 422 extending from the one or more rotatable members 418 of the robotic surgical tool couple into the holes 240A-240B (generally referred to as holes or openings 240) in the rotatable drivers 234 of the adapter 228.

The range of motion of the rotatable receiving elements 418 in the robotic surgical tool may be limited. To complete the mechanical coupling between the rotatable drivers of the adapter and the rotatable receiving elements 418, the operator O at the surgical master control console 150 may turn the rotatable drivers in one direction from center, turn the rotatable drivers in a second direction opposite the first, and then return the rotatable drivers to center. Further, to ensure that the pins 422 enter openings 240 of rotatable drivers adapter 228, the adapter 228 and tool 101A mounted thereto may be moved together. The adapter 228 and tool 101A mounted thereto may be moved to an initial position so that the tip or distal end of the shaft or hollow tube is disposed within a cannula (not shown).

To dismount and remove the robotic surgical tool 101A, the release levers 416 may be squeezed pushing out on the mountable housing 401 to release the pins 422 from the holes 240 and the catch 244 from the back end of the interface base. The mountable housing 401 is then pulled up to slide the interface base 412 up and out from the adapter 228. The mountable housing 401 is continually pulled up to remove the tip or distal end of the shaft or hollow tube out from the cannula 219. After the robotic surgical tool 101A is dismounted, another robotic surgical tool may be mounted in its place, including a new or freshly sterilized electrosurgical robotic tool 400.

As previously discussed, the robotic surgical tool 101A may include one or more integrated circuits 426 to identify the type of robotic surgical tool coupled to the robotic arm, such that it may be properly controlled by the master control console 150. However, the robotic surgical system may determine whether or not the robotic surgical tool is compatible or not, prior to its use.

The system verifies that the tool is of the type which may be used with the robotic surgical system 100. The one or more integrated circuits 426 may signal to the computer 151 in the master control console 150 data regarding compatibility and tool-type to determine compatibility as well as control information. One of the integrated circuits 426 may include a non-volatile memory to store and read out data regarding system compatibility, the tool-type and the control information. In an exemplary embodiment, the data read from the memory includes a character string indicating tool compatibility with the robotic surgical system 100. Additionally, the data from the tool memory will often include a tool-type to signal to the master control console how it is to be controlled. In some cases, the data will also include tool calibration information. The data may be provided in response to a request signal from the computer 151.

Tool-type data will generally indicate what kind of tool has been attached in a tool change operation. The tool-type data may include information on wrist axis geometries, tool strengths, grip force, the range of motion of each joint, singularities in the joint motion space, the maximum force to be applied via the rotatable receiving elements, the tool transmission system characteristics including information regarding the coupling of rotatable receiving elements to actuation or articulation of a system within the robotic surgical instrument.

For example, the tool-type data might indicate that an electrosurgical robotic instrument 101A has been mounted to the robotic arm or not. Relevant to energy activation of an electrosurgical instrument, additional tool type data related to primary and/or secondary energy sub-features may further be stored. For example, energy sub-features may include what type of electrosurgical energy the tool may receive (e.g., bipolar or monopolar cutting & monopolar coagulating), maximum peak energy, minimum harmonic energy frequency, maximum harmonic energy frequency, and whether or not a laser is also provided for cutting. As new energy or other types of modalities are introduced for robotic surgical tools, its tool-type data can be readily stored and communicated to the robotic surgical system so that the system can adaptively control remote controllable equipment and multiple types of robotic surgical tools mounted to robotic arms of the robotic surgical system.

Instead of storing all of the tool-type data in the one or more integrated circuits 426, most of the tool-type data may optionally be stored in memory or a hard drive of the computer 151 in the robotic surgical system 100. An identifier may be stored in the one or more integrated circuits 426 to signal the computer 151 to read the relevant portions of data in a look up table store in the memory or the hard drive of the computer. The tool-type data in the look-up table may be loaded into a memory of computer 151 by the manufacturer of the robotic surgical system 100. The look-up table may be stored in a flash memory, EEPROM, or other type of non-volatile memory. As a new tool-type is provided, the manufacturer can revise the look-up table to accommodate the new tool-specific information. It should be recognized that the use of tools which are not compatible with the robotic surgery system, for example, which do not have the appropriate tool-type data in an information table, could result in inadequate robotic control over the robotic surgical tool by the computer 151 and the operator O.

In addition to the tool-type data, tool specific information may be stored in the integrated circuit 426, such as for reconfiguring the programming of computer 151 to control the tool. There may be calibration information, such an offset, to correct a misalignment in the robotic surgical tool. The calibration information may be factored into the overall control of the robotic surgical tool. The storing of such calibration information can be used to overcome minor mechanical inconsistencies between tools of a single type. For example, the tool-type data including the tool-specific data may be used to generate appropriate coordinate transformations and servo drive signals to manipulate the robotic arm and rotate the rotatable drivers 234. In this case, the integrated circuit 426 includes the information to set up the control system to drive the end effectors in the tool to have a maximum joint torque setting so that the jaws of a robotic gripping tool or a robotic electrosurgical tool can clamp to tissue with a maximum force.

Additionally, some robotic surgical tools have a limited life span. Tool life and cumulative tool use information may also be stored on the tool memory and used by the computer to determine if the tool is still safe for use. Total tool life may be measured by clock time, by procedure, by the number of times the tool has been loaded onto a holder, and in other ways specific to the type of tool. Tool life data is preferably stored in the memory of the tool using an irreversible writing process.

Master Control Console (Surgeon's Console)

Figure 3A:
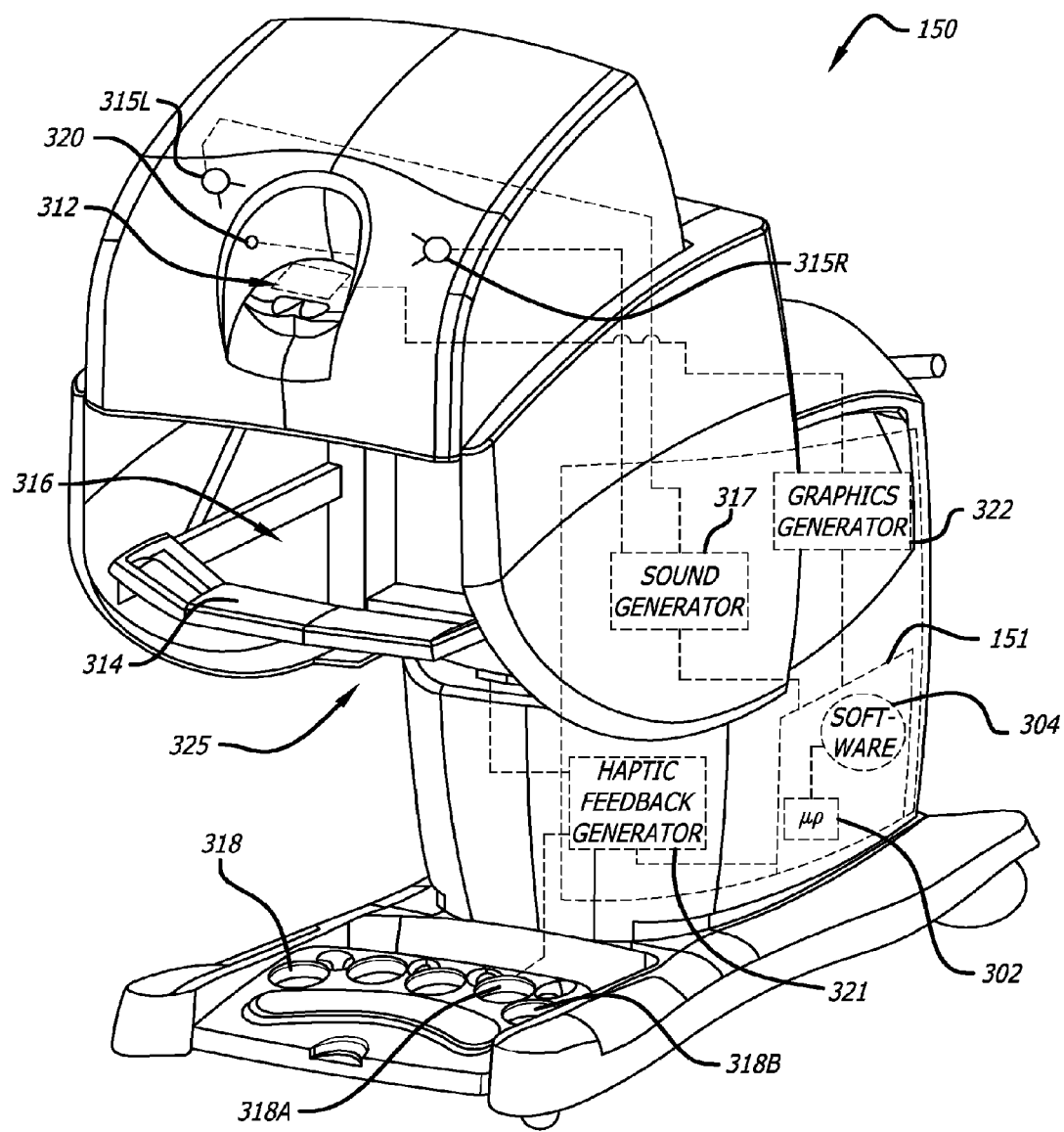
FIG. 3A is a perspective view of a robotic surgical master control console (surgeons console).

Referring now to FIG. 3A, a perspective view of the robotic surgical master control console 150,150A is illustrated. The master control console 150,150A may also be referred to as the surgeon's console. The master control console 150 generates the control signals to control surgical tools (e.g., the electrosurgical robotic instruments) in a surgical site and medical equipment that supports the surgical tools (e.g., electrosurgical generators).

The master control console 150 of the robotic surgical system 100 includes a binocular or stereo viewer 312, an arm-rest 314, a microphone 315, a pair of master controllers 925L,925R (generally referenced by 325) for end effector input control, wrist input control, and arm input control within a workspace 316, one or more speakers 315L,315R, and foot pedals 318 (including foot pedals 318A-318B), and a viewing sensor 320.

In one embodiment of the invention, the master control console 150 further includes an integrated computer 151. In another embodiment of the invention, as shown in FIG. 1B, the computer may be distributed from the master control console as a computer 151B that is an element of the central control cart 150B. In either case, the computer 151,151B may include one or microprocessors 302 to execute instructions and a storage device 304 to store software with executable instructions that may be used to generate control signals to control the robotic surgical system 100. The computer 151,151B may further include a sound generator 317 coupled to the microprocessors 302 and one or more speakers (left speaker 315L, right speaker 315R) to generate audible sounds; a haptic/tactile feedback generator 321 coupled to the microprocessors 302 and one or more vibrating devices at the master controls, the arm rest, and/or the foot pedals to generate vibrations; a graphics controller/generator 322 coupled to the microprocessors 302 and the stereo viewer 312 to generate a graphical user interface (GUI) and fuse the GUI data together with frames of camera image data of a surgical site for display on the display devices of the stereo viewer 312.

Figure 4:
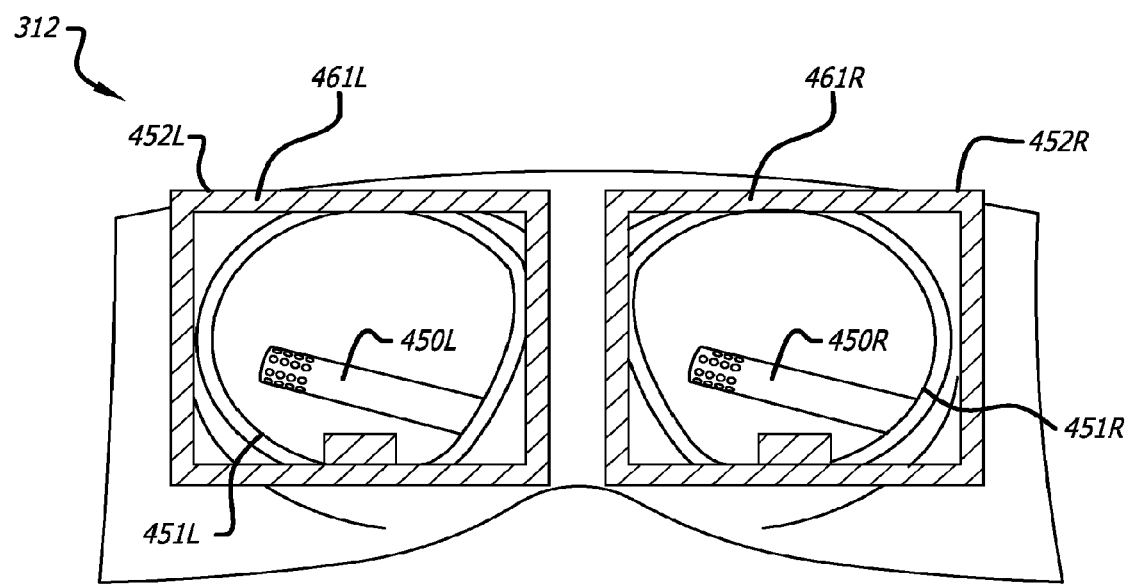
FIG. 4 is a perspective view of the stereo viewer of the master control console of FIG. 3A illustrating a graphical user interface overlaid onto video images of a surgical site.

The viewer 312 has at least one display where images of a surgical site may be viewed to perform minimally invasive surgery. In a preferred embodiment of the invention, the viewer 312 is a stereo viewer with left and right display devices 452L,452R as illustrated in FIG. 4. FIG. 4 illustrates a perspective view of the stereo viewer 312 of the master control console 150,150A. To provide a three-dimensional perspective, the viewer 312 includes stereo images for each eye including a left image 450L and a right image 450R of the surgical site including any robotic surgical tools respectively in a left viewfinder 451L and a right viewfinder 451R. The images 450L and 450R in the viewfinders are provided by the left display device 452L and a right display device 452R, respectively. The display devices 452L,452R may optionally be pairs of cathode ray tube (CRT) monitors, liquid crystal displays (LCDs), or other type of image display devices (e.g., plasma, digital light projection, etc.). In the preferred embodiment of the invention, the images are provided in color by a pair of color display devices 452L, 452R; such as color CRTs or color LCDs. A graphical user interface may be displayed like borders 461L,461R around or near edges of each of the display devices 452L,452R.

Referring now to FIGS. 3A-3C and FIG. 9, a left master controller 905L and a right master controller 905R (including master grip 325) in the workspace 316 can be used to generate control signals for the patient side cart 152 to control the robotic arms and the surgical tools mounted thereto. The left master controller 905L and the right master controller 905R are positioned in the workspace 316 disposed beyond the arm support 314 and below the viewer 312.

When using the master control console 150,150A, the operator O (surgeon or user) typically sits in a chair, moves his or her head into alignment with the viewer 312, and couples his/her fingers to the master grips 325 of left master controller 905L and the right master controller 905R, one in each hand, while resting their forearms against the arm rest 314. This allows the master grips 325 of the left master controller 905L and the right master controller 905R to be moved easily in the control space 316 in both position and orientation to generate control signals.

Additionally, the operator O can use his feet to control the foot-pedals to change the configuration of the surgical system and generate additional control signals to control the robotic surgical instruments or other medical equipment coupled to the system.

To ensure that the operator is viewing the surgical site when controlling the robotic surgical tools 101, the master control console 150 may include the viewing sensor 320 disposed adjacent the binocular display 312. When the system operator aligns his or her eyes with the binocular eye pieces of the display 312 to view a stereoscopic image of the surgical worksite, the operator's head sets off the viewing sensor 320 to enable the control of the robotic surgical tools 101. When the operator's head is removed the area of the display 312, the viewing sensor 320 can disable or stop generating new control signals in response to movements of the master grips in order to hold the state of the robotic surgical tools.

The computer 151 with its microprocessors 302 interprets movements and actuation of the left master controller 905L and the right master controller 905R (and other inputs from the operator O or other personnel) to generate control signals to control the robotic surgical instruments 101 in the surgical worksite. In one embodiment of the invention, the computer 151 and the viewer 312 map the surgical worksite into the controller workspace 316 so it feels and appears to the operator that the left master controller 905L and the right master controller 905R are working over a surgical worksite.

Master Controllers with Control Input Grips

Figure 9:
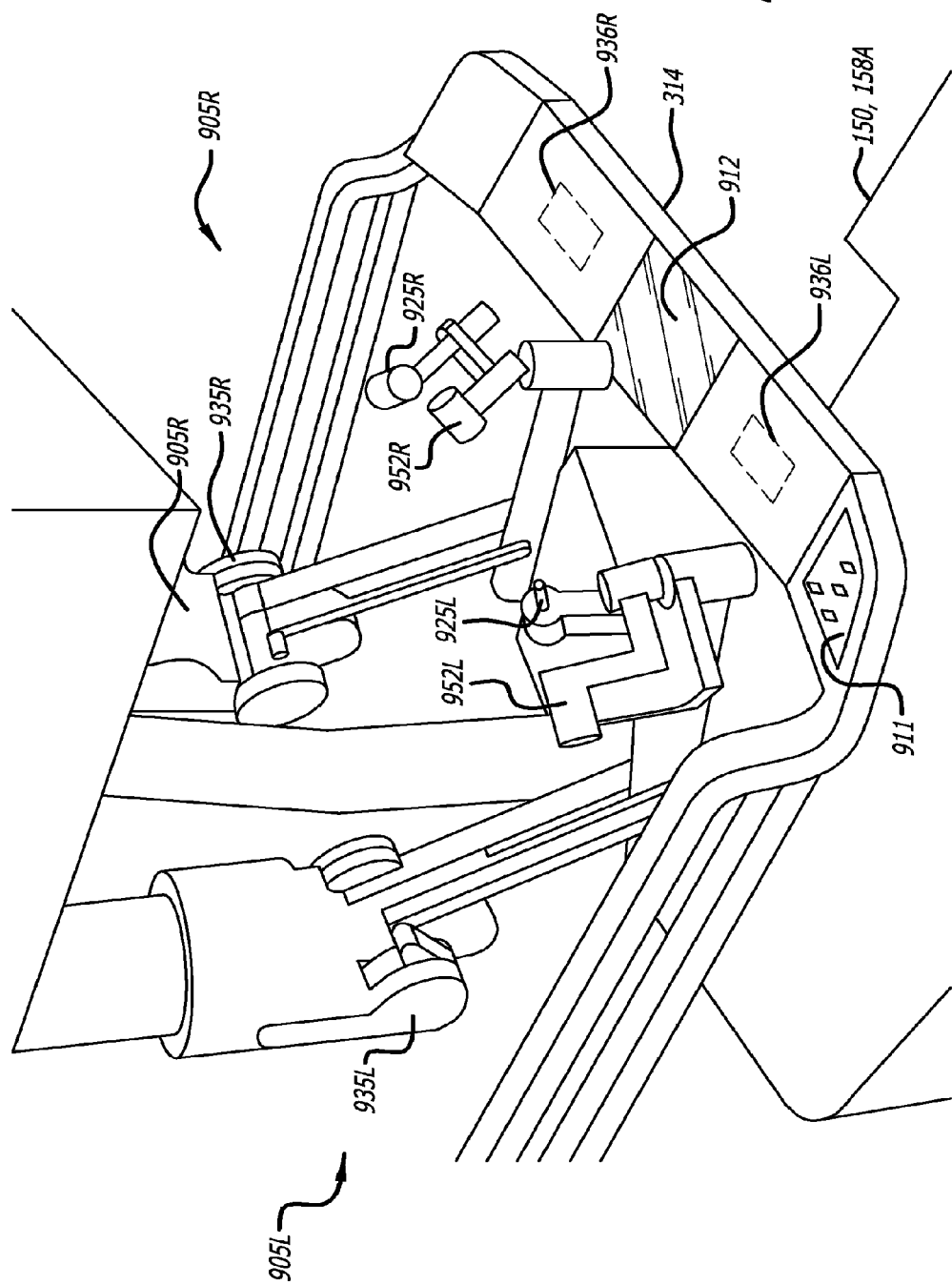
FIG. 9 is a perspective view of a workspace in the surgeon's console showing a left master controller and a right master controller.

Referring momentarily now to FIG. 9, a perspective view of the controller workspace 316 at the surgeon's console 150, 150A is illustrated. The surgeon's console 150,150A has a left master controller 905L and a right master controller 905R. The left master controller 905L includes a left control input arm 935L, a left control input wrist 952L and a left control input grip 925L. The right master controller 905R includes a right control input arm 935R, a right control input wrist 952R and a right control input grip 925R.

Referring now to FIG. 3B, a perspective view of a control input wrist 352 representative of the left control input wrist 952L and the right control input wrist 952R is illustrated. The master controllers 905L,905R at the surgeons console include a control input grip or master grip 325 and a control input wrist 352 coupled together to a control arm (see control input arms 935L,935R in FIG. 9). The control input wrist 352 is a gimbaled device that pivotally supports the master grip 325 of the master control console 150 to generate control signals that are used to control the robotic surgical manipulator 152 and the robotic surgical tools 101, including electrosurgical robotic tools 101A,101B. A pair of control input wrists 352 for the left and right master controllers are supported by a pair of control input arms (not shown in FIG. 3B) in the workspace 316 of the master control console 150, 150A. The control input wrist 352 includes first, second, and third gimbal members 362, 364, and 366. The third gimbal member 366 is rotationally coupled to a control input arm (not shown) of the master control console 150, 150A.

The master grip 325 includes a tubular support structure 351, a first grip 350A, and a second grip 350B. The first grip and the second grip are supported at one end by the structure 351. The master grip 325 can be rotated about axis G illustrated in FIGS. 3B-3C. The grips 350A, 350B can be squeezed or pinched together about the tubular structure 351. The "pinching" or grasping degree of freedom in the grips is indicated by arrows Ha,Hb in FIG. 3B and arrows H in FIG. 3C.

The master grip 325 is rotatably supported by the first gimbal member 362 by means of a rotational joint 356g. The first gimbal member 362 is in turn, rotatably supported by the second gimbal member 364 by means of the rotational joint 356f. Similarly, the second gimbal member 364 is rotatably supported by the third gimbal member 366 using a rotational joint 356d. In this manner, the control wrist allows the master grip 325 to be moved and oriented in the workspace 316 using three degrees of freedom.

The movements in the gimbals of the control wrist 352 to reorient the master grip in space can be translated into control signals to control the robotic surgical manipulator 152 and the robotic surgical tools 101.

The movements in the grips 350A,350B of the master grip 325 can also be translated into control signals to control the robotic surgical manipulator 152 and the robotic surgical tools 101. In particular, the squeezing motion of the master grips 350A,350B over their freedom of movement indicated by arrows Ha,Hb or H, may be used to control the end effectors of the robotic surgical tools.

To sense the movements in the master grip 325 and generate controls signals, sensors can be mounted in the handle 325 as well as the gimbal member 362 of the control input wrist 352. Exemplary sensors may be a Hall effect transducer, a potentiometer, an encoder, or the like.

Figure 3C:
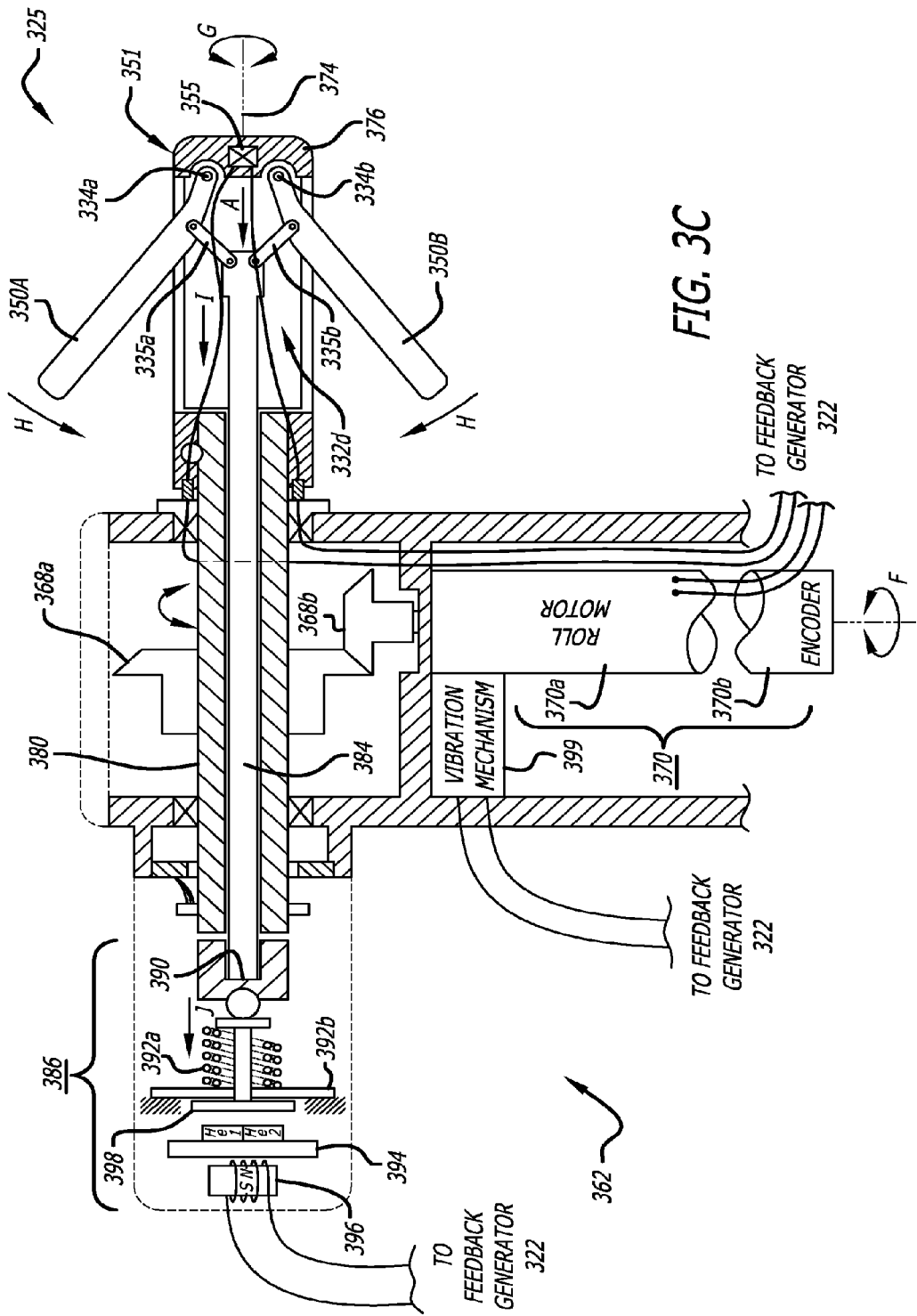
FIG. 3C is a cross-sectional view schematically illustrating the master grip control handle (also referred to as a master grip control input) pivotally coupled to the control input wrist of FIG. 3B with elements coupled to the feedback generator to provide haptic/tactile user feedback.

Referring now to FIG. 3C, a cross-sectional view of the master grip 325 and gimbal member 362 of the control input wrist 352 is illustrated. FIG. 3C provides an example as to how the master grip 325 can be mounted to the control input wrist 352 to sense the gripping and rotation of the handle to control robotic surgical tools 101.

As illustrated in FIG. 3C, the exemplary gimbal member 362 includes beveled gears 368a, 368b which can couple the rotational motion of the master grip 325 to a roll sensor 370. The roll sensor 370 may use a potentiometer or encoder 370b included in a roll motor 370a to sense the rotation. Alternatively, a separate roll sensor, such as a potentiometer, may be directly coupled to the shaft 380 to sense the rotation of the master grip. In any case, a roll sensor senses the roll motion of the master grip 325 and generates control signals in response thereto to control the robotic surgical tools 101.

To sense a squeezing motion in the grips 350A,350B of the master grip 325, a remote sensing assembly 386 may be included by the gimbal member 362. The first and second grips 350A,350B are adapted to be squeezed together by a hand of an operator O so as to define a variable grip separation. The grip separation may be determined as a function of a variable grip angle with an axis or as a function of a variable grip separation distance, or the like. Alternative handle actuations, such as movement of a thumbwheel or knob may also be provided in the handle to control the robotic surgical instruments 101.

In the exemplary embodiment, the remote sensor assembly 386 includes a circuit board 394 on which a first and a second Hall effect sensors, HE1, HE2 are mounted. A magnet 396 is disposed distally beyond the circuit board 394 and the Hall effect sensors. A magnetic mass 398 is axially coupled to the proximally oriented surface 390 of a push rod 384. Thus, the magnetic mass 398 moves (as shown by Arrow J) with the push rod 384 and varies the magnetic field at the Hall effect sensors in response actuation of the grips 350A,350B.

To translate the squeezing action of the grips 350A,350B to the sensor 386, the gimbal member 362 includes a push rod 384 within the tubular handle structure 351. Each of the grips 350A, 350B pivot about a respective pivot 334a, 334b in the tubular handle structure 351. Urging links 335a, 335b respectively couple between the grips 350A,350B and a first end of the push rod 384. The squeezing action of the grips 350A,350B is translated into a linear motion on the push rod 384 by means of urging links 335a,335b as shown by arrow A in FIG. 3C. A second end of the push rod 384 couples to the sensor 386. As discussed previously, the magnetic mass 398 is axially coupled to the surface 390 of the push rod 384 in order to sense the linear motion in the push rod and the squeezing motion of the grips 350A,350B.

A biasing mechanism such as spring 392 applies a force against the squeezing motion of the grips to return them to full open when the grips are released. The biasing spring 392 may be a linear or non-linear elastic device biasing against the depression of grips 350A, 350B, e.g., a single or multiple element assembly including springs or other elastic members. For example, spring 392 may comprise a concentric dual spring assembly whereby one spring provides a "softer" bias response as the grips 350A, 350B are initially depressed, and a second spring provides a superimposed "firm" bias response as the grips 350A, 350B approach a fully depressed state. Such a non-linear bias may provide a pseudo force-feedback to the operator.

The master grip may be an ideal place to provide haptic/tactile feedback to a user's hands through a vibrating device or mechanism. The magnet 396 of the master grip may be an electro-magnet under control of the haptic/tactile feedback generator as a vibrating device to generate vibrations in the master grip for haptic/tactile user feedback. Alternatively, another type of vibrating device may be an element of the master grip and controlled by the haptic/tactile feedback generator. The control input wrist 325 may have such a vibrating device or mechanism 399 coupled to the haptic/tactile feedback generator 321 to generate vibrations in the control input wrist that may be felt by a user. A vibrating device 355 coupled to the feedback generator 321 may be a part of the master grip near where the user's fingers make contact. Alternatively, pre-existing electric motors in each control input wrist of the master controllers may be used to generate vibrations. A feedback signal may cause the motor to alternatively rotate back and forth over a small arc to generate a vibration. For example, roll motor 370a may be coupled to the haptic/tactile feedback generator 321 and rotated back and forth over one or a couple of segments of the encoder 370b. U.S. Pat. No. 6,522,906 issued to Salisbury, Jr., et al. on Feb. 18, 2003; and U.S. Pat. No. 6,493,608 issued to Niemeyer on Dec. 10, 2002 also describe using haptic feedback at the master controllers.

Referring now back to FIG. 9, an arm-support or arm-rest 314 in the surgeon's console 150,150A may include a left vibrating feedback mechanism 936L and a right vibrating feedback mechanism 736R positioned in the arm wrest to be under an area where a surgeon (user or operator O) may rest his left and right forearms. The left vibrating feedback mechanism 936L and the right vibrating feedback mechanism 736R couple to the haptic/tactile feedback generator 321 to receive a left feedback signal and a right feedback signal. In response to the feedback signal from the haptic/tactile feedback generator 321, either the left vibrating feedback mechanism 936L or the right vibrating feedback mechanism 736R can generate vibrations in the arm-rest 314 that may be felt by a user's forearm resting on the arm-rest.

It should be noted that a wide variety of vibration devices or mechanisms may be used to generate vibrations that the operator O (user, surgeon) may feel when operating the controls at the surgeons' console 150,150A.

Pedal System for Integrated Control

Referring now to FIG. 7A, a surgical console pedal system 700 is illustrated in a top view. The pedal system 700 includes a movable pedal tray 702, a lower left pedal assembly 704L, a lower right pedal assembly 704R, a left vertical switch pedal assembly 706L, a right vertical switch pedal assembly 706R, an upper level pedal assembly 708L, and an upper right level pedal assembly 708R. The pedal system 700 may include a drive assembly to move the moveable pedal tray 702 over a floor. The pedal system 700 may further include a lift assembly to raise the moveable pedal tray above the floor when transporting the surgeon console and lower the pedal tray when its pedals are ready to be used by a user.

Each of the pedal assemblies may be assigned by the robotic surgical system to control medical equipment that may couple to one or more surgical tools. The functionality controlled by each pedal may be context sensitive and switch depending upon the type of surgical tools being controlled. In one embodiment, the pedal system is assigned to control electrosurgical tools in response to one or more electrosurgical tools being mounted to one or more of the robotic arms respectively. The robotic surgical system may sense that one or more electrosurgical tools are mounted to one or more of the robotic arms.

The movable pedal tray 702 has a base portion 711 and an upper tier or terrace portion 712 coupled to and elevated above the base portion 711. The pedal tray 702 has a center chair cut-out or opening 710 in a front edge of the base portion 711 so that a wheel of a chair may roll on the floor therein to appropriately adjust the position of the user at the surgeon's console.

The lower left pedal assembly 704L and the lower right pedal assembly 704R are positioned within the base portion 711 of the pedal tray. The upper left pedal assembly 708L and the upper right pedal assembly 708R are positioned within the upper tier or terrace portion 712 slightly elevated above the lower left pedal assembly 704L and the lower right pedal assembly 704R. The upper tier or terrace portion 712 may be U-like shaped to receive the left vertical switch pedal assembly 706L in a left side and the right vertical switch pedal assembly 706R in a right side.

The left vertical switch pedal assembly 706L is situated near the lower left pedal assembly 704L so that a user's left foot may move horizontally to toggle the switch. The right vertical switch pedal assembly 706R is located near the lower right pedal assembly 704R so that a user's right foot may toggle the switch by horizontal movement. The pedals 704L-704R and 708L-708R are horizontal switch pedals that may be activated when a users foot moves vertically downward.

Figure 8:
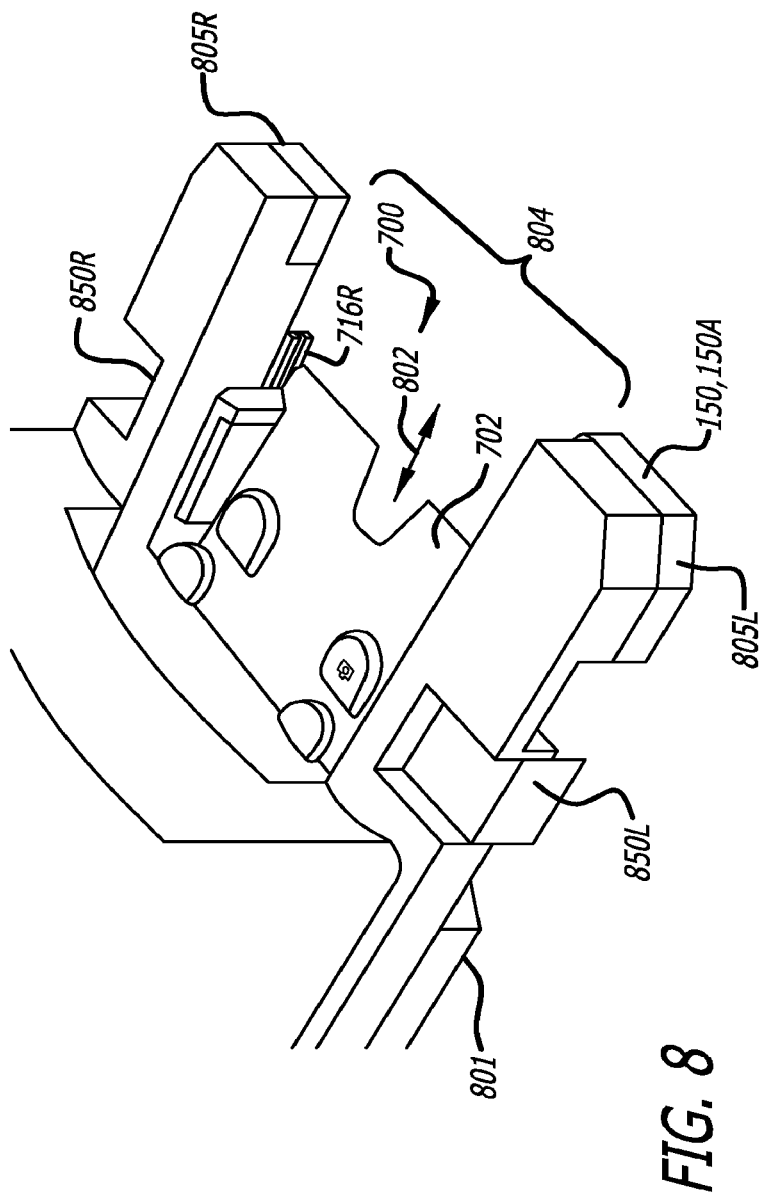
FIG. 8 is a perspective view of the integrated pedal system assembled to the surgeon's control console.

Referring momentarily to FIG. 8, the surgeon's console pedal system 700 is shown moveably coupled to the surgeon's console 150, 150A. The surgeon's console pedal system 700 is movable within an opening 804 of the base 801 of the surgeon's console 150, 150A as shown by the arrow 802. The pedal tray 702 moves inward and outward over the floor within the opening 804 of the surgeon's console between left and right pontoons 805L,805R of the base 801 of the surgeon's console. This is so the pedal positions can be adjusted to custom fit a size of the surgeon seated at a chair near the surgeon's console. Digital numbers representing the position of the pedal tray 702 with respect to the console 150,150A may be stored in a storage device for later recall by the surgeon. The left and right pontoons 805L,805R include left and right brake pedals 850L,850R, each a latchable pedal, that may be used to lock the casters (not shown) of the surgeons console to keep it stationary.

Figure 7C:
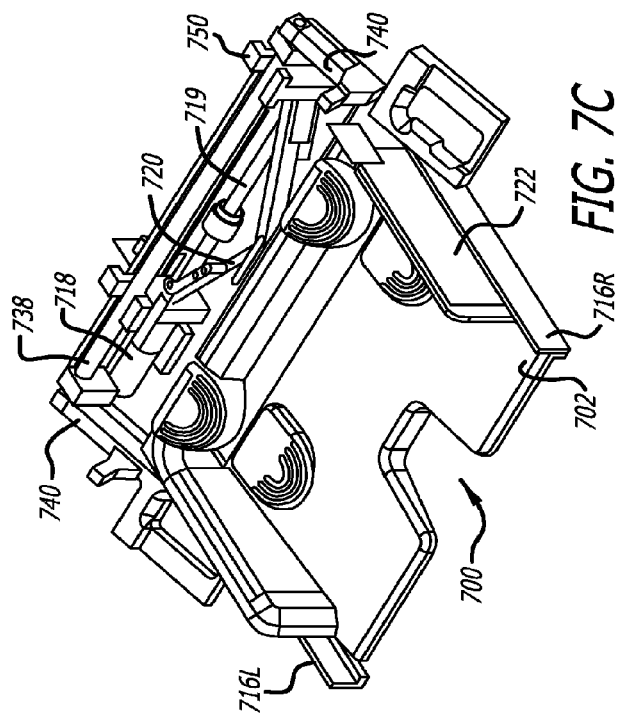
Figure 7D:
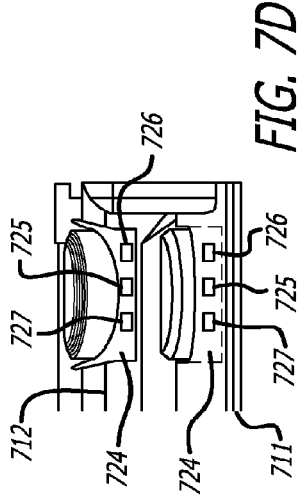
Figure 7B:
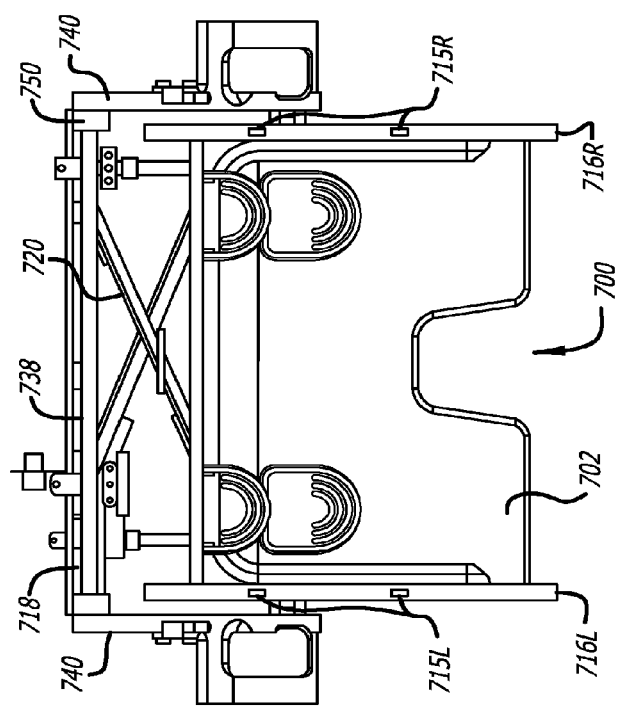
Figure 7E:
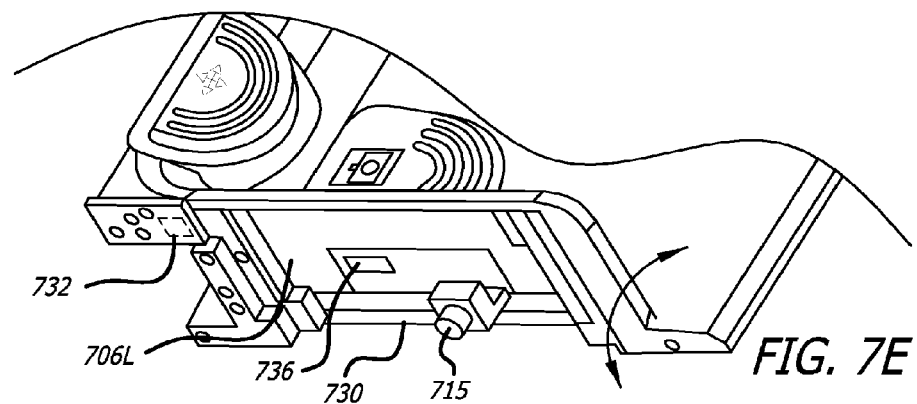
Figure 7F:
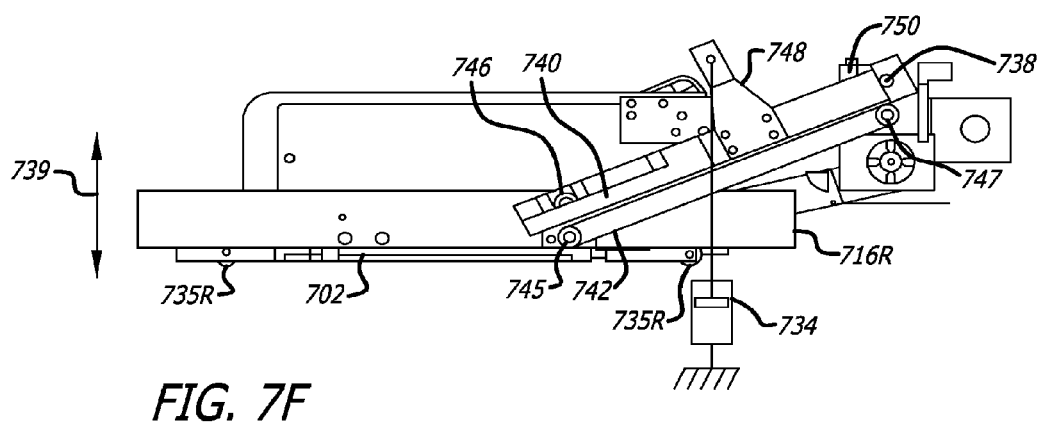

Referring now to FIGS. 7B and 7F, a top view and a side view of the pedal system 700 are respectively illustrated. The pedal system 700 includes a pair of left rollers 715L rotatably coupled to a left side and a pair of right rollers 715R rotatably coupled to right side of the moveable pedal tray. In one embodiment of the invention, the pair of left rollers 715L and the pair of right rollers 715R respectively roll along a left lift/guide rail 716L and a right lift/guide rail 716R to guide the pedal tray within the opening 804 of the base 801 when raised above the floor for transporting or moving the surgeon's console. In another embodiment of the invention, the pair of left rollers 715L and the pair of right rollers 715R respectively roll along the left guide rail 716L and the right guide rail 716R to guide the pedal tray within the opening 804 of the base 801 when the pedal tray is near or configured to roll along the floor. Otherwise when the pedal tray is lowered to the floor rolling upon rollers (e.g., see rollers 735R in FIG. 7F), the left guide rail 716L and the right guide rail 716R are sufficiently low so that the rollers the pair of left rollers 715L and the pair of right rollers 715R need not roll along the left guide rail 716L and the right guide rail 716R. At the bottom, the pedal tray includes a pair of rollers 735R pivotally coupled to the right side of the pedal tray and a similar pair of rollers pivotally coupled to the left side of the pedal tray to roll along the floor and move the pedal tray when lowered with the castor brakes of the surgeons console are set.

As mentioned previously, the pedal tray 702 may be vertically raised above the floor and lowered to the floor as indicated by the arrowhead 739. The lift mechanism or assembly of the pedal system 700 includes a linkage on each side pivotally coupled between the lift/guide rails 716L, 716R, each other and a frame 750 of a drive assembly of the pedal system. The lift assembly of the pedal system further includes a pair of springs 734 each with an end coupled to the linkage in each side to apply a force and raise the pedal tray above the floor. Each spring 734 has an opposite end coupled to the surgeon's console schematically indicated as a ground link in FIG. 7F. In one embodiment, each spring 734 may be coupled to the base 801 of the surgeon's console to push up on the pedal tray to raise it above the floor. In another embodiment, each spring may be coupled to the base 801 to pull up on the pedal tray to raise it above the floor. In one embodiment of the invention the spring 734 is a gas spring.

The springs 734 pre-load the linkage to raise the pedal tray above the floor within the opening. To lower the pedal tray 702, a user presses down on either brake pedal 850L, 850R shown in FIG. 8 to press down on the linkage and overcome the force applied by the springs 734. Either brake pedal can be latched in place to hold the pedal tray down against the force of the springs 734. A torsion bar 738 coupled between the linkage on each side transfers torque from one side to the other to lower each side of the tray together, if either brake pedal 850L,850R is pressed. To raise the pedal tray 702, both brake pedals 850L,850R are unlatched so that the springs 734 coupled to lift rails can force up and raise the pedal tray 702 above the floor.

The linkage in each side of the pedal system allows the pedal tray to be raised and lowered substantially in parallel to the floor. The linkage in each side of the pedal system includes an upper link 740 and a lower link 742 to form a four bar or parallelogram linkage with the lift/guide rail 716R,716L and the frame of the drive assembly coupled to base providing the other links. The upper link 740 pivots with the torsion bar 738 near one end. An opposite end of the upper link 740 pivots around a pivotal shaft 746. The lower link 742 pivots near one end about a pivotal shaft 746. At an opposite end, the lower link 742 pivots about a pivotal shaft 747. The pivotal shafts 745-746 on each side are coupled to lift/guide rails 716R,716L of each side of the pedal system 700. The pivotal shaft 747 may be coupled to the frame 750 of the back drive assembly.

To raise the pedal tray, each side of the linkage is preloaded to be raised up by the springs 734 mounted between the upper link 740 and the base (or ground) of the surgeon's console. A pick up bracket 748 couples between an end of the gas spring 734 and near a midpoint of the upper link 740 to couple the spring 734 to the linkage. The preloaded force of the spring applied to the linkage tries to keep the rails 716R,715L (and therefore the foot pedal tray 702) in the raised position. A user presses down on either brake pedal 850L,850R to drive the upper link 740 down as well, lowering both the linkage and the foot pedal tray 702. If a user pushes sufficiently far enough, either brake pedal 850R,850L latches in a down position to hold the linkage and the foot pedal tray in the lowered position so that it can roll over the floor. In the down or lowered position, the rollers 735R and the fool pedal tray can rest on the floor without its wheels 715L,715R resting on the lift/guide rails 716L,716R.

The pivot point for the upper link 740 near the drive assembly is the torsion bar 738. The torsion bar extends across to the mirrored linkage assembly in the other side. FIGS. 7B and 7C illustrate the torsion bar 738 coupled between the upper links 740 in each side. For this reason, the two linkages and rails in each side move up and down together, even if only one side's brake pedal 850L or 850R is pressed. When the latches of the brake pedals 850L,850R are released, the brake pedals can move up to their raised position. The springs 734 lift the linkage in each side up above the floor along with the lift/guide rails. The left and right lift/guide rails 716L,716R engage the left and right rollers 715L,716R to lift the foot pedal tray 702 to its raised position for travel.

To move the pedal tray 702 horizontally within the opening 804 along the floor when lowered or within the guide rails, the pedal system 700 further includes a drive mechanism or drive assembly. The drive assembly of the pedal system 700 includes a tray motor 708 coupled to a frame 750 and a scissor arm assembly 720 coupled between the tray motor 708 and the pedal tray 702. The frame 750 is coupled to the base 801 of the surgeon's console. The tray motor 708 includes a rotatable shaft coupled to an end of a threaded drive rod 719 to apply a force to the moveable pedal tray 702. The threaded drive rod 719 is rotatably coupled to the base so that it can rotate in place. One end of a pair of cross arms of the scissor arm assembly 720 is threadingly and pivotally coupled to the threaded drive rod 719. An opposite end of the pair of cross arms of the scissor arm assembly 720 is pivotally coupled to a back side of the pedal tray 702. As the shaft of the tray motor 718 rotates in one direction, the threaded drive rod 719 rotates in that one direction so that the scissors arm assembly 720 opens and pushes out the pedal tray 702. As the shaft of the tray motor 718 rotates in an opposite direction, the threaded drive rod 719 rotates in the opposite direction so that the scissors arm assembly 720 closes and pulls in the pedal tray 702.

In FIG. 7C, a side perspective view of the pedal system 700 is illustrated. The left vertical switch pedal assembly 706L and the right vertical switch pedal assembly 706R are pivotally coupled to the left and right sides of the pedal tray. Each of the left vertical switch pedal 706L and the right vertical switch pedal 706R includes a vertical switch assembly 722. Each of the pedal assemblies may include a spring so as to be spring loaded so they are momentarily closed when pressed on by the users foot and then spring back to switch open when the users foot is removed.

Referring now to FIG. 7E, a cutaway view of the vertical switch assembly 722 is illustrated for each of the vertical switch pedals 706L-706R. The vertical switch assembly 722 includes a rod 730 coupled to the base of the pedal tray about which the pedal may pivot to open and close an electrical switch 732. The vertical switch assembly may further include a spring to push back on the pedal. Assuming a normally open switch, horizontal foot movement against the pedal causes it to pivot about the rod 730 to compress the spring and close the electrical switch 732. Releasing the foot pressure on the pedal allows the spring push back out, pivoting the pedal back to a normal position and opening the electrical switch.

Referring now to FIG. 7D, each of the horizontal pedal assemblies 704L-704R and 708L-708R are spring loaded and include a horizontal switch assembly 724. Each of the horizontal switch assembly 724 includes an electrical switch

725. The horizontal switch assembly may further include a spring to push back on the pedal. Assuming a normally open switch, vertical foot movement pressing down against the pedal causes the spring to compress and the electrical switch 732 to close. Releasing the foot pressure on the pedal causes the pedal to spring back and open the electrical switch 732.

Each of the horizontal switch assembly may further include a vibrating device 726 to provide haptic/tactile user feedback. Each of the horizontal switch assembly may further include a sensing device 727 to sense when a foot is over the pedal and ready to press down to close the switch and generate a control signal to control the robotic surgical system.

Each of the switches 725,732 activated by the pedal assemblies may be of different switch types, such as a toggle switch (toggling between opened and closed switch states), a normally open-momentarily closed switch, or a normally closed-momentarily open switch. Furthermore, the type of signal generated by the switch may be translated, encoded, or adapted to a proper voltage to control various types of medical equipment.

Ergonomic Control

Referring now FIG. 9, a perspective view of the person of the workspace 316 of the surgeon's console 150, 150A is illustrated. As mentioned previously, the pedal tray 702 of the pedal system at the surgeon's console moves so that the pedal positions are comfortably reached by the surgeon. For each surgeon, a desired saved pedal position can recalled and the pedal tray can be automatically adjusted to custom fit a size of the surgeon.

To initially control (and override the automated adjustments) the movement of the pedal tray 702 of the pedal system 700, as well as other ergonomic positions, the surgeon's console 150,150A includes an ergonomic control panel 911 next to the arm wrest 314. The ergonomic control panel 911 is better illustrated in FIG. 11A.

Figure 11A:
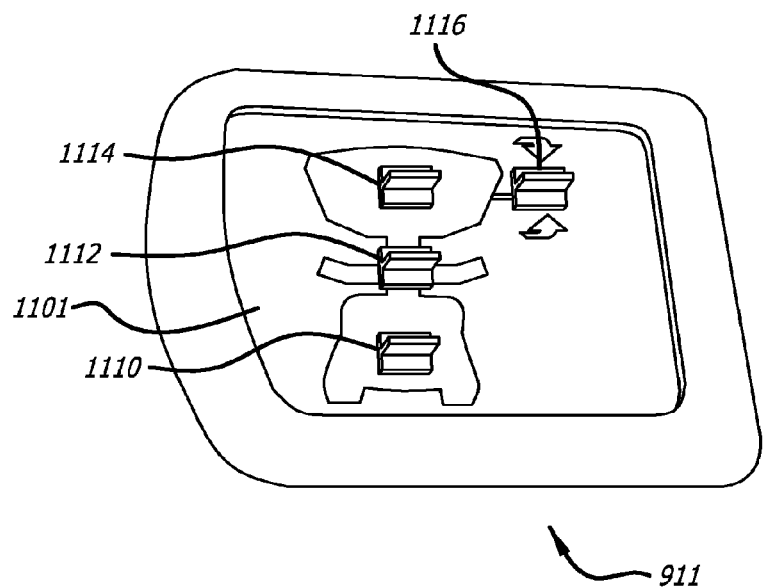
FIG. 11A is a magnified perspective view of the ergonomic control panel in the surgeon's console shown in FIG. 9.

Referring now to FIG. 11A, a magnified perspective view of the ergonomic control panel 911 is illustrated. The ergonomic control panel 911 includes a pedal tray adjustment toggle switch 1110, an arm-rest height adjustment toggle switch 1112, a display height adjustment toggle switch 1114, and a display angle adjustment toggle switch 1116. Each of these toggle switches may be moved up or down to energize a motor to change position settings. For example, the pedal tray adjustment toggle switch 1110 when pushed upward may turn on an electric motor to adjust the pedal tray inward. When the pedal tray adjustment toggle switch 1110 is pushed downward it may turn on the electric motor to adjust the pedal tray outward.

The switches 1110, 1112, 1114, and 1116 of the control panel 911 are positioned into a console map 1101 of the panel 911 with icons of the console in the background so that it is clear what function each has. The pedal tray adjustment toggle switch 1110 that moves the pedal tray 702 is located near feet icon of the console map to indicate position adjustments of the pedals. The arm-rest height adjustment toggle switch 1112 is located on an arm-rest icon to indicate height adjustments of the arm-rest. The display height adjustment toggle switch 1114 is located on a monitor icon to indicate height adjustments of the stereo display. The display angle adjustment toggle switch 1116 is located on an axis icon near the monitor icon to indicate angle adjustments of the monitor.

The ergonomic settings of the surgeon's console set by each of the toggle switches may be saved into a user account for each respective user. The information regarding the account may be stored in a storage device of the computer 151. Each user account, including the saved ergonomic adjustments, may be secured with a login identification ID and optionally a password.

Referring now back to FIG. 9, the surgeon's console 150,105A further includes a liquid crystal display (LCD) touchpad screen 912 mounted in the arm-rest 314 to access the user accounts. The LCD touchpad screen 912 is located near the center of the arm-rest 314 between positions where a surgeon's arms may wrest so that it may be viewable during surgery and avoid extraneous readings from the arms touching the touch screen.

Figure 11B:
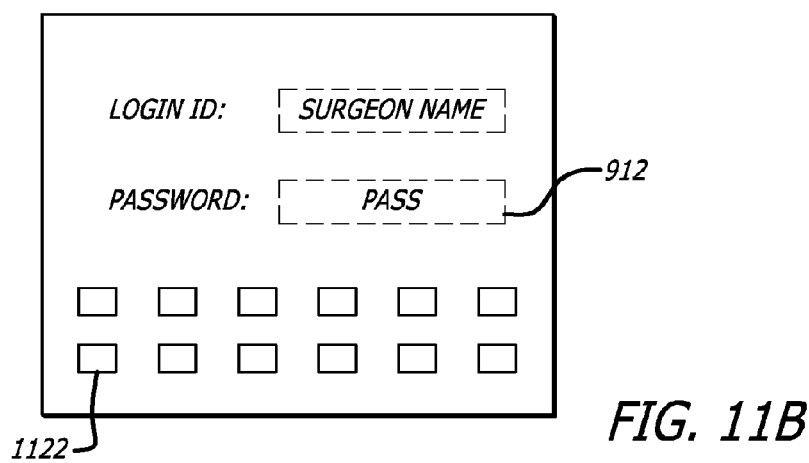
FIG. 11B is a top view of the liquid crystal display (LCD) touchpad screen in the surgeon's console shown in FIG. 9.

Referring now to FIG. 11B, a top view of the liquid crystal display (LCD) touchpad screen 912 is illustrated. The saved ergonomic setting for a user may be recalled by logging into the robotic surgical system through the use of the touchpad screen 912. A surgeon (user or operator O) may enter or select his or her login ID and optionally enter a password by means of a touch sensitive keypad 1122 of the touchpad screen 912. After a successful login to a user account, the system recalls the ergonomic settings, including the pedal tray adjustment setting, the arm-rest height adjustment setting, the display height setting, and display angle setting. The system then automatically readjusts the positions of the pedal tray, the arm-rest and the stereo display to those saved settings. For example, the position setting of the pedal tray 702 with respect to the console 150,150A is recalled from the storage device and automatically adjusted to that setting that is associated with the user account. If any of the settings are undesirable to the user, he can reset the adjustments for current use and then save the new settings upon logging out of the system for later recall.

Referring now back to FIG. 9, the position of the master controllers 905L and 905R may be adjusted to a desired position by a user without moving/controlling the robotic arms and robotic surgical tools. This is by selectively disengaging the master controllers from the slave controlled arms and tools, sometimes referred to as clutching. That is, the master controllers 905L and 905R can be clutched from the robotic arms and surgical tools to adjust their positions.

Previously, this may have been performed by pressing a pedal or a combination of pedals to clutch the master controllers. In this case, both of the master controllers were clutched. However, there are times when only one master controller need be clutched. This may be the case, for example, if only one needs to be repositioned. Alternatively, one of the master control arms may be used to control a mouse pointer (sometimes referred to as a masters as mice mode) to select items from an on-screen menu system in the graphical user interface for further control of the robotic surgical system and/or its surgical tools.

To further control different modes and independently adjust the positioning of the left master controller and the right master controller, the left master grip 925L and the right master grip 925R may each may include one or more switches.

Figure 10:
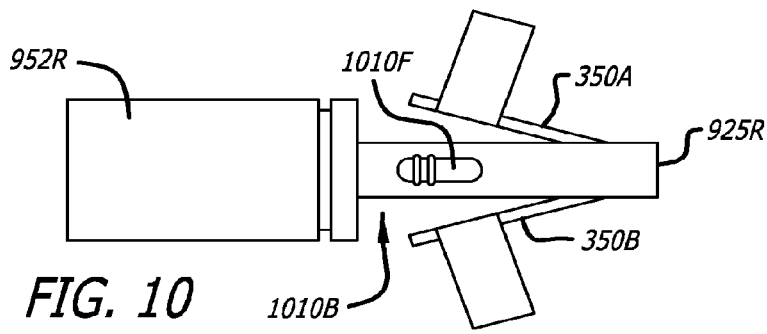
FIG. 10 is a magnified perspective view of the right master grip and right control input wrist of the right master controller shown in FIG. 9.

Referring now FIG. 10, a magnified perspective view of the right master grip 925R and right control input wrist 952R of the right master controller is illustrated. The right master grip 925R and right control input wrist 952R is also representative of the left master grip and left master wrist portion of the left master controller.

Each of the left master grip 925L and the right master grip 925R includes a front side switch 1010F and a back side switch 1010B that can be controlled by fingers of the user (surgeon, operator O). The front and back side switches on each master controller may be identical but read independently by the system. However, software may programmed to perform the same action in response to activation of either the front or back side switch. This permits a user to grasp the masters in different ways and still control a controllable feature with either of the front side switch 1010F and the back side switch 1010B of a respective master grip. Collectively, the front side switch 1010F and the back side switch 1010B of both master controllers may be referred to herein as a switch 1010.

In one embodiment of the invention, the switch 1010 is a slideable switch that can move from a closed position to an open position and back again. The switch slides along a tubular support structure 351 of the master control input grip 925R,925L. In one embodiment of the invention, the switch 1010 is not spring loaded so that it remains in whatever position is chosen by the user. In another embodiment of the invention, the switch 1010 is spring loaded, requiring the user to maintain pressure on the switch in one of the positions (open or closed), otherwise having it slide back to a normal position (closed or open) when the sliding pressure on the switch is released.

The switch 1010 of each master grip can be programmed to independently clutch each of the left master controller and right master controller from the respective slave controlled elements (left robotic arm/tool and right robotic arm/tool) of the patient side cart 152. After clutching the left or right master controller, the clutched master controller can be repositioned within the workspace so as to be in a better position to control the robotic surgical tool when the master controller is re-engaged (un-clutched) to control the respective slave controlled elements of the patient side cart 152. The master controller can be re-engaged by switching the switch back to normal control mode.

When clutched by the switch 1010, the clutched master controller also may be used as a multi-dimensional computer mouse moving in multiple dimensions over a multi-dimensional space displayed by a stereo viewer. In one case, the clutched master controller is used as a three-dimensional computer mouse moving in three dimensions over a three-dimensional space displayed by the stereo viewer. The user interface in that case may have certain three dimensional aspects such as described in U.S. patent application Ser. No. 12/189,615 entitled INTERACTIVE USER INTERFACES FOR ROBOTIC MINIMALLY INVASIVE SURGICAL SYSTEMS, filed on Aug. 11, 2008, by Simon DiMaio, for example, and incorporated herein by reference.

While the switches 1010 in each master controller can independently clutch each master controller, a clutch pedal or clutch pedal sequence may still be provided/used to jointly clutch both master controllers together, such as when the surgical procedure may be completed, for example. Furthermore, while one of the switches 1010 may be used to enter a masters-as-mice mode, the masters as mice mode may alternatively be entered by stepping on a foot pedal or by pressing a button on a touchpad interface, for example, Moreover, the functionality of the switches 1010 may be expanded. For example, the switches 1010 may be selectively used to activate an energy device with a user's hand, swap control from one slave arm to another, or activate a new feature. Furthermore, front and back switches 1010E-1010B may be programmed to perform different actions in response to varying contexts or user interface modes.

Electro Surgical Instruments

Robotic electrosurgical tools can be mounted to one or more of the robotic arms of the patient side cart of the robotic surgical system. Details of robotic electrosurgical tools are described in U.S. patent Nos. with filing dates and named inventor as follows U.S. Pat. No. 6,840,938, Dec. 21, 2001, Morley et al.; and U.S. Pat. No. 6,994,708, Apr. 18, 2002, Scott Manzo; and U.S. Pat. No. 7,320,700, Jan. 22, 2008, Cooper et al.; and U.S. Pat. No. 7,367,973, May 6, 2008, Manzo et al.; and Ser. No. 11/238,794, Sep. 28, 2005, Scott Manzo; and Ser. No. 11/535,426, Sep. 26, 2006, Manzo et al.; all of which are incorporated herein by reference.

Generally, robotic electrosurgical instruments and systems can be used for electrosurgical treatment of tissue during minimally invasive robotic surgical procedures. The electrosurgical instruments are capable of treating tissue with heat produced by electrical energy while cutting, shearing, grasping, engaging, or contacting treatment tissue. For example, an electrocautery instrument may be used to apply an electrical current to tissue in a surgical site so as to burn or seal ruptured blood vessels.

Electrosurgical instruments may apply a high-frequency alternating current to surrounding tissue, thereby to cause the tissue temperature to rise to the point where the tissue is cut or coagulates. Alternatively, electrosurgical instruments may apply heat to tissue by means of electrically generated heat inside the instrument. Regardless, electrosurgical treatments may further reduce bleeding of tissue by cauterizing tissue and coagulating blood, or achieve various other desired effects on the treatment tissue such as sealing tissue together. The electrosurgical treatment is carried out in a safe and effective manner that incorporates a variety of safety features to prevent current leakage to non-target tissue so as to reduce collateral tissue damage, unwanted burning, or the like.

For electrosurgical instruments, a range of supply settings may be used for cutting, coagulation and the like. An exemplary power supply can create a power output up to approximately one-hundred-twenty (120) watts (W) for cauterizing the target tissue. The voltage used with a bipolar robotic cauterizer tool is generally between zero (0) volts (V) and one thousand (1000) V peak-to peak, and preferably between one-hundred (100) V and five-hundred (500) V. As long as the jaws and electrodes are both in good contact with the tissue intended to be cauterized and/or cut, there is much less chance of voltage from the electrodes arcing to other conductive components on the instrument (e.g., the wrist, shaft, or pulleys). It should be appreciated, however, that the voltage setting of the electrosurgical power generator will vary depending on the specific dimensions of the electrodes, the tissue to be treated, and the like.

Referring now to FIG. 2A, robotic electrosurgical instruments 101A, 101B and endoscopic camera 101C are mounted to the robotic surgical arms 153. Each of the robotic electrosurgical instruments typically include an elongated shaft, with proximal end coupled to a housing and a distal end having one, two, or more end effectors 212. The end effectors 212 are generally mounted on wrist-like mechanisms pivotally coupled to the distal ends of the shafts, for enabling the instruments to perform one or more surgical tasks. Generally, the elongated shafts of surgical instruments allow the end effectors 212 to be inserted through entry ports in a patient's body so as to access the internal surgical site. Movement of the end effectors 212 and the electrosurgical instruments is generally controlled via master controls at the master console 150,150A.

Electrosurgical instruments may be categorized as being monopolar or bipolar. For either electrosurgical tool type, the energization of one or both electrodes in the end effectors 212 is controllable by the surgeon operating the surgeon's console 150,150A.

For a monopolar electrosurgical tool, the patient is grounded and a voltage is supplied to tissue through an electrode coupled to an end effector. In the monopolar tool, an electrically conductive cable within the tool extends from one plug 474A of the housing 401 to the electrode at the end effector. An external cable with first and second ends, releaseably plugs into the plug 474A at the first end and to an appropriate electrical generating source unit (ESU) at the second end. The plug 474A of the tool may typically be a conventional banana-type plug to receive a banana-type connector.

For a bipolar electrosurgical tool, a voltage is supplied to tissue through the use of two electrodes, a first electrode coupled to a first end effector and a second electrode coupled to a second end effector. The two electrodes on the end effectors of the bipolar tool when energized are set at two different electrical potentials and preferably do not come in contact with each other when energy is applied.

In a bipolar tool, a pair of electrically conductive cables within the tool extend from two plugs 474A,474B of the housing 401 to the two electrodes at the respective two end effectors. A pair of external cables with first and second ends, releaseably plug into the plugs 474A,474B at the first end and to a pair of plugs of an appropriate electrical generating source unit (ESU) at the second end. The plugs 474A, 474B of the tool may typically be a conventional banana-type plug to receive a banana-type connector.

It will be appreciated that a number of elements of the tool are formed of a non-conductive or insulative material, such as, ULTEM, electrical grade fiberglass/vinyl ester composite material, or a liquid crystal polyester VECTRAN or coated with a non-conductive or insulative material, e.g., a nylon or parylene, such as Nylon-11 or Parylene C. For example, the housing 401 is typically of a non-conductive plastics material. As another example, the shaft 404 is typically made entirely from a nonconductive material, or at least sheathed in such a material, to insulate the shaft from the patient, in particular in the region of the port of entry coincident with the center of rotation. One nonconductive material for the shaft comprises an electrical grade fiberglass/vinyl ester composite material. Alternatively, a shaft of stainless steel or carbon fiber may be coated with, e.g., a nylon or parylene, such as Nylon-11 or Parylene C. It has been found that the electrode at the end effectors should be insulated from the rest of the instrument 400 so as to inhibit current leakage from the electrode to other elements in the instrument 400.

While electrosurgical tools and systems are described herein with respect to the embodiments of the invention, the principles, methods, techniques, systems and apparatus of the invention may be applicable to other types of tools and systems.

User Interfaces for Electrosurgical Systems

An electrosurgical tool may be mounted to any one or more of the robotic arms of a surgical system and manipulated by a surgeon from the surgeon's console. In some cases, two electrosurgical tools are mounted to a left robotic arm and a right robotic arm. Previously, keeping track of which tool in which side or hand was to be electrically activated was left to memory, particularly when the same type of electrosurgical tool was mounted to each arm. Different foot pedals for different types of electro surgical tools may have provided some guidance on the handedness of the electrosurgical tools.

An enhanced user interface for electrosurgical systems is disclosed herein to allow control swapping between robotic surgical tools, such as a plurality of robotic electro-surgical tools, and to provide an indication to a surgeon as to which side and tools are ready to provide electrosurgical energy and which side is actually activated (firing) to deliver electrosurgical energy to the tissue.

During initial testing of a graphical user interface for a new integrated energy management system, a bright blue colored border was placed around an edge of either the left or right side of the surgeon's display to indicate if the left or right tool was receiving energy. It was discovered that surgeons sometimes do not notice the bright blue colored border at the edge of a display, perhaps because they are focusing on the tissue of interest in the center of the display. As a result, surgeons sometimes do not realize which electrosurgical tool is ready to be energized (activated), or that they are energizing (activating) an electrosurgical tool when they did not intend to. Alternatively, a surgeon may not realize they are energizing (activating) an electrosurgical tool on the wrong side, opposite the desired side.

The enhanced user interface for electrosurgical systems disclosed herein can provide further information to the surgeon so they know which side and tool is ready to provide electrosurgical energy and which side is actually activated (firing) to provide electrosurgical energy. There are three possible ways that may be used alone or in combinations of two or more to provide an enhanced user interface for electrosurgical systems that target the human senses: an enhanced visual display, an enhanced audio output, and/or haptic output or feedback.

Enhanced Graphical User Interface for Electro Surgical Systems

One possible method of further informing a surgeon of the electrosurgical tools is to provide an enhanced visual display through a graphical user interface (GUI) that is displayed to the surgeon at the surgeon's console. A graphical user interface may provide a persistent visual indication that is easier to notice on the periphery of the screen. The GUI may alternatively provide movement in the peripheral vision of the user which tends to be highly effective at attracting user attention. For example, a moving barber pole pattern that zips up and down at the side of the screen, or a different color or light on the side corresponding to the "hot hand" are examples of such displays. The GUI may provide persistent, and/or a momentary indication of an electrosurgical instrument having the capability of being activated. This indication may be associated with or overlaid upon the image of the instrument itself. The GUI may also provide a momentary visual indication whenever energy is activated. For example the border around the left or right side could flash or change color when energy is activated to give the user a visual change when energy is activated.

In FIG. 4, a graphical user interface may be displayed around or near edges of the display like a border. In a stereoscopic display 312, a left user interface border 461L and a right user interface border 461R may be overlaid (fused) onto the video images of a surgical site as shown displayed on display devices 452L,452R.

Figure 5C:
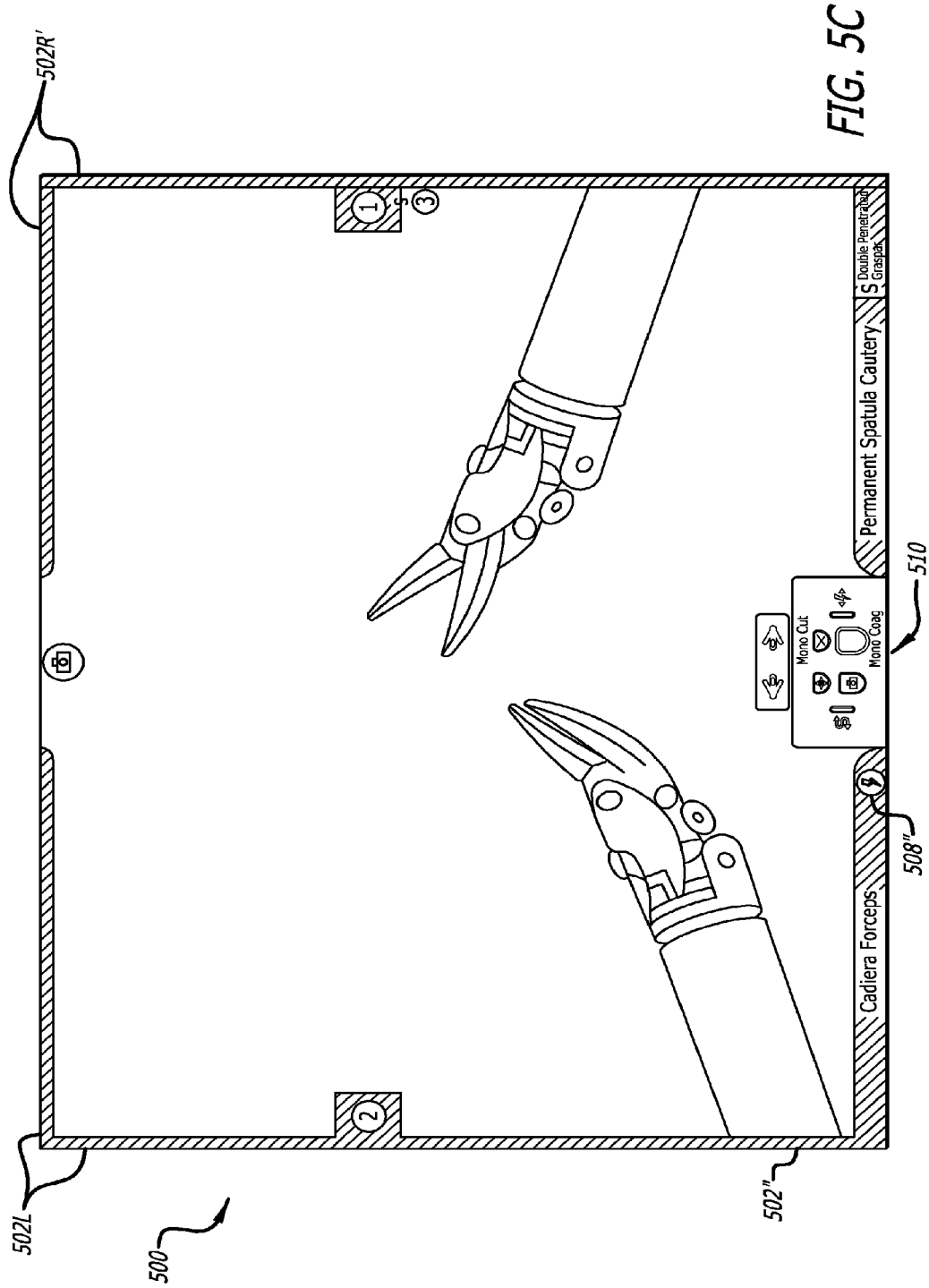

Referring now to FIGS. 5A-5C, an electrosurgical graphical user interface (GUI) 502 for a surgical system is shown overlaid onto (fused together with) video images 501 of a surgical site in a display 500. Note that the left robotic surgical tool image 101L and the right robotic surgical tool image 101R in FIGS. 5A-5C are exemplary images and may not necessarily be representative of electrosurgical tools nor the specific types of robotic surgical tools indicated by the GUI 502. The GUI 502 may be fused together and overlaid onto the video images 501 by a graphics generator 322. The display 500 shown in FIGS. 5A-5C may represent the left display 452L, the right display 452R, or what the surgeon sees when viewing the stereoscopic display 312.

The GUI 502 may be overlaid as a user interface border on the video images 501 including a left colored border 502L and a right colored border 502R. The GUI 502 further includes a left tool number icon 504L, a right tool number icon 504R, a swap tool number icon 504S, a left tool type text icon 505L, a right tool type text icon 505R, a swap icon 506, and a swap tool type text icon 509. The user interface 502 further includes master control icons 510 and an energy ball icon 508. The user interface 502 may further include a camera orientation icon 507. The camera orientation icon 507 may be used to indicate the orientation of the video or camera images 501 captured by the endoscopic camera.

In FIG. 5A, the left colored half frame or left colored border 502L and the right colored half frame or the right colored border 502R may used different colors to indicate either an inactive energy tool type or an active energy tool type controlled by the left hand and right hand respectively. For example, the left colored border 502L may have a color (e.g., a brown color) to indicate an inactive energy tool type controlled by the left hand, foot and/or side of the surgeon's console that does not have the capability to couple energy into tissue. The right colored border 502R may have a color (e.g., a blue color) to indicate an active energy tool type that is capable of coupling energy into tissue to cut or cauterize and is controlled by the right hand, foot and/or side of the surgeon's console. If the energy control is multiplexed to the opposite side, the right colored border 502R may change color (e.g., to a brown color) such as illustrated in FIG. 5C to indicate that the right hand tool will not be activated to couple energy into tissue, even though the tool has that capability.

In FIG. 5A, the GUI 502 illustrates that the right-hand instrument is an energy instrument (e.g., a permanent spatula cautery tool) and is ready to fire or apply energy to tissue. The color of the right half-frame 502R on the right-hand side informs the user that when one of the energy pedals is stepped on, the instrument currently controlled by the user's right hand will become energized to apply energy into tissue.

The robotic surgical tool mounted to robotic arms of the patient side cart may both be electrosurgical tools. In which case, it may be desirable to swap energy control of the surgeon's console between tools controlled by the left and right hands. This may be referred to as swapping the handedness (or sidedness) of the energy control of the surgeon's console, even though the same foot and foot pedals are used to control the electrosurgical tool.

The energy ball icon 508 indicates the handedness of the energy control of the surgeon's console. If the handedness of the energy control is swapped, the energy ball icon 508 is accordingly swapped between the right side (near center) and the left side (near center) of the display to indicate which tool may be energy controlled by controls (e.g., the foot pedals) at the surgeon's console.

The background color and symbol overlaid onto the energy ball may be used to indicate either an inactive energy tool type or an active energy tool type controlled by the respective handedness. This is because the handedness of the energy control may be swapped to a tool that is incapable of delivering energy to tissue. In FIG. 5A, the energy ball icon 508 is illustrated with a blue background and a yellow lightning bolt, for example, to indicate an active energy handedness associated with the right tool. In FIG. 5C, an inactive energy ball icon 508" is illustrated with a grey background and a grey strike-through lightning bolt, for example, to indicate an inactive energy handedness associated with the left tool in contrast with the active energy ball icon 508.

The left tool icon number 504L and the right tool icon number 504R may illustrate the number of the tools that are mounted to robotic arms of the patient side care that are capable of being controlled by the surgeon's console. The colors of the left tool icon number 504L and the right tool icon number 504R may be colored similar to the left colored border 502L and the right colored border 502R to further indicate either an inactive energy tool type or an active energy tool type controlled by the left hand and right hand respectively. The swap tool icon number 504S indicates the tool number to which a swap of control may be made by the surgeon's console. The swap tool icon number 504S may be colored to indicate that its associated robotic tool is not presently controlled by the surgeon's console. The swap icon 506 indicates whether or not an alternate tool may be controlled by a master grip of the surgeon's console and that a swap may be made. The position of the swap icon near the right or left side border of the user interface indicates the handedness of the swapped tool. The swap tool text icon 509 in the right side of the GUI indicates the alternate tool that may be controlled with the right master grip of the surgeon's console.

If a tool swap is initiated by a surgeon, the swap tool icon number 504S and the right tool icon 504R may swap positions and colors about the swap icon 506 to indicate the associated robotic tool which is presently controlled and which tool is in not presently controlled (also referred to as being idle) by the right master grip of the surgeon's console. The right tool type text icon 505R and the swap tool text icon 509 may also swap positions and colors to further indicate the active robotic surgical tool which is presently controlled by the surgeon's right hand on the right master grip of the surgeon's console in contrast to the idle robotic surgical tool. Generally, robotic surgical tools controllable by the right master controller are represented in the right half of the user interface and robotic surgical tools controllable by the left master controller are represented in the left half of the user interface.

The camera orientation icon 507, near a top center of the GUI 502, illustrates the orientation of the endoscopic camera with respect to a reference, the patient side cart. This allows the surgeon to understand the orientation of the video images with respect to the patient side cart of the robotic surgical system. This may help orient the patient's body as well so that the surgeon is better equipped to understand the orientation of organs and tissue therein.

The master control icons 510 illustrate a mapping of the physical controls at the surgeon's console. The master control icons 510 include a pedal map and a master grip map. The master control icons 510 are best illustrated in FIGS. 6A-6B and are now described in further detail.

Figure 6A:
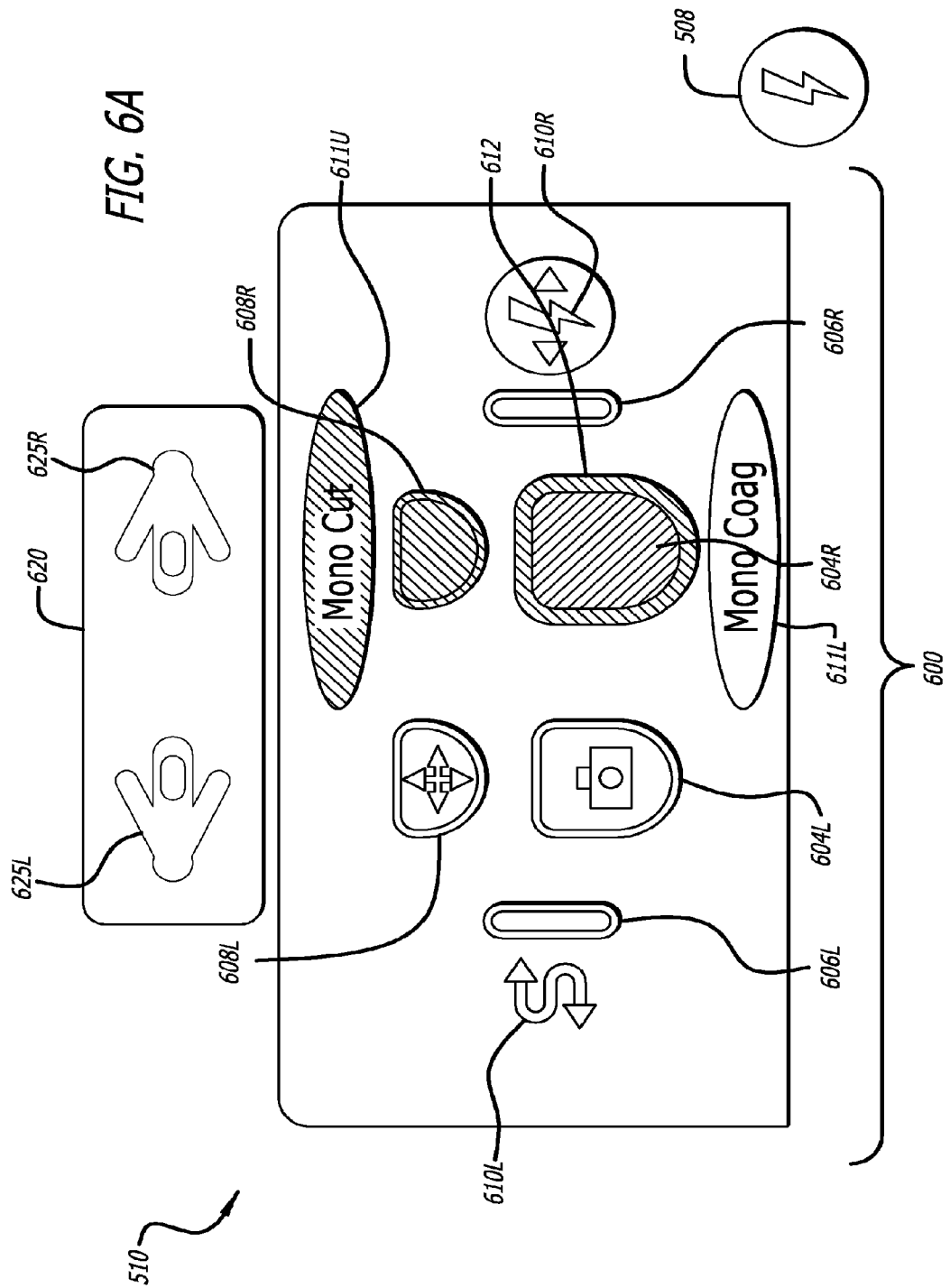
FIGS. 6A-6B illustrate magnified images of master control icons including a master grip map and a pedal map.
Figure 6B:
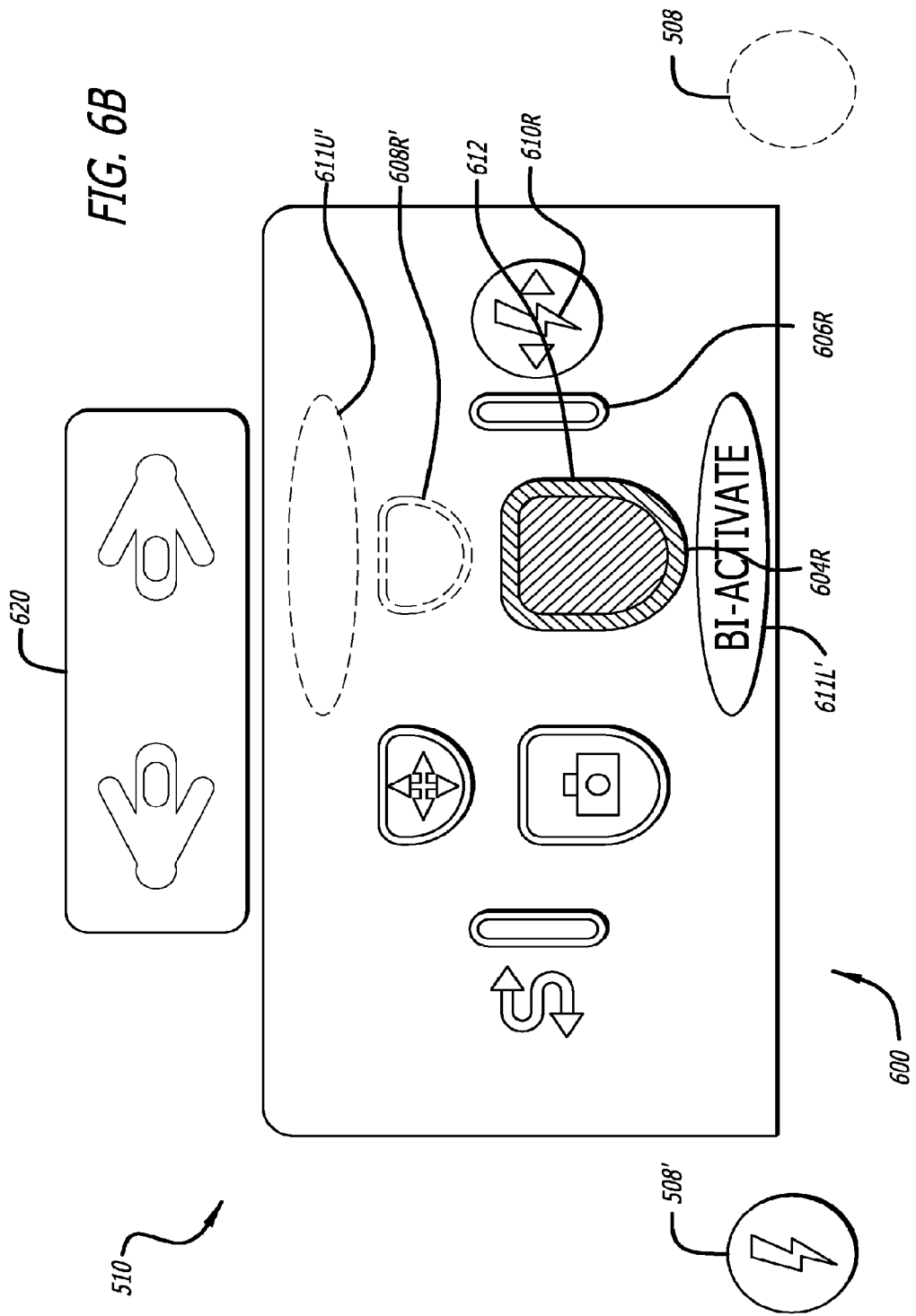

Referring now to FIGS. 6A-6B, a magnified view of the master control icons 510 is illustrated, including pedal icons 600 and master control grip icons 620. The pedal icons 600 include a lower left pedal icon 604L, a lower right pedal icon 604R, a left switch pedal icon 606L, a right switch pedal icon 606R, an upper left pedal icon 608L, and an upper right pedal icon 608R. The pedal icons 600 may further include an upper pedal function icon 611U and a lower pedal function icon 611L. The master control grip icons 620 include a left grip control icon 625L and a right grip control icon 625R.

The pedal icons 600 of the master control icons 510 are displayed in a pedal map (position and orientation) that matches the position and orientation of the respective controllable foot pedals (e.g., see FIG. 7A). The pedal map reminds the surgeon which foot (left or right) and foot position (top, bottom, or side position) controls the controllable foot pedals. In this manner, to increase efficiency, a surgeon may not need not move his head away from the stereoscopic display and view his feet over the controllable foot pedals to control them.

The master control grip icons 620 are displayed in a master grip map, a left master control grip icon 625L representing a status of the left master grip and a right master control grip icon 625R representing a status of the right master grip of the surgeons' console. The master grip map of the master control grip icons 620 may also remind the surgeon where to position his hands to grab the master grips. The status indication provided by the master control grip icons may indicated which master control grip may be clutched to reposition a hand in space or control some other controllable feature at the surgeon's console.

During electrosurgical procedures, the controllable foot pedals (e.g., see FIG. 7A) may have assigned functionality. The pedal icons may indicate the assigned functionality of the controllable foot pedals. As illustrated in FIG. 6A, an upper pedal function icon 611U near the upper right pedal icon 606R indicates Mono Cut (monopolar cutting) associated with the upper right pedal while the lower pedal function icon 611L near the lower right pedal icon 604R indicates Mono Coag (monopolar coagulation) associated with the lower right pedal. The pedal map of pedal icons may further include a pedal outline or halo 612 around one of the pedal icons to indicate the activation of pedal to the user and application of energy to tissue.

The pedal map of pedal icons may further include a left function icon 610L near the left switch pedal icon 606L associated with the functionality of the left horizontal switch pedal and a right function icon 610R near the left switch pedal icon 606L associated with the functionality of the right horizontal switch pedal. In FIG. 6A, a swap tool icon 610L in the shape of the letter "S" with arrowheads is illustrated near the left switch pedal icon 606L. An energy swap icon 610R in the shape of a lighting bolt with arrowheads nearby is illustrated near the right switch pedal icon 606R to illustrate the energy swapping functionality of the right horizontal switch pedal.

The left grip control icon 625L and/or the right grip control icon 625R may inform the user of active control of the respective left and/or right tools at the surgeon's console. In response to a left master switch or a right master switch, the left and/or right tools may be clutched from control of the robotic arms and surgical tools they control. Either or both icons may indicate inactive tool control—clutch of the master grips at the surgeon's console from tool control—so that the left master grip and/or the right master grip may be used to control other features of the robotic surgical system without movement of a surgical tool.

As discussed previously, the energy ball icon 508 indicates the handedness of the energy control of the surgeon's console. In FIG. 6A, the right-handed energy ball 508 is illustrated to the right of the master control icons 510. In this case, the electrosurgical tool in the right hand is to be energized by one or more pedals at the surgeon's console. The magnified view of the pedal map shows which pedal is currently being activated by outlining or haloing the Mono Coag pedal icon 604R with a colored halo or outline 612 (e.g., orange color) that differs from the color fill (e.g., blue) of the pedal icon. The colored halo or outline 612 activation indicator reinforces the information provided to the user as which pedal is being activated.

The pedal map of pedal icons, including the colored halo or outline 612 indicator, helps to teach users the foot pedal layout without requiring them to remove their head from the 3D stereoscopic display to actually look at the position of their feet over the pedals. Unlike the colored side-bar or activated energy strip bar or border 522, the pedal map of pedal icons and the colored halo or outline 612 activation indicator is placed more towards the center of the surgeons vision so as to not rely on peripheral vision alone. If the surgeon steps on the Mono Coag energy pedal, the Mono Coag pedal icon 604R is outlined or haloed by the colored halo or outline 612 activation indicator as best shown in FIG. 6A. If the surgeon steps on the Mono Cut energy pedal instead, the Mono Cut pedal icon 608R would be outlined or haloed by the colored halo or outline 612 activation indicator instead of the Mono Coag pedal icon 604R. In either case, the colored side-bar or activated energy strip border 522 is displayed in an active side such as shown in FIG. 5B when either energy pedal is selected by the user and energy is ready to be delivered to an instrument. A terracing of the upper and lower foot pedals deters the surgeon from concurrently pressing both upper and lower foot pedals.

To switch the energy activation from a tool in one hand to a tool in the opposite hand, an energy swap pedal (e.g., pedal 706R-a horizontal switch pedal) is selected by the surgeon's foot to toggle the control. The energy ball 508 moves from the right side to the left side in the GUI near the pedal map of the pedal icons 600. FIG. 6B illustrates an energy ball icon 508" positioned in the GUI to the left of the master control icons.

In FIG. 6B, the left tool is a bipolar electrosurgical tool such that the lower right foot pedal (e.g., pedal 704R) is activate as indicated by the lower pedal function 611L'. With a bipolar electrosurgical tool, only one foot pedal may be used to control energy. Thus, the upper pedal function icon 611U' indicates no functionality associated with the upper right foot pedal—an inactive foot pedal. The upper pedal icon 608R' may further indicate its inactive status by being filled with an inactive color (e.g., a grey color fill) and/or displayed with a strike-through.

The pedal icons themselves may have different colors or overlaid illustrations to further indicate their functionality to the surgeon. The upper pedal icon 608L may include an illustration of crossed doubled headed arrows (an up and down arrow crossing over a left and right arrow) to indicate that it allows free movement of the master manipulators, temporarily decoupling them from the surgical instruments. The lower left pedal icon 604L has an illustration of a camera icon to further inform the user that it allows the user to control the motion of the endoscopic camera. The lower right pedal icon 604R may have a different color fill (e.g., blue colored fill) than the upper right pedal icon 608R (e.g., yellow colored fill) to illustrate different controls to apply different levels of energy to a mono-polar electrosurgical tool. The lower right pedal icon 604R may have a different color fill to illustrate a single activate control of a bipolar electrosurgical tool while the upper right pedal icon 608R may not be present or provide an indication of being inactive.

Referring now to FIG. 5B, assume the surgeon activated the energy pedal 704R to begin energizing the electrosurgical tool on the right hand side. The pedal halo 612 surrounds the lower right pedal icon 604R to illustrate activation by the pedal 704R. An activated energy strip border 522 with a different color than the right side border 502R may be overlaid onto the right hand side during electrosurgical tool activation. The activated energy strip border 522 further illustrates energy activation of the right side tool and not the left side tool. The surgeon can readily see the activated energy strip border 522 because it changes the right side border 502R when the foot pedal is depressed to activate the electrosurgical generating unit (ESU) to couple energy into tissue. If instead the left hand side is to be activated, the activated energy strip border 522 with a different color than the left side border 502L may be overlaid onto the left hand side during electrosurgical tool activation.

In FIG. 5B, the pedal halo or outline 612 surrounding the lower right pedal icon 604R illustrates activating monopolar coagulation energy. A colored bar (the activated energy strip border 522) on the right side of the display serves as a change in the user's peripheral vision. This change in the user's peripheral vision reinforces informing the user of which side energy is being applied, without requiring the user to actively look at the indicator (the colored bar or activated energy strip border 522). As mentioned previously, instead of the activated energy strip border with a different color, a graphical barber-pole that illustrates movement may be used in the GUI to inform a user. Alternatively, a graphical spinning wheel may be displayed in a side or corner of the GUI. In yet another embodiment, a bright pulsing light may slide or bounce up and down along a side portion of the GUI border. Alternatively, a series of graphical light bars may light up when electrosurgical energy is to be supplied to a tool. Collectively, these graphical display devices may be referred to as an activated energy indicator. While the graphical images of an activated energy indicator have been described as being in the periphery and overlaid onto a portion of the GUI border, they may be located elsewhere. For example, an activated energy indicator may be overlaid on top of and/or automatically positioned near the images of the robotic surgical tools or instruments. The activated energy indicator in this case may track the tools or instruments as they move around the surgical site.

A surgeon may toggle left/right hand side control with an "energy swap" pedal whenever desired, independently of whether there is an electrosurgical capable tool in either hand. However, the active energy color border (e.g., blue) is displayed in the right and/or left user interface borders 502L-502R only when all of the necessary conditions for enabling energy activation are met. Whenever the energy swap pedal is pressed, the side (left or right) capable of delivering energy changes. This is represented in the GUI by the little energy ball 508, 508" near the lower border (frame-half) portion in either side of the display. The energy ball swaps sides each time the energy swap pedal is pressed.

When the energy ball is swapped to a side that has an electrosurgical capable tool mounted to its robotic arm and the appropriate electrosurgical generator for that type of tool is also detected, the GUI displays an active border (e.g., bright or blue in color) on the same side as the energy ball, an active energy ball 508 with an active background or fill color (e.g., bright or blue in color) and an active symbol such as a yellow colored lightning bolt, and an inactive border (e.g., dark or brown in color) on the opposite side of the energy ball.

In FIG. 5A, by use of the energy swap pedal, the surgeon has assigned energy to the right hand side, denoted by the active energy ball 508 to the right of the foot pedal map of the master control icons 510 next to the right tool text icon 505R with the exemplary text Permanent Spatula Cautery.

If a user swaps the energy ball when there is an energy-capable instrument on both hands, the active colored half-frame jumps from left to right along with the active energy ball, thus immediately visually notifying a user that a change has taken place, and providing a constant indication as to which side (left or right) will be activated when the energy pedal(s) are pressed. If a user fails to pay attention to the bright blue frame and steps on one of the energy pedals when the "wrong" side is selected, the appearance of the activated energy strip bar 522 (e.g., a bright orange bar) serves as a visual reminder that is very strong in the peripheral vision as to which side is being activated. This visual feedback to the surgeon/user can help mitigate mistakes and reinforce in the user's minds which side energy has been swapped to.

When an energy ball 508 is swapped to a side that does not have an electrosurgical capable tool, or if the system does not detect the necessary electrosurgical generator (ESU) for an electrosurgical tool currently controlled by that side, the GUI display an inactive border color (e.g., dark or brown color) on the opposite side of the energy ball, inactive border color (e.g., dark or brown color) on the same side as the energy ball, and an inactive energy ball 508" with an inactive background or fill color (e.g., dark or gray color) and an inactive symbol such as a faint outline of a lightning bolt with a diagonal slash through it (e.g., a diagonal strike-through).

Referring now to FIG. 5C, the energy swap pedal 706R is selected to swap energy control to the left hand side tool. The energy ball icon 508" is located to the left of the master control icons 510 to indicate the energy foot pedals are used to control a left hand side tool. However, the robotic surgical tool controlled by the left hand side is not capable of providing energy to tissue—it is not an electrosurgical tool. While the energy ball icon 508" is located on the left hand side of the user interface, it has an inactive color fill (e.g., a gray color fill) and a strike-through lightning bolt to inform the user that energy will not be provided to the tissue in this case, even if an energy pedal is selected. Further, a color (e.g., brown) of the left side border 502L and the right hand side border 502R' indicate a lack of energy capability in both the left and right hand sides. That is, in this case energy will not be provided to the tissue through either the left hand or right hand robotic surgical tools.

In FIG. 5C, the surgeon has enabled the left hand side to deliver energy. However, the tool mounted to the robotic arm under control of the left hand side is a Cadiere Forceps which is not an energy-capable tool. Although the energy ball 508" has been moved to the left hand side, there is now no capacity to deliver energy to tissue. Thus, both the left and right half frames or borders of the GUI are colored as being inactive (e.g. dark or brown color). The GUI would be displayed the same if there were an energy-capable tool in the left hand and an inappropriate electrosurgical energy generating device were connected to the system. The indication to the surgeon that no energy is available is most quickly evident by the lack of an active half frame (e.g., blue or bright color) on the left or right of the screen, and can be seen by looking at the type of energy ball being displayed as well.

A user may decide to swap the tool that is being mechanically controlled by the left or right master grips and associated left and right hands by selecting a tool swap pedal (e.g., pedal 706L shown in FIG. 7A).

The visual feedback provided by the GUI is somewhat master-centric in the sense that it informs the user as to whether the instrument controlled by his left hand or right hand will fire (energize or become active) when one of the energy pedals is pressed. In the case of three or more instruments, this paradigm doesn't need to change. At any one time, only one instrument is actively assigned to be controlled by the left master grip/left hand and only one instrument is actively assigned to be controlled by the right master grip/right hand. The actively controlled instruments have active tool text icons 505R,505L displayed in the graphical user interface that are large with bold text. In contrast, idle instruments that are waiting to be controlled by a swap control signal from the user have a swap tool text icon 509.

The swap tab or swap tool text icon 509 off to the side in the corner of the GUI is smaller in size and color filled to indicate inactive control. (e.g., dark or gray or brown colored tab). The swap tool text icon 509 includes text indicating the type of instrument (e.g., a double fenestrated grasper) that is mounted to another one of the right side arms. The swap tool text icon or swap tab in the right side indicates that the third instrument is associated with the right master. However, the third instrument is currently not the active instrument in the right side as shown in the Figures. The first instrument indicated by the right tool type text tab or icon 505R is active. If a user activates the tool swap or arm swap pedal 706L, his right master would cease controlling the Permanent Spatula Cautery instrument, and would start controlling the Double Fenestrated Grasper instrument. This change may be reflected in the GUI by swapping the positions of the two instrument name tabs or icons 505R and 509 or 505L and 509. The tool swap pedal 706L may generate a tool swap signal to swap the kinematic control by the right master grip between a pair of robotic surgical tools. With a change of context, it may also be used to generate a console swap signal to swap some control over the remote controlled equipment and robotic surgical tools between a pair of surgeon control consoles.

Enhanced Haptic User Interface for Electro Surgical Systems

In addition or alternatively to visual feedback provided by the GUI, tactile feedback may be used to indicate the energy status of an electrosurgical tool to a user. A user may be informed as to whichever electrosurgical instrument is ready to be energized (sometimes referred to as being hot or ready to fire) by one or more types of vibration at points where a user makes contact with the surgeon's consoler 150,150A. For example, the haptic feedback output may be coupled to the surgeon's hands, feet, and/or arms.

A vibration representing the haptic or tactile feedback may be achieved by use of a dedicated (e.g. vibrotactile) device or by making further use of one or more pre-existing devices in the surgeon's console, such as the powered axis of the input control wrists of the master controllers. In either case, a haptic/tactile feedback generator 321 in the surgeons console 150,150A, such as illustrated in FIG. 3A, may be used to generate and control the haptic feedback. The haptic/tactile feedback generator 321 may generate a left feedback control signal to be coupled to left side vibrating mechanisms/devices and a right feedback control signal to be coupled to right side vibrating mechanisms/devices.

Haptic feedback may be provided to the surgeon's hands. In FIG. 3C, each master grip control input 325 (left and right side) may include a vibrating feedback mechanism 399 to provide tactile feedback. Alternatively, the roll motor 370a of the input control wrist or an electro magnet 396 of the master grip control input may be controlled by the haptic feedback generator 321 in the surgeons console to generate a vibration in the left or right master grip controller 325.

Haptic feedback may be provided to the surgeon's feet. In FIG. 7D, each of the horizontal pedal assemblies 704L-704R may further include a vibrating feedback mechanism 726. In FIG. 7E, each of the vertical pedal assemblies 706L-706R may further include a vibrating feedback mechanism 736.

Haptic feedback may be provided to the surgeon's arms. In FIG. 9, the arm-rest 314 in the Surgeon's console may include a left vibrating feedback mechanism 936L and a right vibrating feedback mechanism 736R.

These vibrating feedback mechanisms, alone or in combination, may be used to provide feedback to the user regarding the left or right side activation of energy to tissue. In the arm rest or at the master controllers, a left side vibrating feedback mechanism may be activated to indicate left side activation of energy supplied to the left handed tool (or that left side is ready to fire) and a right side vibrating feedback mechanism may be activated to indicate right side activation of energy supplied to the right handed tool (or that right side is ready to fire). Alternatively, different vibrating patterns may be used to distinguish between left side activation and right side activation of energy, such as for the haptic feedback provided to a surgeon's foot. The surgeon could sense the difference in the vibrating patterns with his foot. As discussed further herein, several different signal profiles of signals may be coupled to the vibrating feedback mechanisms to generate vibrations for vibrating patterns.

Enhanced Audible User Interface for Electro Surgical Systems

In addition to visual feedback provided by the GUI and/or tactile/haptic feedback provided by a vibrating device, auditory feedback may be used to indicate the energy status of an electrosurgical tool to a user. The audible feedback, alone or in combination with visual and haptic feedback, may be used to provide feedback to the user regarding the left or right side activation of energy to tissue.

The surgeon's console 150,150A may include one or more audio transducers or speakers. In FIG. 3A, the surgeon's console 150,150A includes a left speaker 315L and a right speaker 315R coupled to a sound generator 317. When the user/surgeon is properly positioned, his left ear is near the left speaker and his right ear is near the right speaker.

The sound generator may be a stereo sound generator to independently couple sounds to the left speaker 315L and the right speaker 315R. In this case, the left speaker generating a sound may be used to indicate a left side activation of energy to tissue and the right speaker generating a sound may be used to indicate a right side activation of energy to tissue. Alternatively, the sound generator may be a mono sound generator to couple the same sounds to the left speaker 315L and the right speaker 315R. In this case, different audible patterns may be used to distinguish between left side activation and right side activation of energy to tissue, such as for the haptic feedback provided to a surgeon's foot. The surgeon could sense the difference in the audible patterns.

Enhanced Feedback Signaling

The type of feedback provided to a user at the surgeon's console 150, 150A may have one or more different forms—visual feedback, haptic/tactile feedback, and/or audible feedback. The feedback may be seen by the user's eyes; felt by the user's feet, hands, and/or arms; or heard by the user's ears. The feedback itself may be of a distinguishable pattern and provide further information if different signal patterns/profiles are used.

Figure 12:
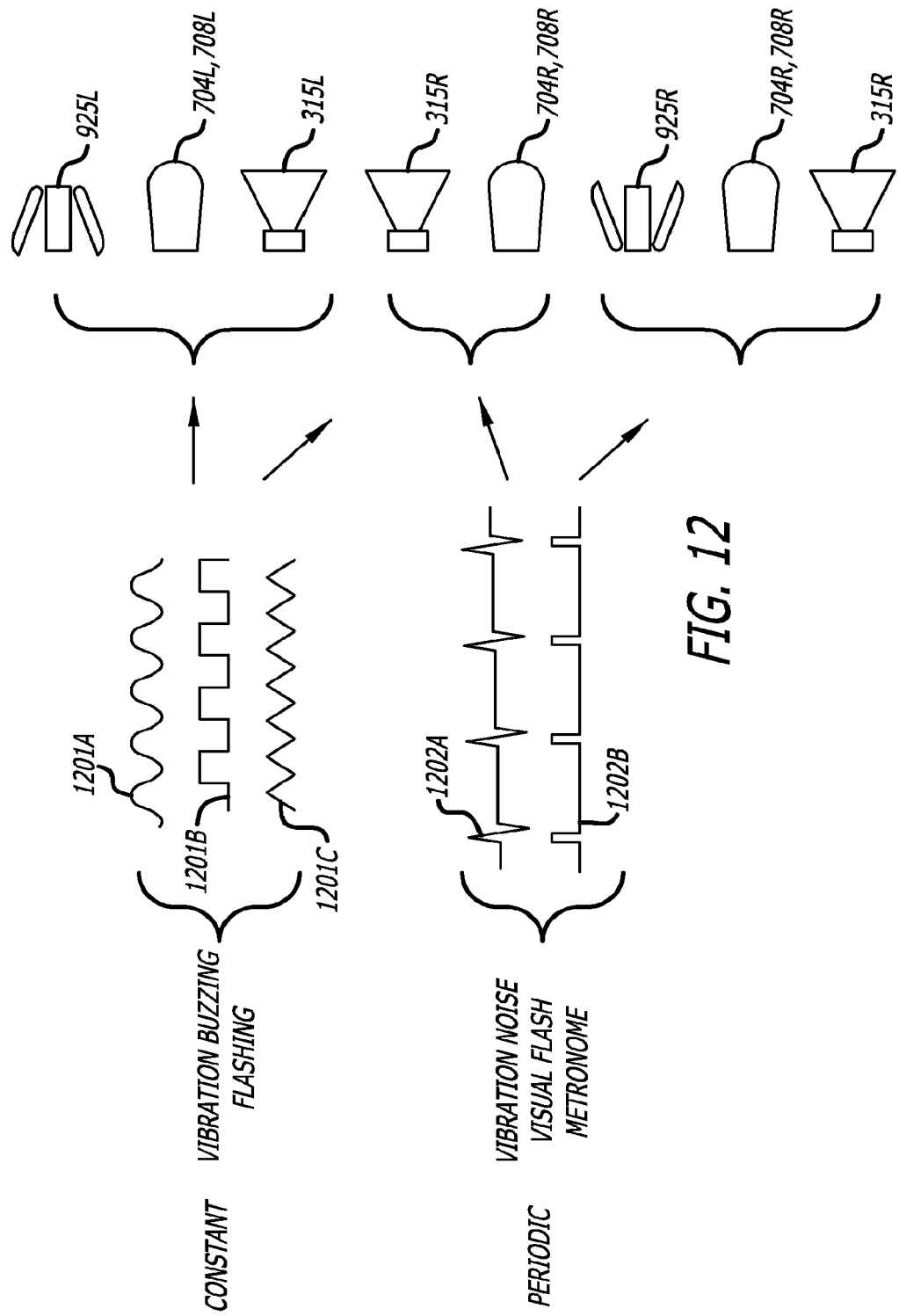
FIG. 12 illustrates waveform diagrams of different signal profiles of signals that may be used to provide user feedback; the handedness—left or right hand (or sidedness—left or right side) of the user feedback; and differential user feedback with different signal patterns.

Referring now to FIG. 12, different signal profiles of signals that may be used to provide user feedback. In one case, the feedback pattern/provide may be a constant vibration, a constant buzzing sound, or a constant visual flashing display in the GUI that a user can sense. In another case, the feedback may be periodic or metronome-like, such as a periodic vibration felt by the user, a periodic noise generated by left and/or right speakers, or a periodic visual flash generated on the display that a user may see.

To generate a constant feedback due to a vibration, a buzz or a flashing may be generated by a sinusoidal curve 1201A, a square wave curve for 1201B, or a triangular waveform 1201C. Each of these may have a fifty percent (50%) duty cycle to generate the constant feedback. To generate a periodic feedback, such as a periodic vibration, periodic noise, or periodic visual flash, a waveform coupled into the feedback transducer may have a periodic pulse such as the triangular waveform 1202A or the periodic pulse waveform 1202B illustrated in FIG. 12. In this case, the waveforms each have a duty cycle that is less than or greater than fifty percent (50%). The feedback signals may be tuned or adjusted to suit each user's individual preference. That is, the rate/frequency, amplitude, duty cycle, etc., can be tuned or adjusted to suit a user preference in distinguishing between left and right activation, for example.

The constant feedback and the periodic feedback are distinguishable and may be used to indicate different feedback information to the user. The periodic feedback and the constant feedback may be used to distinguish between right activation and left activation of an electrosurgical instrument when equally coupled to one or more speakers 315L,315R in a mono audible system or one or more energy pedals 704R,708R in the right side of the pedal tray.

To further distinguish between left and right, the constant feedback (e.g., waveforms 1201A, 1201B, 1201C) may be coupled into a left master controller 905L, a left pedal 704L,708L, and/or a left speaker 315L to indicate left hand side energy activation for a left hand side tool; while the periodic feedback (e.g., waveforms 1202A, 1202B) may be coupled to the right speaker 315R, the right pedals 704R, 708R, and/or the right master controller 905R to indicate right hand side activation of the right hand side tool. Alternatively, the periodic feedback may be coupled to the left side transducers to indicate left hand side energy activation for a left hand side tool; while the constant feedback may be coupled to the right side feedback transducers to indicate right hand side activation of the right hand side tool. In this manner, the user is further informed of the side of activation by the handedness of the feedback.

For example, a persistent audio indication (e.g., a 1 Hz "metronome" click) may be coupled to the user's left or right ear by the respective speaker to indicate that the left or right hand side tool will be receiving energy. Alternatively, a momentary audio indication (e.g., clicks, buzzing) may be coupled to the user's left or right ear by the respective speaker when the energy is activated in the left or right tool. In another embodiment of the invention, a mono system, a metronome like tone may be coupled into speakers of the surgeon's console to indicate left hand side tool activation energy while a momentary audio indication may be coupled into the surgeon's console to indicate right hand side tool activation energy.

A persistent haptic indication (e.g., a haptic "metronome" pulse) may be coupled to the left or right hand grip by respective vibrating devices to indicate that the left or right hand side tool will be receiving energy. Alternatively, a persistent haptic indication may be coupled to a foot pedal to differentiate from energy activation of the left hand side from the right hand side. Alternatively, a persistent haptic indication may be coupled to the left portion or the right portion of the arm rest by respective vibrating devices to distinguish between energy activation of the left hand side and energy activation of the right hand side. In another embodiment, a momentary haptic indication (e.g., click, buzz vibration) may be coupled to the master control (left or right) by a respective vibrating device corresponding to the instrument that receives the energy.

A persistent visual indication (e.g., a barber pole) may be overlaid onto a left or right active strip in the user interface by the graphics generator to indicate that the left or right hand side tool will be receiving energy. In another embodiment, a momentary indication (e.g., a periodic flash of a left or right side active strip in the graphical user interface by the graphics generator may be used to indicate that the left or right hand side tool will be receiving energy.

The overall time period that the feedback signals are generated for either side may vary on how it is desired that the feedback be conveyed. For example, the feedback signal may be constantly generated during surgery in the side that has the hot hand to energize an electrosurgical tool. Alternatively, the feedback signal may be generated to provide feedback only while a user depresses an energy pedal to energize an electrosurgical tool. In yet another alternate embodiment of the invention, the feedback signal may be generated for an overall predetermined time period after the user only touches the pedal. In this case, the foot pedals (such as the energy pedals) may include a feather-touch sensing device or an optical sensing device 727 as shown in FIG. 7D to detect when a user's foot is hovering over a particular pedal that may be integrated with their switches. In another embodiment of the invention, feedback may only be provided when a pedal is ready to be activated or be pressed, such as to fire to couple energy into tissue. If no electrosurgical tool is present on the side selected, the pedal is not ready to be activated and thus feedback would not be provided that would indicate it was ready. If an electrosurgical tool is present on the side selected but no generator is coupled to the electrosurgical tool or the wrong energy is coupled to the electrosurgical tool or being controlled by the foot pedal, the pedal is not ready to be activated and thus feedback would not be provided that would indicate it was ready.

Enhanced Energy Activation Control

Methods to prevent or mitigate the effects of incorrect energy activation are now described.

In the case where a user (surgeon, operator O) has forgotten or fails to check the left or right status of energy, it is possible that he or she will fire the incorrect energy device by simply stepping on one of the energy activation pedals. That is, electrosurgical energy may be applied to the tool on the wrong side if the wrong side is selected for application of energy by the energy pedals. To avoid this, user feedback may be provided before the electrosurgical energy is applied to the tool so that the user may back off from firing the incorrect energy device.

Immediately upon pressing the energy pedal, the user may be given sided feedback (alternatively referred to as handedness feedback) indicating which electrosurgical tool, the left side tool or the right side tool (respectively controlled by the left or right master grip), is going to fire. This sided feedback, as described previously, could be the visual feedback, haptic feedback, audio feedback, or a combination thereof. For example, a buzzing sound and a flashing icon on the left hand or right hand side of display could indicate which handed energy tool, the energy instrument controlled by the left hand or the right hand, is going to fire, before it does fire or as it actually does fire.

If, simultaneously, the energy is actually applied to tissue while the sided feedback is presented, some damage may possibly occur to patient tissue. If the sided feedback is rapidly presented to the user, it can allow a user to quickly cease application of energy and thus mitigate any possible damage. Moreover, a brief delay in the actual application of energy after the sided feedback is presented, may allow the user to detect the feedback and cease the mis-application of energy to tissue before it occurs. An application of energy to tissue by an electrosurgical tool on the wrong side is an exemplary mis-application of energy.

Figure 13A:
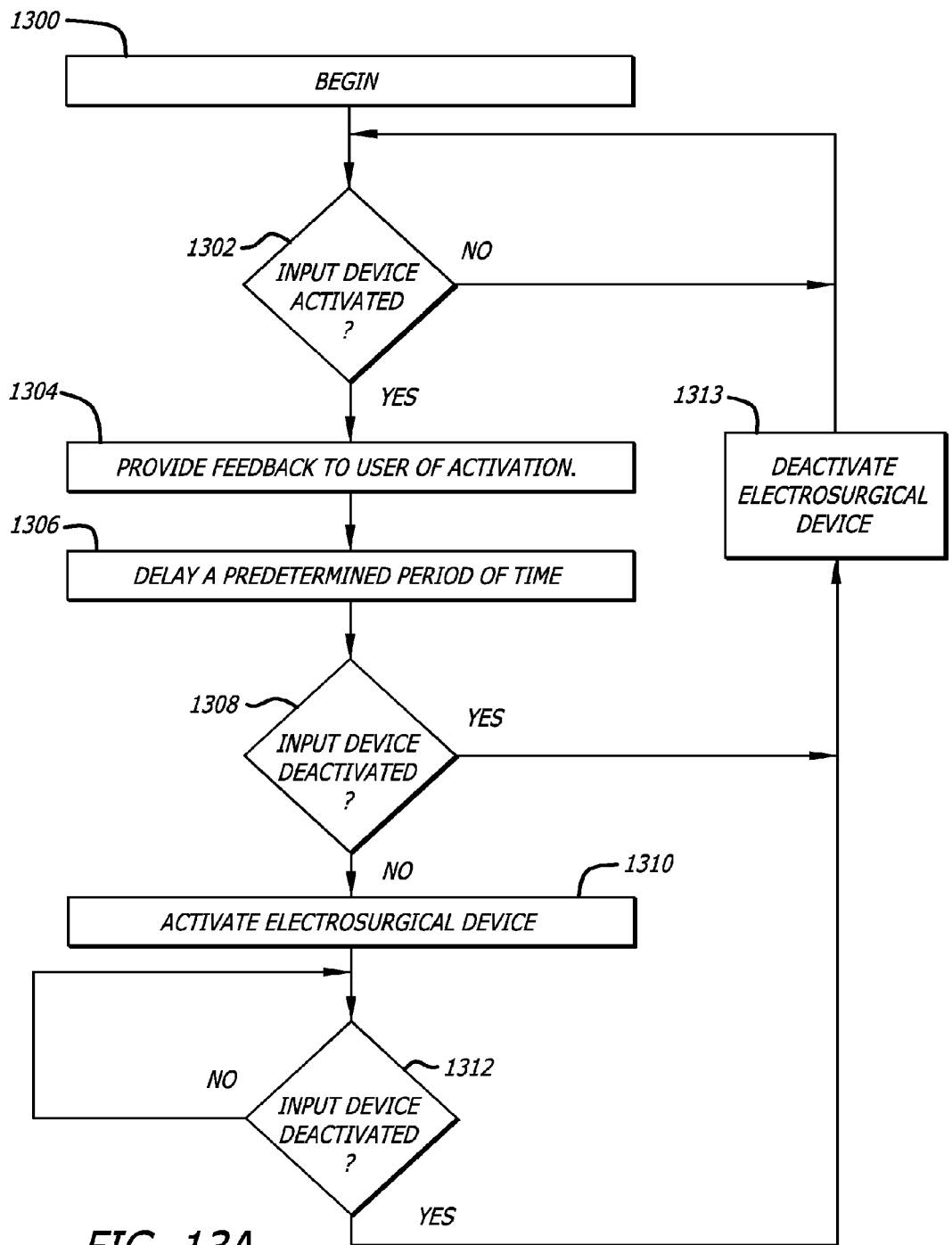
FIGS. 13A-13B are flowchart diagrams illustrating methods for enhanced activation of an electrosurgical device.

Referring now to FIG. 13A, a flowchart diagram is illustrated for enhanced activation of an electrosurgical device in accordance with one embodiment of the invention. The method begins at block 1300 then goes to block 1302.

At block 1302, a determination is made if the input device is activated to apply electrosurgical energy to a tool. If the input device is not activated, the process loops back around to block 1302 which is then repeated. If the input device is activated, the process goes to block 1304. The input device in this case may be an energy pedal that is pressed upon by a user's foot to close a switch to eventually cause electrosurgical energy to be applied to a tool with a selected handedness. The input device request the application of electrosurgical energy in this case before it is to be applied.

At block 1304, the user is provided feedback of the activation of the input device to request the application of electrosurgical energy. The user feedback may be in the form of that previously described. The user feedback provides not only identification of activeness but the handedness of the activation. Prior to applying energy to tissue through the electrosurgical device, a delay period may be provided to allow time for the user to back off. The process goes to block 1306.

At block 1306, the system waits for a predetermined period of time (delay) before applying electrosurgical energy in order to allow the user to receive the feedback and decide whether or not to cancel the activation of an electrosurgical device. The process goes to block 1308.

At block 1308, a determination is made if the input device has been deactivated. If so the process goes to 1313. If not, the process goes to block 1310. In the case of an electrosurgical tool, a user may release the energy pedal by lifting up and taking his foot off the pedal to allow it to open the switch and deactivate the application of electrosurgical energy. The process then goes to block 1310.

At block 1310, assuming the input device was not deactivated, the electrosurgical device is activated to apply energy to tissue of a patient. The process then goes to block 1312.

At block 1312, a determination is made if the input device has been deactivated. If not, the process loops back around to block 1312 and continues to sense whether or not the input device has been deactivated. If it is detected that the input device has been deactivated, the users foot has been lifted off the pedal, the process goes to block 1313.

At block 1313, with the input device being deactivated, the electrosurgical device is deactivated so that energy is not further delivered to tissue. The process then loops back around to block 1302 to continue through the loop.

In this manner, each time that an input device is activated to cause electrosurgical energy to be delivered to tissue, a check is made whether or not a mistake has been made by the surgeon in activating the electrosurgical device. However, a surgeon may only need be reminded once and a check made once whether or not it is proper to activate an electrosurgical device. In which case, the repetitive delay period introduced by block 1306 may be unnecessary after a first check has been made.

Figure 13B:
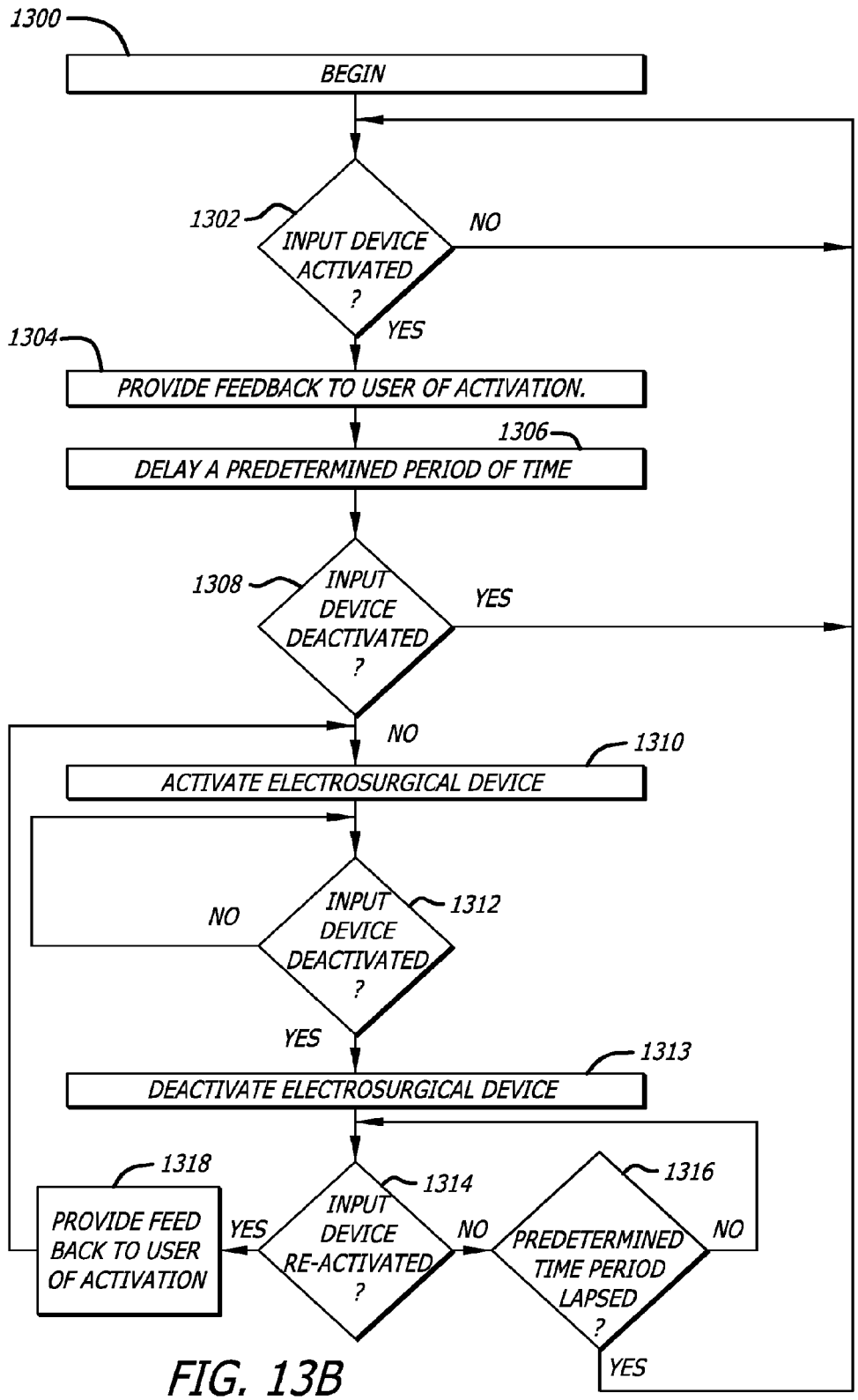

Referring now to FIG. 13B, a flowchart of a process for enhanced activation of an electrosurgical tool is illustrated in accordance with another embodiment of the invention. In this process, there is an initial check to determine if it is proper to activate an electrosurgical device. Subsequently, if the electrosurgical tool is repeatedly used within a predetermined period of time, there is no delay in the activation of the electrosurgical device. The process shown in FIG. 13B can be viewed as having a delayed activation loop with a delayed activation and a subsequent no delay activation loop. The process begins with block 1300 and then goes to block 1302.

At block 1302, a determination is made if the input device is activated to apply electrosurgical energy to a tool. If the input device is not activated, the process loops back around to block 1302 which is then repeated. If the input device is activated, the process goes to block 1304.

At block 1304, user feedback is generated and provided to the user to indicate the start of the electrosurgical activation process. The process then goes to block 1306.

At block 1306, a delay of a predetermined period of time is introduced before activation of the electrosurgical device. This delay allows some time for the user to receive the feedback and make a decision to deactivate the input device to avoid tissue damage if miss-applied. If the feedback agrees with the user selection, the user may not deactivate the input device and waits the predetermined period of time before electrosurgical energy is applied. After the delay, the process goes to block 1308.

At block 1308, a determination is made if the input device has been deactivated. If so, the process loops back around to block 1302. If not, the input device remains activated and the process goes to block 1310.

At block 1310, the electrosurgical device is activated such that electrosurgical energy is delivered to tissue at the end of the tool with the selected handedness. The process then goes to block 1312.

At block 1312, a determination is made again if the input device is deactivated. If not, the process loops around continuously to detect when the input device is deactivated. If it was detected that the input device has been deactivated, the process continues and goes to block 1313.

At block 1313, with the input device being deactivated, the electrosurgical device is deactivated in response thereto. The process then goes to block 1314.

At block 1314, a determination is made if the input device has been re-activated. If so, the process goes to block 1318. If the input device has not been re-activated, the process goes to block 1316. The input device may be one or more energy pedals that are pressed by a user's foot to request the application of electrosurgical energy to tissue.

At block 1316, a determination is made if a predetermined period of time has elapsed prior to the reactivation of the input device. The predetermined period of time allows the system to determine if the electrosurgical device is going to be repeatedly used or not. An electrosurgical tool is repeatedly used if the time period is short prior to reactivation of the input device. If the input device is reactivated before the predetermined time period lapses, the process goes to block 1318. If the predetermined time period has elapsed without the input device being re-activated, the process goes back to block 1302 to repeat the initial delayed activation loop and allow the user to back off from input activation and the application of electrosurgical energy to tissue.

At block 1318, the user is provided feedback of the repeated activation of the electrosurgical device. The process then loops around back to block 1310 where the electrosurgical device is activated once again. The blocks 1310-1318 are repeated when the electrosurgical device is used repeatedly with short periods of time before reactivation.

Graphical User Interface Formation Methods

Figure 14:
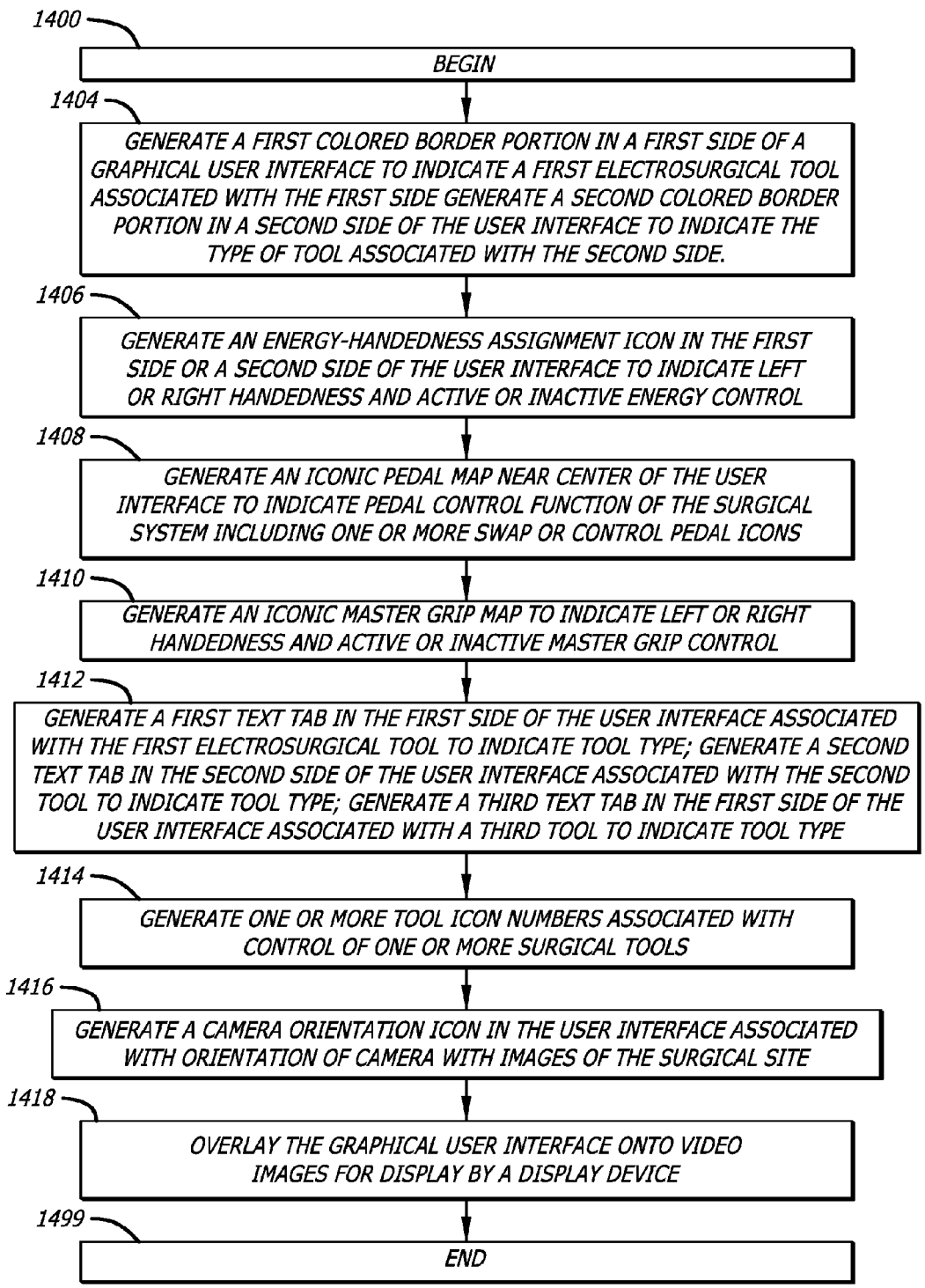
FIG. 14 is a flow chart illustrating a method for generating a graphical user interface (GUI) and displaying the GUI with video images to provide visual feedback to a user.

Referring now to FIG. 14, a flow chart is illustrated of a process for generating a graphical user interface and displaying the GUI with video images to provide visual feedback to a user. The process begins at process block 1400 and then goes to process block 1404.

At process block 1404, a first color bordered portion in a first side of a user interface is generated in order to indicate an energy activation status of a first electrosurgical tool that is associated with the first side. A second color border portion is generated in the second side of the user interface in order to indicate the energy activation status of a second tool the type of tool associated with the second side. For example, as shown in FIG. 5A, the right side colored border, 502R, is colored blue to indicate that the first tool is an electrosurgical tool that may be activated by a surgeon. In contrast, the left color border at 502R may be colored brown to indicate the lack of an electrosurgical tool (a surgical tool without energy capability) being associated with the left hand and therefore may not be controlled to provide energy to tissue. The process then goes to block 1406.

At process block 1406, an energy handedness assignment icon (an energy ball icon 508) is generated in the first side or second side of the user interface to indicate left or right handedness and an active or inactive energy control of the robotic surgical tool in the side selected be the user. The process then goes to block 1408.

At block 1408, an iconic pedal map including pedal icons are generated near a center of the user interface to indicate pedal control functions of the surgical system. The iconic pedal map may include one or more swap or control pedal icons. The iconic pedal map is a subset of master control icons that may be displayed by the graphical user interface. The iconic pedal map may illustrate the control status of the pedals in the robotic surgical system. The pedal icons and their positions in the pedal map may be a scaled representation of the foot pedals that may be controlled by the user's feet. The process then moves to block 1410.

At block 1410, an iconic master grip handle map including master grip icons is generated to indicate left and right active or inactive master grip control. As shown in FIG. 5A, the master grip handle map may be a part of the master control icons 510. The master grip icons may be scaled representations of the master grip input controls that may be controlled by the user's hands. The process then goes to block 1412.

At block 1412, one or more text tabs may be generated to indicate the type of surgical tools that are mounted and currently available to the user for control during surgery. A first text tab in the first side of the user interface located at the first electrosurgical tool is generated to indicate its tool type. A second text tab in the second side of the user interface associated with a second tool is generated to indicate its tool type. A third text tab in the first side or second side of the user interface may be generated and associated with the third tool to indicate the tool type to which a swap may occur. In FIG. 5A, a left tool type text icon 505L, a right tool text icon 505R. and a swap tool text icon 509 are illustrated. The process then goes to block 1414.

At block 1414, one or more tool icon numbers associated with control of the respective one or more surgical tools is generated. In FIG. 5A, a right tool number icon 504R, a left tool icon 504L, and a swap tool icon number 504S are generated in the user interface. The process then goes to block 1416.

At block 1416, a camera orientation icon is generated in the user interface associated with the orientation of an endoscopic camera that captures the images of the surgical worksite. This provides an indication of the orientation of the camera with respect to the images of the surgical site to provide a frame of reference. The process then goes to process block 1418.

At process block 1418, the user interface is overlaid onto video images in the display device. The user interface is graphically generated and fused together with video images by the graphics generator 322 so that it is overlaid on top of the video images. With the graphical user interfaced fused together with the video images, pixel information of image frames may be sent to the display device for display.

Icons generated for the user interface may change in color (bright or dark color), position (left or right), and information content (active icon/inactive icon). Moreover, the video images may change over time as more frames of images are captured by the endoscopic camera. In which case, one or more of the process steps may repeated as need to continuously generate the graphical user interface overlaid onto the video images. If a surgery is completed, the camera is turned off and the process may then go to block 1499 and end. While a number of the processes are shown and described as being performed serially, one or more of them may be concurrently performed as if being performed in parallel.

Swapping Energy Handedness

Previously, swapping energy handedness or simply energy swapping was described with reference to FIG. 5A, as well as other figures. The method of energy swapping at the surgeon's console is now described with reference to the flow chart of FIG. 15.

Figure 15:
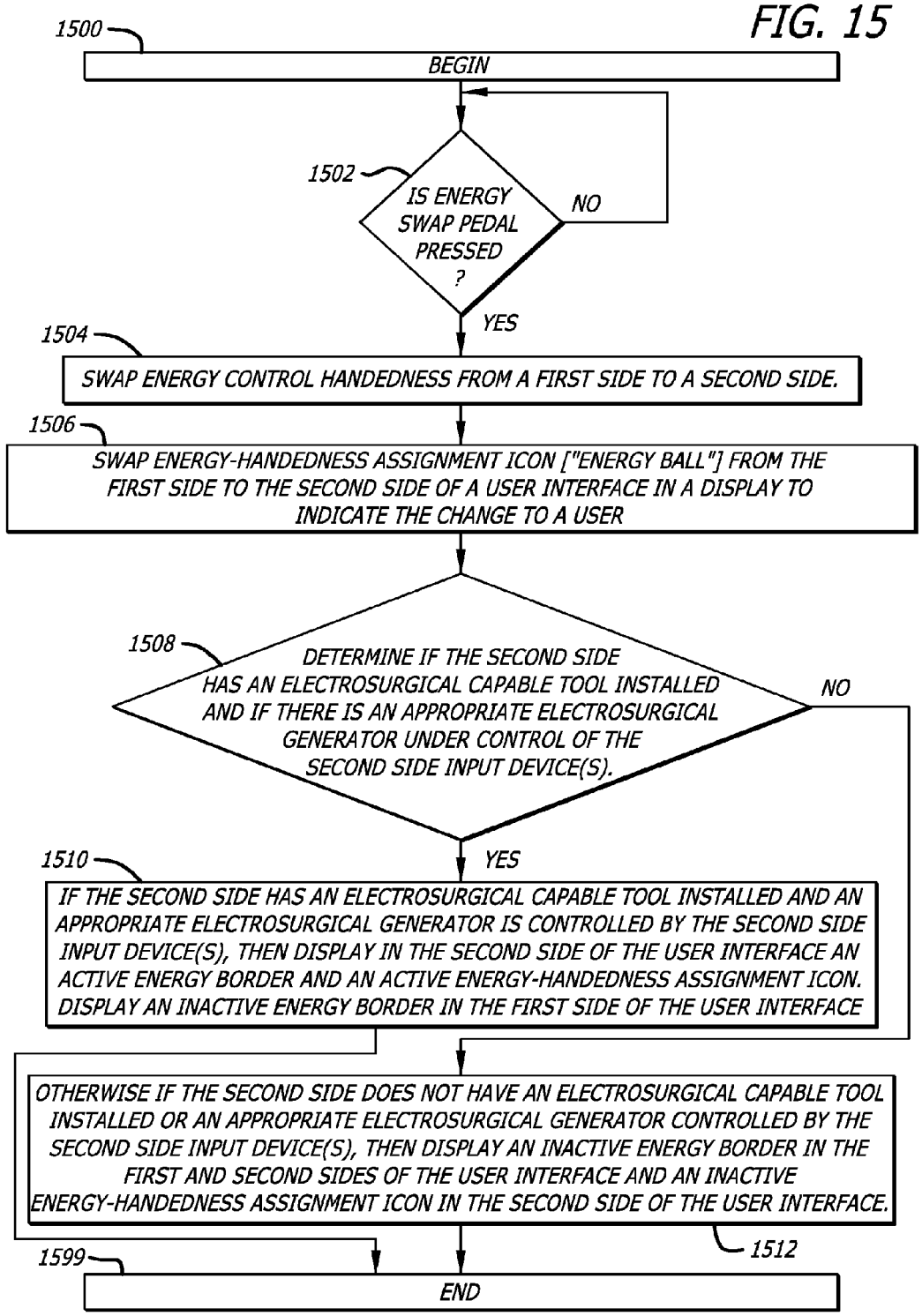
FIG. 15 is a flow chart of a method of swapping energy handedness from one surgical tool in one side to another surgical tool in an opposite side.

Referring now to FIG. 15, a method of swapping energy handedness from one surgical tool in one side to another surgical tool in an opposite side is illustrated by a flowchart. The process begins at process block 1500 then goes to process block 1502.

At process block 1502, a determination is made if an energy swap is requested to swap the handedness of the energy control from left to right or right to left. An energy swap may be requested by the user by pressing on the energy swap pedal 706R. If an energy swap is not requested, the process loops around back to block 1502 until the energy swap is requested by the user by way of the selection of the energy swap pedal. If an energy swap has been requested (energy swap pedal has been pressed) by the user so that energy control is to be passed from one handed side to the other, the process goes to process block 1504.

At process block 1504, energy control handedness is swapped from a first side to a second side in response to the selection of the energy swap pedal. For example, the energy control handedness may be swapped from the right hand as shown by the user interface illustrated in FIG. 5A to the left hand as shown by the user interface illustrated in FIG. 5C. The process then goes to process block 1506.

At process block 1506, the energy-handedness assignment icon (energy ball 508) is swapped from the first side to the second side of the user interface to indicate the energy handedness swap to a user. For example, FIG. 5A shows the energy ball icon 508 in the right color border 502R. After the energy swap request from the user, the energy ball icon swaps sides. As shown in FIG. 5C, for example, the energy ball icon 508" is in the left side border 502L after the swap. The process then goes to block 1508.

At block 1508, determination is made if the second side has an electrosurgical capable tool installed and if so, is there an appropriate electrosurgical generator under control of the second side input devices. If the second side has both an electrosurgical capable tool installed and an appropriate electrosurgical generator under its control, then the process goes to process block 1510. If not, the process goes to block 1512.

At block 1510, assuming the second side has an electrosurgical capable tool installed and an appropriate electrosurgical generator is controlled by the second side input devices, then an active energy border and an active energy-handedness assignment icon are displayed in the second side of the user interface. An inactive energy border may be displayed in the first side of the user interface as the energy control is now with the opposite side. The right side border 502R shown in FIG. 5A illustrates an active energy border with an active energy ball icon 508. After the swap, the right side border 502R' shown in FIG. 5C illustrates an inactive energy border.

At block 1512, assuming that the second side does not have an electrosurgical capable tool installed or alternatively, there is not an appropriate electrosurgical generator controlled by the second side input devices, then an inactive energy border is displayed in the first and second sides of the user interface. FIG. 5C illustrates an inactive energy border in both the left side border 502L and the right side border 502R'. Also, an inactive energy handedness assignment icon 508" may be generated and displayed in the user interface, such as shown in FIG. 5C.

Upon completion of the energy control swap from one hand to the other and the display of the proper feedback to the user in the user interface 1512, the process may go to block 1599 and end until the user selects to make another energy control swap.

Adaptable Integrated Control of Remote Controlled Equipment

In a number of surgical procedures, surgeons want to be able to use one more pieces of controlled equipment for robotic surgical tools in addition to an electrosurgical generating unit (ESU) for a monopolar or bipolar electrosurgical tool. For example, they may want to use an ultrasound tool or a laser capable tool that requires an ultrasound generator or a laser generator as the controlled equipment. In order to use the extra controlled equipment, an external dedicated activation pedal was placed outside the surgeon console 150,150A. Previously, the surgeon had to move their foot off the pedals 318 to activate the extra controlled equipment to provide a signal to the addition robotic surgical tool. Movement of the foot away from the pedals 318 to control the external dedicated activation pedal is inconvenient and can result in less efficiency during surgery as the surgeon looks away from the monitor down to his foot.

In order to provide increased flexibility for surgeons to use a plurality of ESUs as well as other remote controllable equipment with robotic surgical instruments in a surgical procedure, an adaptable integrated interface is provided between the between ESUs, activation pedals, and the robotic surgical instruments. The adaptable integrated interface is programmable by software so that the remote controlled equipment is controlled by the pedals of the surgeons console in response to the type robotic surgical instruments, controlled equipment supporting the respective instruments, and a user selection of the one or more active tools. A surgeon can control multiple ESUs and other controlled equipment, such as suction pumps, irrigation pumps, and stapling devices, from the surgeons console by an adaptable integrated interface controller and integrated control system.

Figure 16:
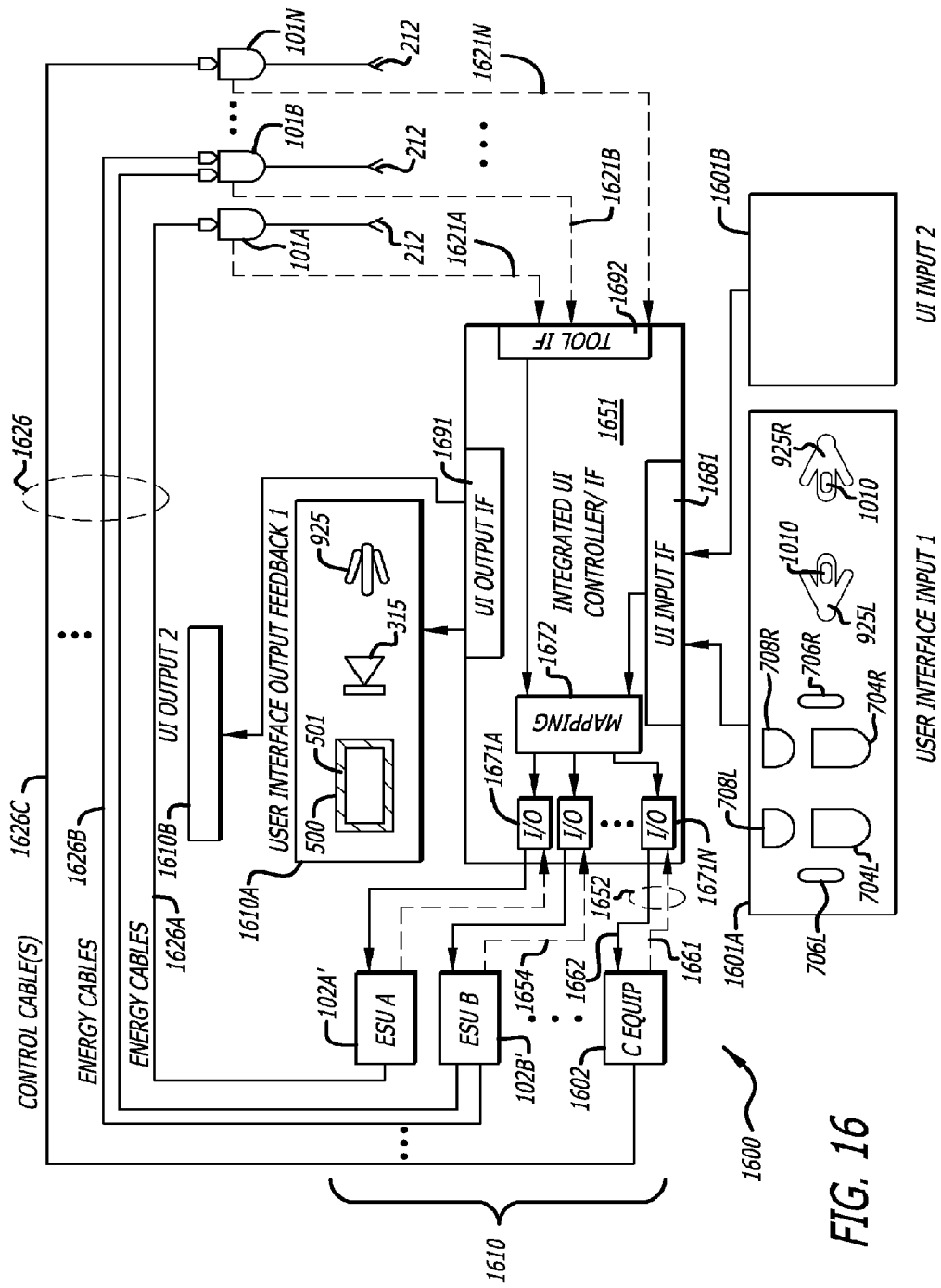
FIG. 16 illustrates a block diagram of an integrated robotic surgical control system.

Referring now to FIG. 16, a block diagram of an integrated robotic surgical control system 1600 is illustrated. At the heart of the integrated control system is an integrated user interface controller 1651. The integrated user interface controller 1651 may be located at the surgeon's console 150 or the control cart 150B shown in FIG. 1B. The integrated user interface controller 1651 includes a plurality of input-output interfaces 1671A-1671N and a signal mapping device (also referred to as mapping logic) 1672 coupled together. The integrated user interface controller 1651 may further include a user input interface 1681 coupled between the mapping device 1672 and the user interface input devices 1601A-1601B to generate control signals in response to selection of the one or more foot pedal switches. The integrated user interface controller 1651 may further include a user output interface 1691 to couple to user interface output devices 1610A-1610B and a processor interface to couple to a processor (not shown, see FIG. 21) to inform a user of the status (e.g., active or hot-ready to fire- or inactive) of the robotic surgical tools by various user interface techniques described herein. The integrated user interface controller 1651 may further include a tool interface 1692 coupled to the mapping logic 1672 to communicate with one or more robotic surgical tools 101A-101N or intelligent robotic surgical tools 101A'-101B'. The tool interface may read tool information from the one or more robotic surgical tools 101A-101N or intelligent robotic surgical tools 101A'-101B'.

The integrated controller 1651 is coupled in communication with user interface input devices 1601A,1601B and user interface output devices 1610A,1610B to respectively receive input commands from the user and provide feedback to the user. The integrated controller 1651 may also be coupled in communication with one or more electrosurgical generating units 102A', 102B' or other remote controllable equipment 1602. The electrosurgical units 102A', 102B' and the other remote controllable equipment 1602 are remotely controlled from the surgeon's console and may be collectively referred to herein as remote controllable equipment 1610. The integrated user interface controller 1651 may be in further communication with one or more robotic electrosurgical tools 101A, 101B and/or other robotic surgical tools 101N coupled to the remote controllable equipment 1610.

The integrated user interface controller 1651 may receive information about the electrosurgical units 102A',102B' and the other remote controllable equipment 1602 to which it is coupled in order to properly control the equipment in its functional support of the robotic surgical tools. To provide information about the remote controllable equipment coupled to the integrated controller 1651, one or more smart cables 1652 may be used.

Smart cables 1652 are specially designed cables that furnish information regarding the electrosurgical units 102A',102B' and other remote controllable equipment 1602 to the integrated user interface controller 1651. The smart cables 1652 couple between an activation port of the ESU or controlled equipment and an input/output interface 1671A-1671N of the integrated controller 1651. The input/output interfaces 1671A-1671N of the integrated controller have software controlled switches that can adapt to the type of signaling needed to activate an ESU or other controlled equipment. The smart cables have unique identifiers that identify the ESU or other controlled equipment to the integrated controller so that the foot pedal switches of the surgeon's consoler are properly mapped to perform the correct action, as if they were the standard issue foot pedal provided with the ESU or other controlled equipment. The specially designed cables may also have further information, regarding the ESU or other remote controlled equipment that it identifies, that can also be passed on to the integrated controller.

The smart cable 1652 may include a data cable 1661 and a control cable 1662. The data cable 1661, which may not couple to the controlled equipment 1610, passes information regarding the remote controllable equipment 1610 to the integrated user interface controller 1651. The control cable 1662, coupled between the controlled equipment 1610 and the integrated user interface controller 1651, allows the input/output interface 1671N of the integrated controller to emulate the functionality of the foot pedal switch the controlled equipment 1610 is expecting. The emulation of the foot pedal switch in effect passes control signals from the integrated user interface controller 1651 to the remote controllable equipment 1610 over the control cable 1662 when a foot pedal at the surgeon's console is activated.

Alternatively a bidirectional data cable 1654, such as an RS232 cable, may be coupled between the integrated user interface controller 1651 and the remote controllable equipment 1610 so that information may be readily passed bi-directionally between each. Instead of or in addition to the control cable 1662, control signals may also be passed over the bidirectional data cable 1654 from the integrated user interface controller 1651 to the remote controllable equipment 1610 instead of emulating the functionality of a foot pedal switch.

The integrated user interface controller 1651 may also be in communication with the one or more robotic surgical tools 101A-101N mounted to the robotic arms over electrical couplings 1621A-1621N facilitated by pins 424 of the tools coupled to terminals of the connector 242 of the robotic arms. The integrated user interface controller 1651 receives information about the one or more robotic surgical tools 101A-101N to properly map and control the remote controllable equipment 1610 that supports the functions of the robotic surgical tools. The one or more integrated circuits 426 in a tool stores information about the robotic surgical tool that is provided to the integrated user interface controller 1651.

When an robotic surgical instrument that use a particular energy type is mounted to a robotic arm, it is identified to the integrated user interface controller 1651 and matched with an appropriate piece of remote controllable equipment, such as an ESU. A user interface input 1601A,1601B and a user interface output 1610A,1610B may be provided to a surgeon at the surgeons console 150,150A such that they can select which instruments they want to actively control with their left and right hands through the left and right master grips of the surgeon's console. Some of the controllable features of the equipment and/or tools can be mapped to one or more foot pedal switches.

The integrated user interface controller 1651 includes the plurality of input-output interfaces 1671-1671N and the signal mapping device 1672 coupled together in order to map the one or more foot pedal switches of the one or more user interface inputs 1601A,1601B to the remote controllable equipment 1610. In this manner, each piece of the remote controllable equipment 1610 may be selectively controlled by one or more foot pedal switches. Some of the one or more foot pedal switches may be used to selectively control the kinematics of a robotic arm and tool, such as the endoscopic camera and the robotic arm to which it is attached. Another signal mapping device and additional input/output interfaces (not shown in FIG. 16) may be used to map the left and right master grips to selectively control the kinematics of other robotic arms and the robotic surgical tools coupled thereto. The swap command can selectively alter the mapping of the left and right master grips to selectively control the kinematics of another robotic arm and robotic surgical tool coupled thereto while another is idle.

The mapping can be automatically performed by the integrated controller 1651 or it may be optionally selected by a surgeon using the user interface inputs 1601A,1601B. In either case, a surgeon can easily operate the remote controllable equipment 1610 and selectively control the supply of energy, fluids, gasses, etc. over the cables/hoses 1626 to the robotic surgical tools 101A-101N and its application to tissue or the surgical site by using the foot pedals and other provided by the surgeon's console. Multiplexing the functionality of the pedals at the surgeon's console vitiates the need for external independent pedal switches to activate the remote controllable equipment. The user interface output 1610A,1610B informs the surgeon which robotic surgical instrument 101A-101N will be supplied with energy, fluids, gasses, etc. over the cables/hoses 1626 and which instrument will apply it within the surgical site.

The integrated controller 1651 may be in communication with more than one surgeon's console to receive the first user interface input 1601A of a first surgeon's console and a second user interface input 1601B of a second surgeon's console. Additionally, the integrated user interface controller 1651 may provide the first user interface output 1610A for the first surgeon's console and a second user interface output 1610B for the second surgeon's console. The second surgeon's console may be offsite located in a different room, building, city, and/or country from that of the first surgeon console.

The first and second user interface inputs 1601A,1601B may each include the one or more foot pedals 704L-704R, 706L-706R, 708L-708R, and the master controllers 925L-925R, each having the switch 1010, as described herein. The first and second surgeon's consoles may interchangeably remotely control the remote controlled equipment and the robotic surgical tools. For example, one or more foot pedals (of the first user interface 1601A) of a first control console may be used to remotely control a first piece of remote controlled equipment to support functions of a first robotic surgical tool while one or more foot pedals 1601B (of the second user interface 1601B) of a second control console may be used to remotely control a second piece of remote controlled equipment to support functions of a second robotic surgical tool. Alternatively, the first surgeon control console may control the kinematics of the robotic surgical tools while the second surgeon control console may control the one or more pieces of the remote controlled equipment to support the functions of the robotic surgical tools by controlling the supply of vacuum, gasses, liquids, and energy to the robotic surgical tools. A console swap signal may be generated by a switch (e.g., pedal switch 706L of the first control console) to map the appropriate foot pedals of either the first or second surgeon console to the remote controlled equipment.

The first and second user interface output 1610A,1610B may each include a graphical user interface 501 that is displayed on one or more displayed devices 500 to provide visual feedback, one or more speakers 315 to provide audible feedback, and/or one or more vibrating mechanisms at the master controller 925 or elsewhere on the surgeon's console to provide haptic/tactile feedback. Other devices in the first and second user interface output 1610A,1610B may be used to provided user feedback.

Figure 17A:
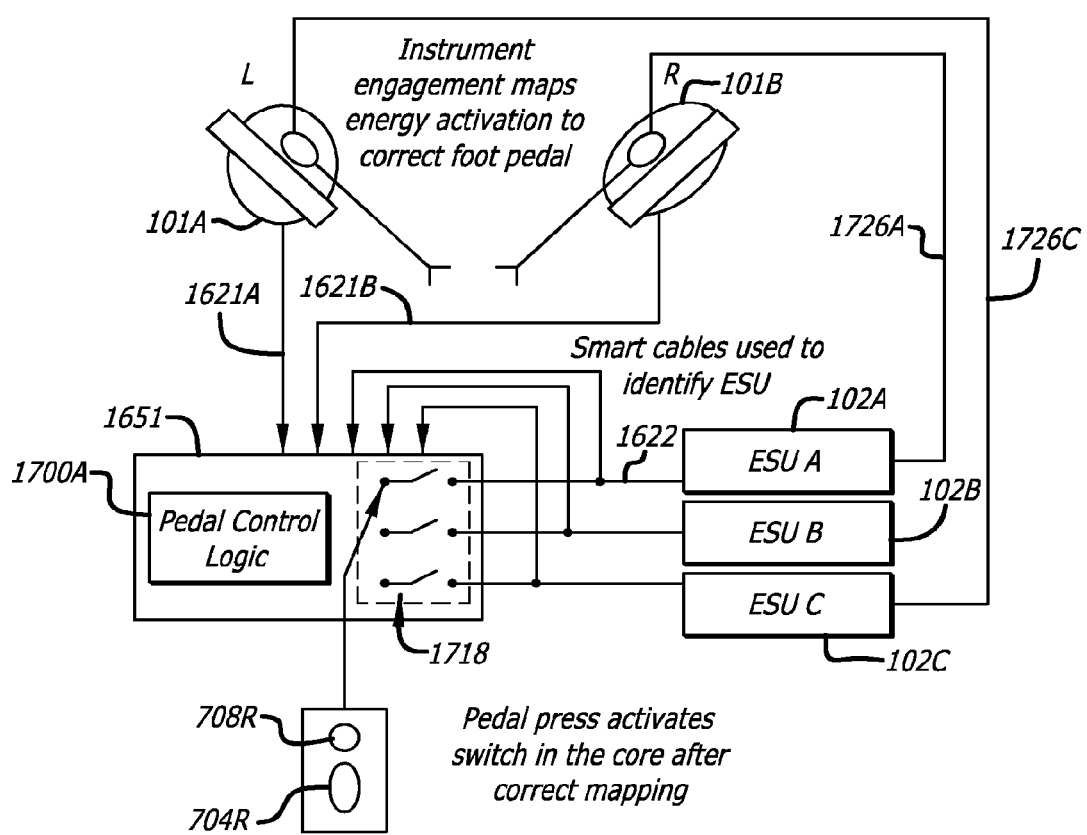
FIGS. 17A-17B illustrate simplified block diagrams of alternate embodiments of the integrated robotic surgical control system.

Referring now to FIG. 17A, a simplified block diagram of the integrated robotic surgical control system is illustrated to describe a first method of operation regarding the control of electrosurgical tools and electrosurgical units to provide energy to tissue. The integrated controller 1651 is coupled in communication with the robotic surgical tools 101A,101B; the electrosurgical units 102A-102C; and a lower right foot pedal 704R and an upper right foot pedal 708R. To provide a consistent user interface input to the user, the lower right foot pedal 704R switches a primary energy source on/off while the upper right pedal 708R switches a secondary energy source on/off for a mono-polar ESU and a mono-polar tool, regardless of the handedness.

The integrated controller 1651 includes pedal control logic 1700A that selectively controls how control signals from the foot pedals are selectively mapped into controlling the electrosurgical units. The pedal control logic 1700A, along with the mapping logic 1672 and I/O interfaces 1617A-1617N, multiplexes control signals from the pedal switches to control the one or more electrosurgical units to supply energy to the electrosurgical tools 101A-101B. The pedal control logic 1700A may include the mapping logic 1672 that maps foot pedal control signals from the foot pedal switches to the appropriate controlled equipment 102A-102C. The I/O interfaces 1617A-1617N are represented by a core of switches 1718 in FIG. 17A.

The electrosurgical units 102A,102C supply energy to the electrosurgical tools 101A-101B over energy supply cables 1726A,1726C.

Information from the smart cables 1622 or other cables is used to identify the electrosurgical units to the pedal control logic 1700A. The robotic surgical tools 101A-101B, when mounted to a robotic arm, communicate information regarding their tool type to the pedal control logic 1700A over the connections 1621A-1621B. In this manner, the pedal control logic knows the electrosurgical units 102A-102C and the robotic surgical tools 101A-101B that are a part of the integrated robotic surgical system 1600. The engagement of a tool to the robotic arm can trigger a mapping of the foot pedals to remote controlled equipment. In response to the information about the robotic electrosurgical tools 101A-101B, the electro surgical units 102A-102C, and one or more user selections, the pedal control logic 1700A multiplexes or maps the control signals from the pedals to the appropriate electrosurgical units 102A, 102C to provide energy to the appropriate robotic surgical tool as desired by the user at the surgeon's control console. That is, the mapping of the foot pedals to the remote controlled equipment is a hot hand mapping and not just a functional mapping. The user selects which of one or more robotic surgical tools mounted to the robotic arms is to be active (selects the handedness) to receive a supply from the remote controlled equipment under control of one or more foot pedals in the surgeon's console. If the remote controlled equipment is inappropriate for the selected active robotic surgical tool, the foot pedals are disabled (they will not fire) so that the remote controlled equipment will not supply the vacuum, gas, liquid, or energy to the robotic surgical tool as a safety measure.

After the mapping is completed correctly, a foot pedal may be pressed to activate a switch to signal to the remote controlled equipment to supply vacuum, gasses, liquids, energy, mechanical torques, mechanical forces, data signals, control signals, etc. to one or more robotic surgical tools.

In an alternate embodiment of the invention, the pedal control logic need not be coupled to the electrosurgical units 102A-102C. Instead, a control signal path may provided from the robotic surgical tools to the electrosurgical units or other remote controllable equipment so that the tools control their own supply of electrical energy, gas, liquid, etc. from the ESUs or the other remote controllable equipment.

Figure 17B:
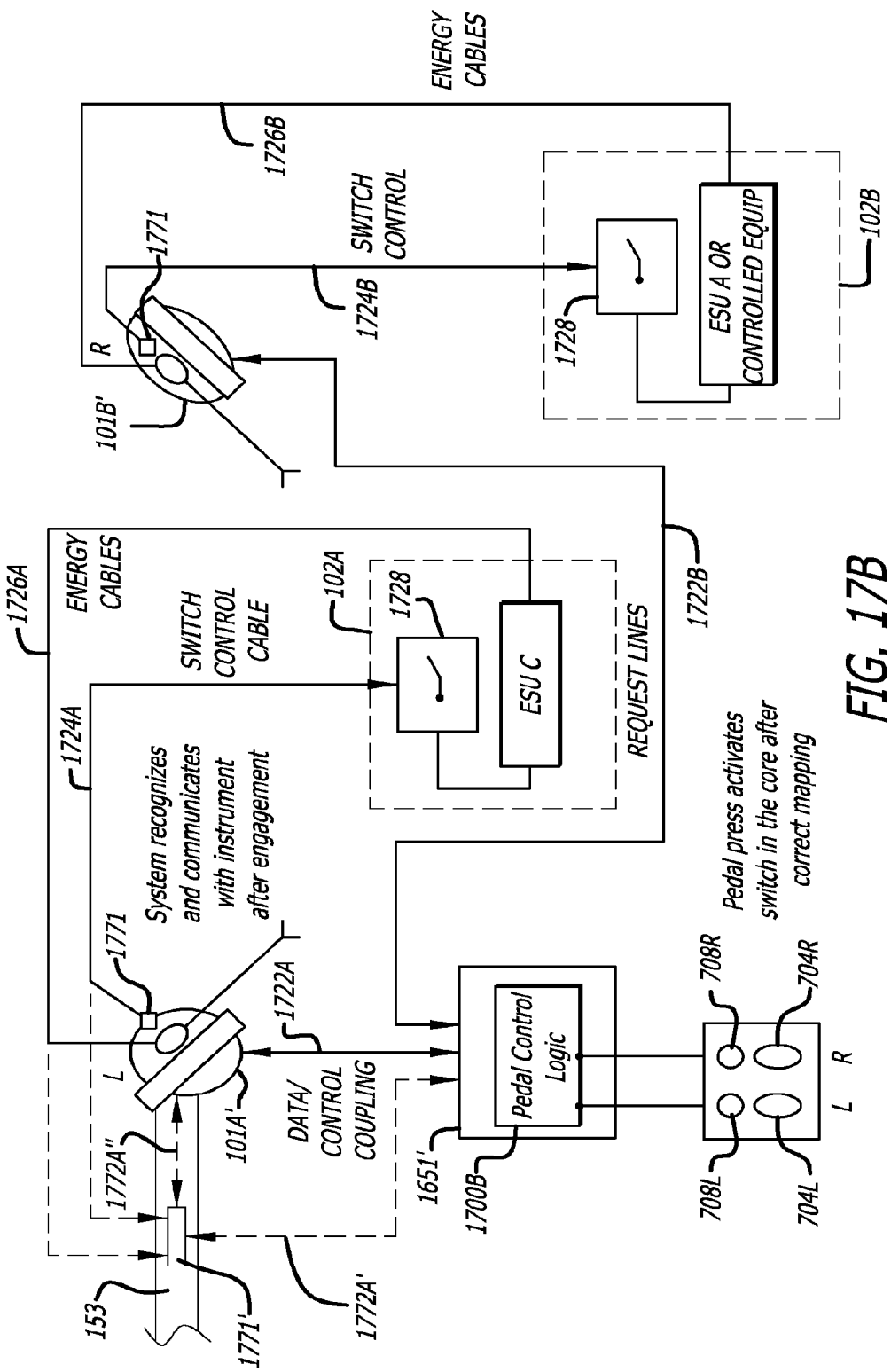

Referring now to FIG. 17B, a simplified block diagram another embodiment of the integrated robotic surgical control system is illustrated in which pedal control logic 1700B of the integrated user interface controller 1651' is coupled between the foot pedal switches 704L,704R,708L,708L and intelligent robotic surgical tools 101A'-101B'. In this case, the integrated user interface controller 1651' need not be coupled to the remote controllable equipment 1610 (including the ESUs 102A-102B). Thus, the communication interface between the integrated user interface controller 1651' and the intelligent robotic surgical tools 101A'-101B' may be simplified.

The intelligent robotic surgical tools 101A'-101B' are similar to the robotic surgical tools 101A-101B but additionally include their own controller and optionally, an adaptable input/output interface 1771 to generate control signals to control the remote controllable equipment 1610 in response to a user's inputs from the user interface input devices 1601A-1601B. That is, the intelligent robotic surgical tools 101A'-101B' may act as a control signal relay to relay the commands of the user to the remote controllable equipment. The adaptable I/O interface 1771 may read equipment information from the one or more pieces of remote controlled equipment 102A-102B (alternatively from a storage device in one or more smart cables) and may adapt signal levels to the control signal levels that the remote controlled equipment desires. That is, the adaptable I/O interface 1771 may emulate the foot pedal switch ordinarily expected by the remote controlled equipment.

The plurality of foot pedals 704L-704R, 708L-708R are coupled to the pedal control logic 1700B to receive control signals from the user. The pedal control logic 1700B communicates and is coupled to each of the robotic surgical tool 101A'-101B' by means of a data/control connection 1722A-1722B. A control signal path is provided by a switch control cable 1724A-1724B coupled between the robotic surgical tools 101A'-101B' and the electrosurgical units 102A, 102B. The cables 1724A-1724B may be a smart cable including data lines to read data (e.g., equipment information) and control lines or cables to control the remote controlled equipment (e.g., the electrosurgical generating units). Electrical energy generated by the electrosurgical units 102A, 102B when activated, is supplied from the ESU to the respective robotic surgical tools 101A'-101B' over one or more energy supply cables 1726A-1726B. In the case of a bipolar ESU and bipolar robotic electrosurgical tool, two energy supply cables are coupled between the ESU and the tool. With different types of remote controlled equipment, the cables 1726A-1726B may be referred to as supply cables to supply a vacuum, gasses, liquids/fluids, or energy (e.g., electrosurgical, laser, ultrasound) to a robotic surgical tool.

In an alternate embodiment of the invention, the robotic surgical tools 101A'-101B' may be standard the robotic surgical tools 101A-101B and the cables 1724A-1724B, 1726A-1726B, 1722A-1722B may couple to an adaptable I/O interface 1771' in the robotic arms 153 to control the remote controlled equipment and the supply to the robotic surgical tools, as shown by the optical cables around the robotic surgical tool 101A' in FIG. 17B.

The pedal control logic 1700B includes the mapping logic 1672 to appropriately map foot pedal control signals from the foot pedal switches over the data/control connection 1722A-1722B to the appropriate robotic surgical tool 101A'-101B'. Information regarding the robotic surgical tools 101A'-101B' is received by the pedal control logic 1700B over the data/control connections 1722A-1722B. The data/control coupling 1722A-1722B passes requests/control signals from the foot pedals to the respective robotic surgical tool 101A'-101B'. The robotic surgical tool 101A'-101B' passes the request/control signal to the respective electrosurgical unit 102A-102B via a respective switch control cable 1724A-1724B. In this manner, the robotic surgical tools themselves control the supply of electrosurgical energy over the energy cables 1726A-26B. Note that the switch control cable 1724A-1724B may be grouped together with the respective energy cable(s) 1726A, 1726B to provide a single cable coupled between the remote controllable equipment 1610 (ESU) and the robotic surgical tools 101A'-101B'.

Upon mounting the intelligent robotic surgical tools 101A'-101B' to the robotic arms of the robotic surgical system, the system reads the stored data in the tool to recognize the type of tool and properly communicate with it and the corresponding remote controllable equipment. Additionally, the intelligent robotic surgical tools 101A'-101B' may have a cable detection device or switch to detect when one of the cables 1724A-1724B or 1726A-1726B is plugged into the tool. Upon detection, information regarding the remote controlled equipment, such as the electrosurgical unit may be downloaded. Alternatively, the ESU may send a low energy signal that can be recognized by the instrument when they are coupled together. The connectors of the tool may be polled by software to detect the low energy signal indicating a connection has been made. Information from the electrosurgical units may then be downloaded and read by the intelligent robotic surgical tools.

The intelligent robotic surgical tools or instruments 101A'-101B' may directly communicate with an electrosurgical generating unit ESU to directly command it to energize and supply electrical energy to the surgical tool. Alternatively, the intelligent robotic surgical tools or instruments 101A'-101B' may have a relay to control the activation of energy by the electro-surgical units or prevent the supply of energy to a tool in the case of a misconnection in the control cable. In either case, the electrosurgical generating units 102A-102B may have an integrated control switch or signal translating unit 1728 coupled to the switch control cable 1724A-1724B. The integrated control switch or signal translating unit 1728 converts signals on the switch control cable into a firing signal to control an electrosurgical unit 102A or 102B or other controlled equipment. If no signal translation is needed, the unit 1728 may just be an input receiver to receive a control signal from the intelligent robotic surgical tool.

Figure 18A:
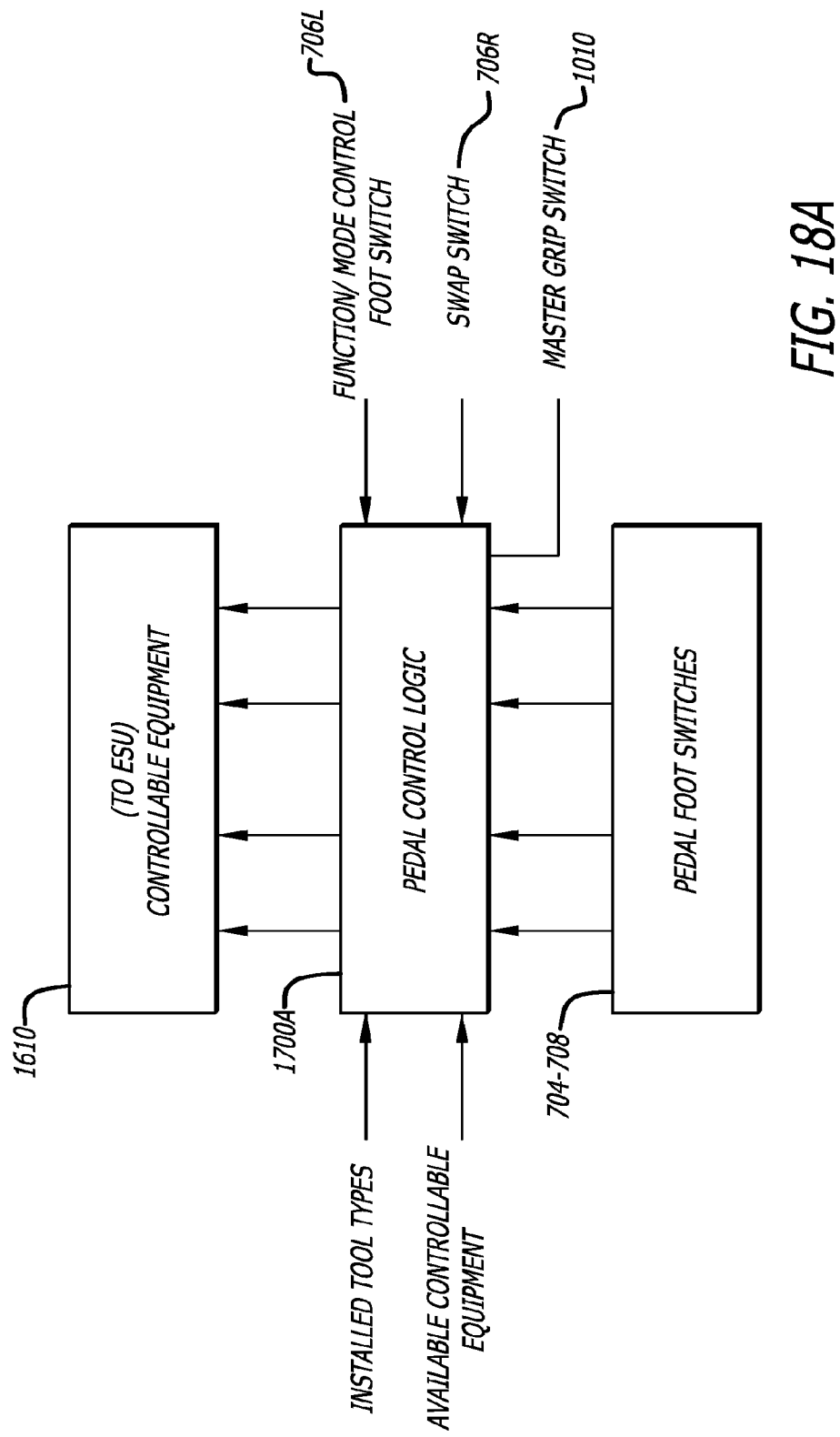
FIGS. 18A-18B illustrate a block diagram of the pedal control logic and alternate input/output signal flow corresponding to the alternate embodiments of the integrated robotic surgical control system. shown in FIGS. 17A-17B.

Referring now to FIG. 18A, a block diagram of the pedal control logic 1700A shown in FIG. 17A is illustrated. To control the multiplexing of signals from the foot pedal switches to the remote controllable equipment 1610, the pedal control logic 1700A receives information regarding the installed tool types from the one or more tools 101, information regarding the available remote controllable equipment from the equipment itself, and control signals from the user controllable switches that affect how some foot pedal switches may control the remote controllable equipment. These user controllable switches may include a function mode control switch associated with a foot pedal 706L, a swap switch associated with the foot pedal 706R, and/or one or more master switches 1010 associated with the master grips of the master controllers. In this case, the mapping of the foot pedal switches by the pedal control logic is context sensitive.

In particular, the energy swap switch of the swap pedal 706R (also referred to as a control swap pedal) contextively controls the mapping or multiplexing of the control signals from the foot pedal switches to the remote controllable equipment 1610. The energy swap switch of the swap pedal 706R determines which one of two electro surgical tools mounted to the robotic surgical arms is to have its remote controlled equipment controlled by the energy control foot pedals. The energy swap switch of the right vertical pedal 706R alters the handedness of the foot pedal control supplying energy to the electro-surgical tools, swapping between the left hand side and the right hand side. The energy swap switch of the right vertical pedal 706R generates a control swap signal (also referred to as an active tool signal or an energy swap signal for electrosurgical tools and generators) to alter the mapping of the control signals from the foot pedal switches of pedals 704R,708R to the available electrosurgical generators for support of the available energy tools that is selected. For example, the control swap signal may swap between active control of a first remote controlled equipment and a second remote controlled equipment in the support (e.g., supply of vacuum, gasses, liquids, energy, mechanical torques, mechanical forces, data signals, control signals, etc.) to a first robotic surgical tool and a second robotic surgical tool, respectively. Alternatively, it may alter the control of the same piece of remote controlled equipment that can support two or more tools concurrently. For example, the control swap signal may swap control of a first remote controlled equipment in the support (e.g., supply of vacuum, gasses, liquids, energy, etc.) to the first robotic surgical tool and the second robotic surgical tool.

A function/mode control switch in a left vertical pedal 706L (also referred to as an arm or tool swap pedal) may also be used to control the multiplexing of the foot pedal control signals through the pedal control logic to the electrosurgical tools 101. The function/mode control switch of the left vertical pedal 760L may generate a tool swap signal to swap the kinematic control of one tool for another. For example, on a right hand side, one tool is active and under control of the master controller at the surgeon's console while another tool is inactive or idle. Electrical energy is typically not supplied to an inactive or idle tool that is not controlled by one of the master controllers. With each tool swap between tools, the controlled features and the remote controlled equipment can change. Thus, with each tool swap signal to change control between swappable tools, the mapping or multiplexing of the control signals from the foot pedal switches to the remote controllable equipment 1610 can change.

If a master switch 1010 is selected (such as to clutch one of the master controllers), the pedal control logic may also disable one or more control signals from the foot pedal switches in the foot pedals 704L,704R,706L,706R,708L, 708R. In this case, one or more of the input/output interfaces of the integrated controller may be disabled so that an inadvertent press on a foot pedal does not supply energy to a tool that is clutched or disengaged from a master controller.

The tool types of the one or more robotic surgical tools 101 also influences the mapping or multiplexing of the control signals from the foot pedal switches. Each piece of remote controllable equipment 1610 may require one or more control signals from one or more foot pedals for its features to be controlled properly. For example, consider an electrosurgical tool that is mated to robotic surgical arm is a bipolar collector surgical tool. In this case, only one foot pedal switch is needed to activate the controlled equipment to supply electrosurgical energy to the bipolar tool. In another example, consider the installed tool type is a monopolar electrosurgical tool. In this case, a pair of foot pedal switches may be used to control the remote controllable equipment to supply primary and secondary electrical energy to the monopolar electrosurgical tool. In either case, the pedal control logic surveys all the remote controllable equipment 1610 coupled to it and all the type of robotic surgical tools 101 mounted to the robotic surgical arms in order to determine how to map control signals from the foot pedals to control the remote controllable equipment. With smart cables, a surgeon can dynamically map the foot pedals to energy instruments without explicit communication with the electrosurgical generating units (ESUs).

Figure 18B:
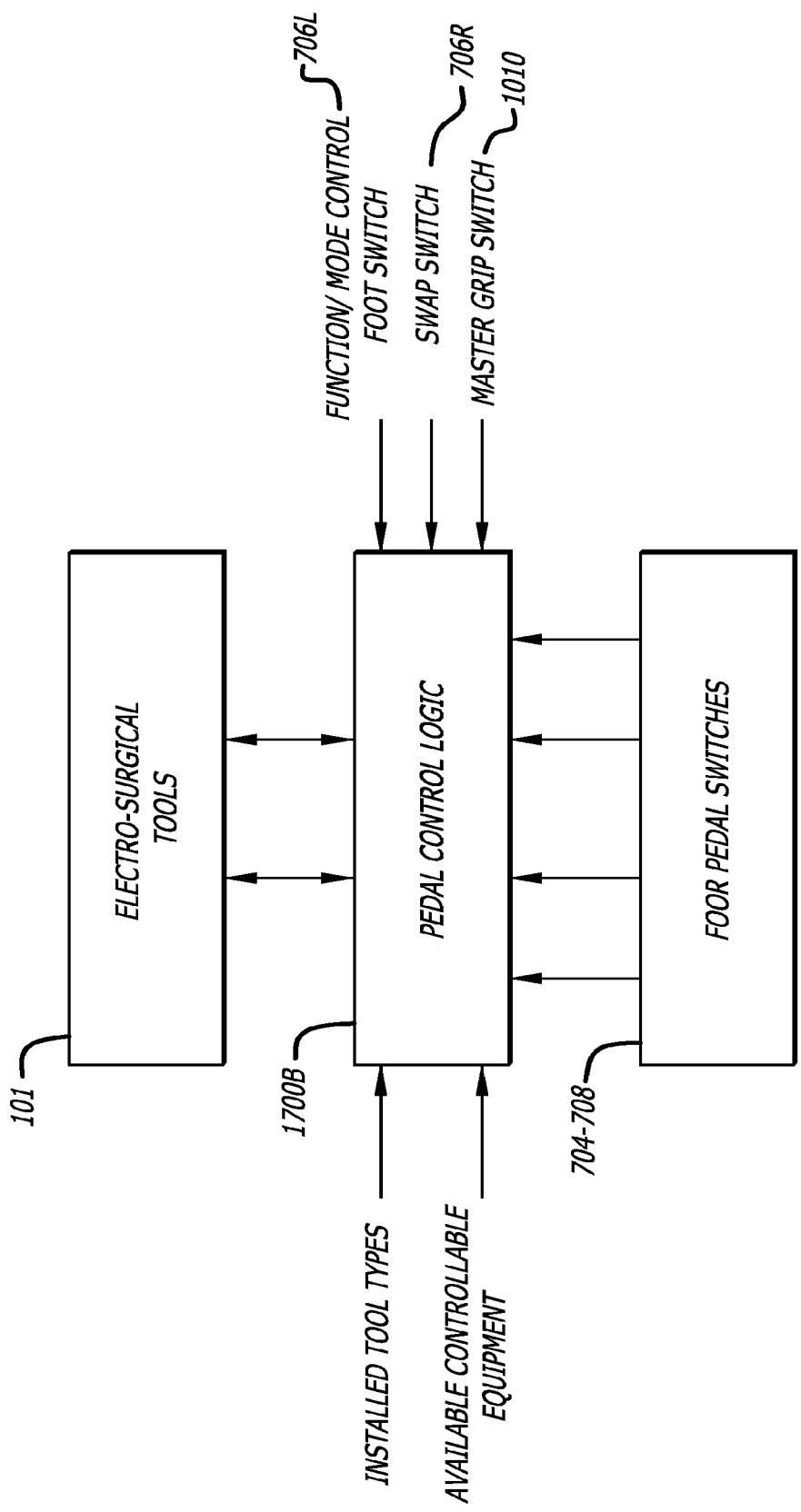

Referring now to FIG. 18B, a block diagram of the pedal control logic 1700B shown in FIG. 17B is illustrated. Pedal control logic 1700B interfaces to the foot pedal switches 704L-704R, and 708L-708R to receive control signals that are multiplexed into the one or more electrosurgical tools 101 mounted to the robotic surgical arms, instead of the remote controlled equipment 1610. Otherwise, the pedal control logic 1700B is similar in that it may also receive information regarding the installed tool types, the available remote controllable equipment 1610, an energy/control swap signal from the pedal switch 706R, an arm/tool swap signal from the pedal switch 706L, and a function/mode control switch in order to multiplex the control signals towards the appropriate electrosurgical tool. The pedal control logic 1700B is also context sensitive similar to the pedal control logic 1700A. In this manner, a surgeon can dynamically map the foot pedals to energy instruments.

The adaptable integrated controller allows a plurality of electrosurgical generating units (ESU) to be coupled to and controlled by a single surgeon console. The adaptable integrated controller vitiates a need for extension pedals outside of the normal working footspace of the surgeon's console to control additional remote controlled equipment of the system. The robotic surgical system can be set up with a proper mapping of the foot pedals to the remote controlled equipment and the robotic surgical tools prior to a surgical procedure to increase efficiency. The graphical user interface described herein may be displayed to the surgeon to communicate the state of the system and how the energy pedals are mapped.

Software, hardware, or a combination thereof may be used to control the active mapping of multiple remote controlled pieces of equipment (ESUs) to one or more instruments and one or more foot pedal switches.

Smart Cable

Figure 19:
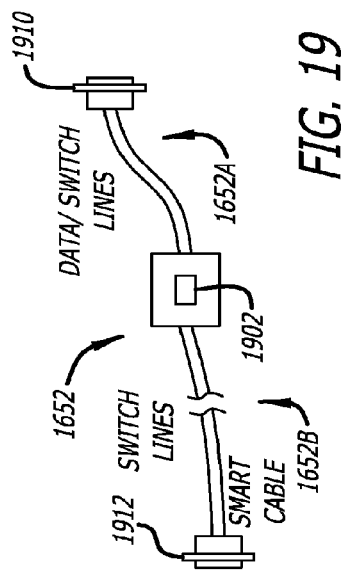
FIG. 19 illustrates a perspective view of a smart cable.

Referring now to FIG. 19, a perspective view of a smart cable 1652 is illustrated. The smart cable 1652 includes a first cable portion 1652A between a first connector 1910 and a data storage device 1902, and a second cable portion 1652B between a second connector 1912 and the data storage device 1902. The second connector 1912 of the smart cable 1652 is configured to interface to a receptacle of one or more of the remote controllable equipment 1610. The first connector 1910 may be configured to couple to the integrated controller 1651 or to the intelligent robotic surgical tools 101A'-101B'. To avoid disconnections, the first and second connectors may be lockable connectors, such as a bayonet or a threaded connector, that couple to bayonet or threaded receptacles, respectively.

The first cable portion 1652A of the smart cable has both data and switch control lines. The data lines are routed between the data storage device 1902 and the first connector 1910 to read information from the data storage device. As the input/output interfaces 1671A-1671N of the controllable equipment interface 2110 and adaptable input/output interface 1771 can adapt to the required signaling for each remote controllable equipment, there is no need for signal conversion in the smart cable. The switch control lines may be routed between the first connector 1910 and the second connector 1912 bypassing the data storage device 1902. In this manner, the second cable portion 1652B of the smart cable 1652 may not have data lines but switch control lines alone.

The data storage device 1902 may be an integrated circuit chip with a non-volatile memory to store an identifying number or information of a particular piece of remote controllable equipment 1610. For example, the identification or information (e.g., make, model, remote controls, signal levels, etc.) may indicate the manufacture of the remote controllable equipment, the type of remote controllable equipment, and the manner in which the remote controllable equipment may be controlled by the foot pedal switches of the foot pedals. The information in the data storage device (also referred to as equipment information) provides a description of the remote controllable equipment (e.g., ESU) to which the smart cable is attached so that the user interface may adapt. With the addition of the tool information (e.g., instrument location information, tool type information, etc.) from the tools mounted to the robotic arms, the foot pedals can be mapped to appropriately control the remote controllable equipment when a tool is active.

Alternatively, given remote controllable equipment 1610 with improved communications capability, the smart cable may be replaced by a bidirectional data cable, such as an RS232 cable for example. In this case, data lines may be coupled between the remote controllable equipment 1610 and the integrated controller 1651 so that data can be bi-directionally communicated. The integrated controller 1651 can then poll the remote controllable equipment for information that can be used to set up and remotely control it to supply energy, gas, or liquids to a robotic surgical tool.

Adaptable Input/Output Interface

As described previously, the integrated controller 1651 has a plurality of adaptable input-output (I/O) interfaces 1671A-1671N. Each of the intelligent robotic surgical tools 101A'-101B' may include an adaptable input output interface 1771 to couple to remote controllable equipment. The input-output interfaces 1671A-1671N,1771 can adapt to the type of signal requirements needed by the remote controllable equipment 1610 over the control lines of the smart cable. That is, signal levels formed by the closing and opening of the foot pedal switches can be adapted by the adaptable I/O interfaces to signal levels to control the remote controlled equipment. Each of the I/O interface adaptors includes a control switch 2002. The control switch 2002 may be a transistorized switch or a mechanical relay type switch with a control input terminal to open and close the switch.

Figure 20A:
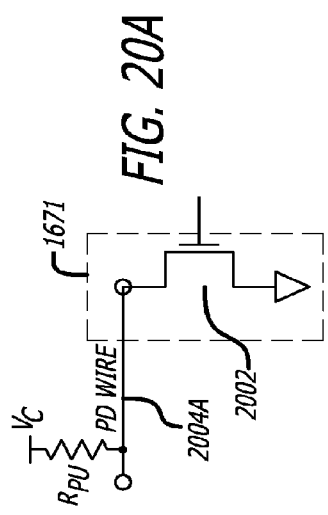
FIGS. 20A-20C illustrate schematic diagrams of how a switch may be adapted to different types of control lines for different remote controlled equipment.
Figure 20B:
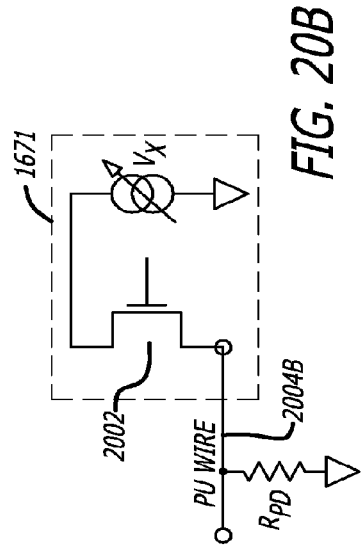
Figure 20C:
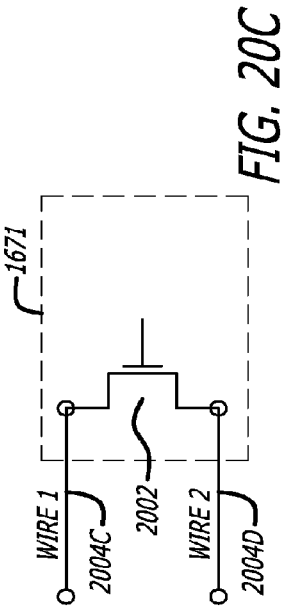

FIGS. 20A-20C illustrate how the switch 2002 may be adapted to different types of control lines. Each input-output interface 1671A-1671N may include one or more control switches 2002 in order to control one or more features of the remote controllable equipment 1610. The connections of each switch 2002 may be made under software control to adapt to the type of signaling needed to control the remote controlled equipment 1610.

In FIG. 20A, a first remote controllable equipment is coupled to an input-output interface 1671 by a first cable. A control line 2004A to the remote controlled equipment is normally pulled up by a pull-up resistor $R_{pu}$ to a pull up voltage Vc by the first remote controllable equipment. The switch 2002 has one pole coupled to the control line 2004A and another pole coupled to ground. When the switch 2002 is closed by a control signal applied to its control terminal from a mapped foot pedal, its poles are coupled together to pull down the control switch line 2004 to signal to the remote controllable equipment, as if a foot pedal were directly attached to the control line 2004A.

In FIG. 20B, a second remote controlled equipment differing from the first is coupled to the input-output interface 1671 by a second cable. In this case, a control line 2004B is pulled to ground through a pull-down resistor $R_{pd}$. The switch 2002 has one pole coupled to the control line 2004B and another pole coupled to a voltage source Vx. In this case when the switch 2002 is closed by a control signal applied to its control terminal from a mapped foot pedal, its poles are coupled together to pull up the control line 2004B to the voltage supplied by the voltage source Vx.

In FIG. 20C, a third remote controlled equipment differing from the first and the second is coupled to the input-output interface 1671 by a third cable. A pair of control lines 2004C, 2004D are provided by the smart cable to control the remote controllable equipment 1610. The pair of control lines are coupled to the poles of the switch 2002. The control lines 2004C and 2004D may be shorted together by a foot pedal switch to signal the remote controlled equipment. In this case, the control switch 2002 is coupled between the control lines 2004C,2004D so that when it is closed, it shorts them together. The control terminal of the switch 2002 receives a control signal from a respectively mapped pedal to open and close the switch.

Computer System with Integrated Controller

Figure 21:
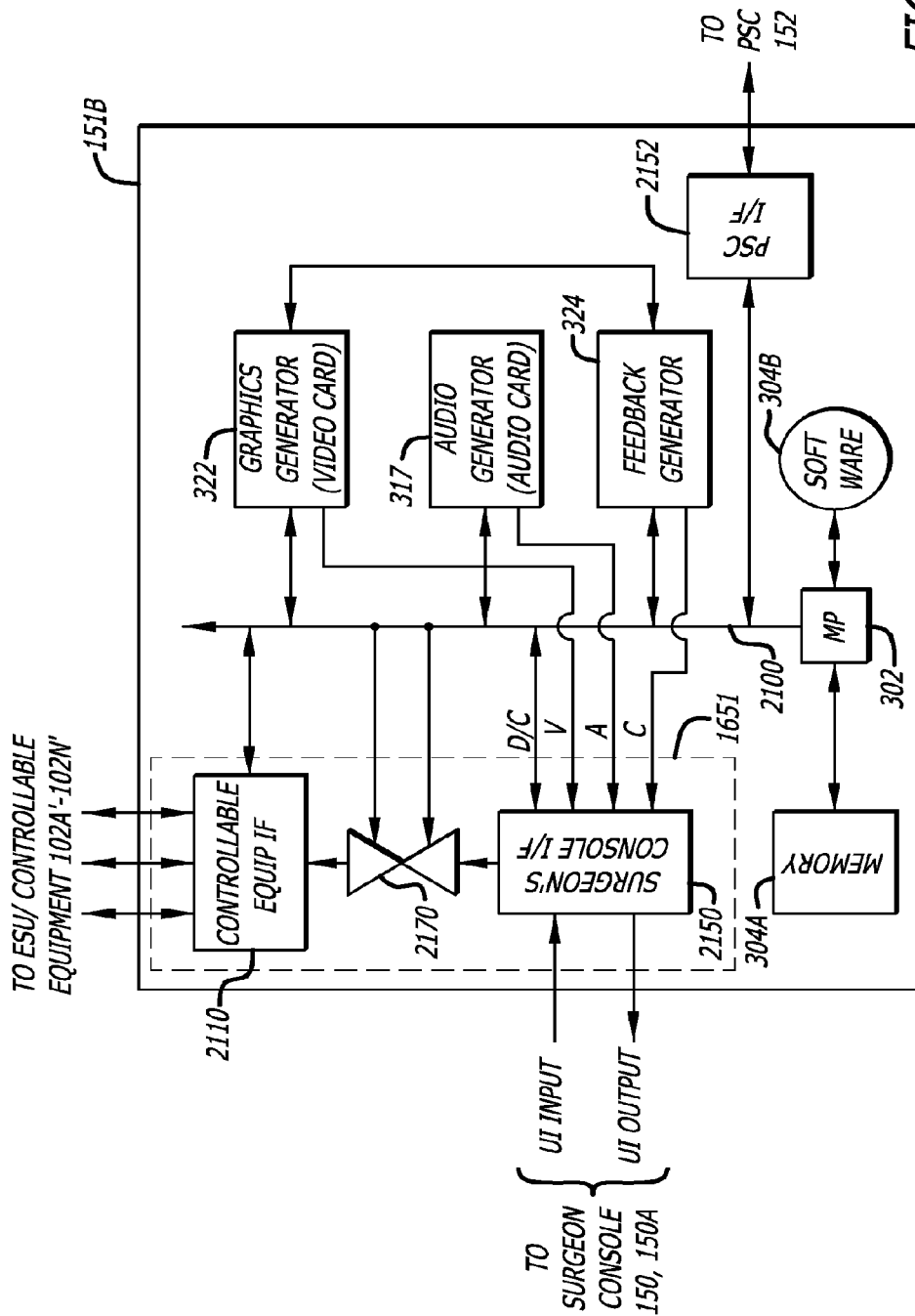
FIG. 21 illustrates a block diagram of a computer system including the functionality of the integrated user interface controller.

Referring now to FIG. 21, a block diagram of a computer system 151,151B with the function of the integrated user interface controller 1651 is illustrated. The computer system 151B further includes one or more microprocessors 302, a scratch pad storage device 304A (memory), a disc like storage device 304B for permanent storage of software, a patient side cart (PSC) interface 2152, an audio generator 317, a graphics generator (video card) 322, and a feedback generator 324 coupled together as shown. Each of the elements of the computer 151,151B may be coupled to a central bus 2100 to communicate with one of the microprocessors 302 or otherwise be directly coupled to a microprocessor via a dedicated bus.

The integrated controller 1651 includes a remote controllable equipment interface 2120, a surgeon's console interface 2150, and a cross point switch 2170.

The remote controllable equipment interface 2120 interfaces the computer to the remote controllable equipment 1610, such as electrosurgical generating units 102A', 102B', by means of smart cables, RS232 cables, or other communication channels.

The surgeon's console interface 2110 interfaces the computer to the surgeon's console 150,150A. The surgeon's console interface 2110 couples to the user interface inputs 1601A,1601B and the user interface outputs 1610A,1610B. The surgeon's console interface 2110 receives control signals from some of the switches of the pedals and couples those into the cross point switch for mapping. The surgeon's console interface 2110 receives control signals from some of the switches of the pedals and couples those onto the bus to be read by the microprocessor for control of the cross-point switch. Other control signals, such as from the master controllers, are coupled onto the bus to be read and processed by the microprocessor and the software programs it executes for controlling the system.

The cross point switch 2170, coupled between the surgeon's console interface 2110 and the controllable equipment interface 2120, may be used to map the control signals from the foot pedals of the surgeon's console to the remote controllable equipment. Otherwise, the cross point switch may be implemented in software or a combination of software and hardware. The pedal control logic 1700A, 1700B described previously may be circuit logic, software stored on the disc storage device 304B executed by the microprocessor, or a combination thereof to control the mapping. With software, the microprocessor can control the cross point switch 2170 to perform the appropriate mapping of the foot pedals to the remote controlled equipment in response to information it receives about the system.

The patient side cart (PSC) interface 2152 interfaces to the patient side cart 152 to control the kinematics of the slave robotic surgical arms and the robotic surgical tools. The PSC interface 2152 receives the video images captured by the endoscopic camera and other sensor data or the surgical arms and tools.

The feedback generator 324 is coupled to the audio generator 317 and the graphics generator 322 to generate audible user feedback and/or visual user feedback. The feedback generator 324 may generate feedback control signals for devices at the surgeon's consoler to provide tactile or vibratory user feedback. The feedback control signals may be coupled into the devices at the surgeon's console through the surgeon's console interface 1602.

Video signals from the graphics generator 322, fusing images of the surgical site together with the graphics of the graphical user interface, may be output to the surgeon's console through the surgeon's console interface 2150 for display on a display device.

Audio signals generated by the audio generator 317, including audio signals generated to provide audible feedback, may be coupled into the speakers of the surgeon's console through the surgeon's console interface 2150.

CONCLUSION

Some portions of the preceding detailed description have been presented in terms of algorithms and symbolic representations of operations on data bits within a computer memory or storage device. These algorithmic descriptions and representations are the tools used by those skilled in the data processing arts to most effectively convey the substance of their work to others skilled in the art. An algorithm is herein, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be kept in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "processing" or "computing" or "calculating" or "determining" or "displaying" or the like, refer to the non-manual, automatic, or automated action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The embodiments of the invention also relate to an apparatus or system for performing the operations described herein. This apparatus may be specially constructed for the required purposes, or it may comprise a general-purpose computer selectively activated or reconfigured by a computer program stored in the computer.

One or more elements in embodiments of the invention may be implemented in software to execute on a processor of a computer system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art. For example, some embodiments of the invention were particularly described with referenced to electrosurgical systems and tools but are applicable to other types of remote controlled medical equipment and their respective surgical instruments.

What is claimed is:

1. A teleoperated surgical system, comprising:
a surgical instrument;
a user input device configured to output an activation request for activating a function of the surgical instrument in response to input at the user input device;
a display configured to output video images of a surgical site at which the surgical instrument is deployed; and
a user interface controller operably coupled to the user input device and to the surgical instrument, the user interface controller being configured to output a feedback signal to cause feedback at the display, the feedback comprising a visual indicator of a state of readiness of the surgical instrument for activation in response to the activation request.

2. The surgical system of claim 1, wherein the user interface controller is further configured to activate the surgical instrument in response to the controller receiving the activation request from the user input device.

3. The surgical system of claim 1, wherein the user interface controller is further configured to delay activation of the surgical instrument for at least a predetermined duration after output of the feedback signal.

4. The surgical system of claim 3, wherein the controller is further configured to:
in response to continuing to receive the activation request from the user input device after expiration of the predetermined duration, activate the surgical instrument; or
in response to not continuing to receive the activation request from the user input device after expiration of the predetermined duration, refrain from activating the surgical instrument.

5. The surgical system of claim 1, wherein the feedback further indicates which of a left-handed or right-handed master input mechanism is controlling movement of the surgical instrument.

6. The surgical system of claim 1, wherein the feedback further comprises additional visual feedback, haptic feedback, audio feedback, or combinations thereof.

7. The surgical system of claim 1, wherein:
the surgical instrument is an electrosurgical instrument; and
the visual indicator is a visual indication of a state of readiness of the surgical instrument to deliver energy.

8. The surgical system of claim 1, wherein the visual indicator is located at a portion of the display in proximity to where the surgical instrument appears in the display.

9. The surgical system of claim 1, wherein the visual indicator is positioned at a periphery of the display.

10. The surgical system of claim 1, wherein the visual indicator comprises a change in appearance of the display.

11. The surgical system of claim 10, wherein the visual indicator comprises a change in appearance of the display located at a portion of the display in proximity to a location of the display at which the surgical instrument appears.

12. The surgical system of claim 1, wherein the visual indicator comprises a change in appearance of the display located at a relative right portion or relative left portion of the display.

13. The surgical system of claim 11, wherein the visual indicator comprises a change in appearance of a portion of a border surrounding a periphery of the display.

14. The surgical system of claim 10, wherein the change in appearance is chosen from at least one of a change of color, a change of brightness, a change in movement, and a change in pattern.

15. The surgical system of claim 1, wherein the visual indicator comprises a number icon representative of a corresponding number assigned to the surgical instrument.

16. The surgical system of claim 1, further comprising an imaging device configured to capture the video images of the surgical site output to the display, wherein the display is further configured to display an additional visual indicator indicating an orientation of the imaging device while capturing the video images of the surgical site.

17. The surgical system of claim 1, wherein the visual indicator further comprises an additional visual indicator indicating a type of the surgical instrument.

18. The surgical system of claim 17, wherein the additional visual indicator is chosen from at least one of colors and alphanumeric characters.

19. The surgical system of claim 17, wherein the additional visual indicator comprises a symbol associated with energy when the type is an electrosurgical instrument.

20. The surgical system of claim 1, wherein the visual indicator further comprises an additional visual indicator of one or more master control devices of the surgical system, the one or more master control devices being operably coupled to operate movement of the surgical instrument in response to input at the one or more master control devices.

21. The surgical system of claim 20, wherein the additional visual indicator of one or more master control devices comprises one or more grip icons.

22. The surgical system of claim 20, wherein the additional visual indicator comprises an additional visual indicator of the user input device.

23. The surgical system of claim 22, wherein the additional visual indicator comprises a pedal icon.

24. A method for controlling a teleoperated surgical system comprising a surgical instrument, the method comprising:
   in response to input at a user input device, transmitting an activation request to cause activation of a function of the surgical instrument, the function being supported by remote-control supply equipment; and
   in response to receiving the activation request from the user input device, outputting a feedback signal to cause feedback at a display configured to output video images of a surgical site at which the surgical instrument is deployed, the feedback being a visual indicator of a state of readiness of the surgical instrument for activation in response to the activation request.

25. A teleoperated surgical system, comprising:
   a surgical instrument;
   a user input device configured to output an activation request for activating a function of the surgical instrument in response to input at the user input device; and
   a display configured to:
      display video images of a surgical site at which the surgical instrument is deployed, and
      display a visual indicator of a state of readiness of the surgical instrument for activation in response to the activation request.

* * * * *